(12) United States Patent
Worrell et al.

(10) Patent No.: US 9,877,720 B2
(45) Date of Patent: Jan. 30, 2018

(54) CONTROL FEATURES FOR ARTICULATING SURGICAL DEVICE

(75) Inventors: Barry C. Worrell, Centerville, OH (US); Zhifan F. Huang, Mason, OH (US); Jason R. Lesko, Harrison, OH (US); Matthew C. Miller, Cincinnati, OH (US); Geoffrey S. Strobl, Williamsburg, OH (US); Gregory A. Trees, Loveland, OH (US); Charles S. Black, Cincinnati, OH (US); William E. Clem, Bozeman, MT (US); Emron Henry, St. Joseph, MI (US); Kevin M. Montgomery, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 1398 days.

(21) Appl. No.: 13/235,623

(22) Filed: Sep. 19, 2011

(65) Prior Publication Data

US 2012/0078243 A1     Mar. 29, 2012

Related U.S. Application Data

(60) Provisional application No. 61/386,094, filed on Sep. 24, 2010.

(51) Int. Cl.
*A61B 19/00*     (2006.01)
*A61B 17/072*    (2006.01)
(Continued)

(52) U.S. Cl.
CPC .............. *A61B 17/07207* (2013.01); *A61B 2017/0038* (2013.01); *A61B 2017/2908* (2013.01);
(Continued)

(58) Field of Classification Search
CPC ............ A61B 18/1445; A61B 18/1442; A61B 2018/0063
(Continued)

(56) References Cited

U.S. PATENT DOCUMENTS 2,715,341 A     8/1955   Hogan
2,818,744 A     1/1958   Moody
(Continued)

FOREIGN PATENT DOCUMENTS

CN         1163558 A     10/1997
CN       102166129 A      8/2011
(Continued)

OTHER PUBLICATIONS

International Search Report dated Dec. 16, 2011 for Application No. PCT/US2011/052707.
(Continued)

*Primary Examiner* — Alyssa M Alter
(74) *Attorney, Agent, or Firm* — Frost Brown Todd LLC

(57) ABSTRACT

An electrosurgical device includes a body, an end effector, a cutting member, and a shaft. The end effector comprises a pair of jaws and at least one electrode that is operable to deliver RF energy to tissue clamped between the jaws. The cutting member is operable to cut tissue clamped between the jaws. The shaft includes an articulation section that is operable to selectively position the end effector at non-parallel positions relative to the longitudinal axis of the shaft. The body includes a controller operable to selectively actuate the articulation section. The controller may include a rotary knob, a pivoting knob, or a pivoting fin, among other things. An electrical coupling may contact a conductive moving member along at least two axes. A resiliently biased lever may assist a trigger in returning from an actuated position to a home position.

17 Claims, 39 Drawing Sheets

(51) Int. Cl.
*A61B 17/00* (2006.01)
*A61B 17/29* (2006.01)

(52) U.S. Cl.
CPC ................. *A61B 2017/2927* (2013.01); *A61B 2017/2946* (2013.01)

(58) Field of Classification Search
USPC ............................................ 606/51, 33, 130
See application file for complete search history.

(56) References Cited

U.S. PATENT DOCUMENTS

| | | | |
|---|---|---|---|
| 2,857,776 A | 10/1958 | Williams | |
| 2,881,645 A | 4/1959 | Kruchten | |
| 3,079,606 A | 3/1963 | Sergeevich et al. | |
| 3,194,530 A | 7/1965 | Heyl | |
| 3,490,675 A | 1/1970 | Green et al. | |
| 4,203,430 A | 5/1980 | Takahashi | |
| 4,483,562 A | 11/1984 | Schoolman | |
| 4,723,936 A | 2/1988 | Buchbinder et al. | |
| 4,880,015 A | 11/1989 | Nieman | |
| 4,945,920 A | 8/1990 | Clossick | |
| 5,020,514 A | 6/1991 | Heckele | |
| 5,125,895 A | 6/1992 | Buchbinder et al. | |
| 5,171,249 A | 12/1992 | Stefanchik et al. | |
| 5,330,502 A | 7/1994 | Hassler et al. | |
| 5,383,888 A | 1/1995 | Zvenyatsky et al. | |
| 5,391,180 A | 2/1995 | Tovey et al. | |
| 5,395,329 A | 3/1995 | Fleischhacker et al. | |
| 5,409,498 A | 4/1995 | Braddock et al. | |
| 5,411,519 A | 5/1995 | Tovey et al. | |
| 5,441,499 A | 8/1995 | Fritzsch | |
| 5,454,827 A | 10/1995 | Aust et al. | |
| 5,462,546 A | 10/1995 | Rydell | |
| 5,514,130 A | 5/1996 | Baker | |
| 5,514,157 A | 5/1996 | Nicholas et al. | |
| 5,540,685 A | 7/1996 | Parins et al. | |
| 5,549,637 A | 8/1996 | Crainich | |
| 5,562,682 A | 10/1996 | Oberlin et al. | |
| 5,582,617 A | 12/1996 | Klieman et al. | |
| 5,607,450 A | 3/1997 | Zvenyatsky et al. | |
| 5,609,601 A | 3/1997 | Kolesa et al. | |
| 5,626,587 A | 5/1997 | Bishop et al. | |
| 5,632,432 A | 5/1997 | Schulze et al. | |
| 5,643,294 A | 7/1997 | Tovey et al. | |
| 5,673,841 A * | 10/1997 | Schulze ........... A61B 17/07207 227/175.1 | |
| 5,700,275 A | 12/1997 | Bell et al. | |
| 5,704,534 A | 1/1998 | Huitema et al. | |
| 5,743,456 A | 4/1998 | Jones et al. | |
| 5,766,196 A | 6/1998 | Griffiths | |
| 5,766,205 A | 6/1998 | Zvenyatsky et al. | |
| 5,782,859 A | 7/1998 | Nicholas et al. | |
| 5,817,119 A | 10/1998 | Klieman et al. | |
| 5,833,695 A | 11/1998 | Yoon | |
| 5,865,361 A | 2/1999 | Milliman et al. | |
| 5,915,616 A | 6/1999 | Viola et al. | |
| 5,921,956 A | 7/1999 | Grinberg et al. | |
| 5,931,832 A | 8/1999 | Jensen | |
| 5,964,394 A | 10/1999 | Robertson | |
| 6,010,054 A | 1/2000 | Johnson et al. | |
| 6,162,208 A | 12/2000 | Hipps | |
| 6,179,809 B1 | 1/2001 | Khairkhahan et al. | |
| 6,202,914 B1 | 3/2001 | Geiste et al. | |
| 6,423,059 B1 | 7/2002 | Hanson et al. | |
| 6,500,176 B1 | 12/2002 | Truckai et al. | |
| 6,554,794 B1 | 4/2003 | Mueller et al. | |
| RE38,335 E | 11/2003 | Aust et al. | |
| 6,669,073 B2 | 12/2003 | Milliman et al. | |
| 6,783,524 B2 | 8/2004 | Anderson et al. | |
| 6,978,921 B2 | 12/2005 | Shelton et al. | |
| 6,991,627 B2 | 1/2006 | Madhani et al. | |
| 7,004,938 B2 | 2/2006 | Ormsby et al. | |
| 7,055,731 B2 | 6/2006 | Shelton et al. | |
| 7,070,595 B2 | 7/2006 | Ormsby et al. | |
| 7,081,114 B2 | 7/2006 | Rashidi | |
| 7,087,071 B2 | 8/2006 | Nicholas et al. | |
| 7,112,201 B2 | 9/2006 | Truckai et al. | |
| 7,125,409 B2 | 10/2006 | Truckai et al. | |
| 7,128,254 B2 | 10/2006 | Shelton et al. | |
| 7,141,897 B2 | 11/2006 | Park | |
| 7,143,925 B2 | 12/2006 | Shelton et al. | |
| 7,150,749 B2 | 12/2006 | Dycus et al. | |
| 7,156,846 B2 | 1/2007 | Dycus et al. | |
| 7,159,750 B2 | 1/2007 | Racenet et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,208,005 B2 | 4/2007 | Frecker et al. | |
| 7,220,951 B2 | 5/2007 | Truckai et al. | |
| 7,309,849 B2 | 12/2007 | Truckai et al. | |
| 7,311,709 B2 | 12/2007 | Truckai et al. | |
| 7,338,513 B2 | 3/2008 | Lee et al. | |
| 7,354,440 B2 | 4/2008 | Truckal et al. | |
| 7,380,696 B2 | 6/2008 | Shelton, IV et al. | |
| 7,381,209 B2 | 6/2008 | Truckai et al. | |
| 7,404,508 B2 | 7/2008 | Smith et al. | |
| 7,424,965 B2 | 9/2008 | Racenet et al. | |
| 7,455,208 B2 | 11/2008 | Wales et al. | |
| 7,481,348 B2 | 1/2009 | Marczyk | |
| 7,494,039 B2 | 2/2009 | Racenet et al. | |
| 7,500,979 B2 | 3/2009 | Hueil et al. | |
| 7,506,790 B2 | 3/2009 | Shelton, IV | |
| 7,540,872 B2 * | 6/2009 | Schechter .......... A61B 18/1445 606/50 | |
| 7,549,564 B2 | 6/2009 | Boudreaux | |
| 7,553,275 B2 | 6/2009 | Padget et al. | |
| 7,559,450 B2 | 7/2009 | Wales et al. | |
| 7,584,880 B2 | 9/2009 | Racenet et al. | |
| 7,594,913 B2 | 9/2009 | Ormsby et al. | |
| 7,597,230 B2 | 10/2009 | Racenet et al. | |
| 7,615,044 B2 | 11/2009 | Scheibe et al. | |
| 7,654,431 B2 | 2/2010 | Hueil et al. | |
| 7,658,311 B2 | 2/2010 | Boudreaux | |
| 7,691,095 B2 | 4/2010 | Bednarek et al. | |
| 7,703,653 B2 | 4/2010 | Shah et al. | |
| 7,708,182 B2 | 5/2010 | Viola | |
| 7,721,935 B2 | 5/2010 | Racenet et al. | |
| 7,766,910 B2 | 8/2010 | Hixson et al. | |
| 7,771,425 B2 | 8/2010 | Dycus et al. | |
| 7,780,054 B2 | 8/2010 | Wales | |
| 7,784,662 B2 | 8/2010 | Wales et al. | |
| 7,793,814 B2 | 9/2010 | Racenet et al. | |
| 7,798,386 B2 | 9/2010 | Schall et al. | |
| 7,799,028 B2 | 9/2010 | Schechter et al. | |
| 7,815,090 B2 | 10/2010 | Marczyk | |
| 7,815,091 B2 | 10/2010 | Marczyk | |
| 7,815,637 B2 | 10/2010 | Ormsby et al. | |
| 7,819,298 B2 | 10/2010 | Hall et al. | |
| 7,828,725 B2 | 11/2010 | Maruyama | |
| 7,832,408 B2 | 11/2010 | Shelton et al. | |
| 7,842,025 B2 | 11/2010 | Coleman et al. | |
| 7,857,183 B2 | 12/2010 | Shelton, IV | |
| 7,909,220 B2 | 3/2011 | Viola | |
| 8,033,441 B2 | 10/2011 | Marczyk | |
| 8,062,306 B2 | 11/2011 | Nobis et al. | |
| 8,092,451 B2 | 1/2012 | Schechter et al. | |
| 8,100,309 B2 | 1/2012 | Marczyk | |
| 8,142,473 B2 | 3/2012 | Cunningham | |
| 8,152,799 B2 | 4/2012 | Ormsby et al. | |
| 8,161,838 B2 | 4/2012 | Duval | |
| 8,197,479 B2 | 6/2012 | Olson et al. | |
| 8,205,619 B2 | 6/2012 | Shah et al. | |
| 8,236,010 B2 | 8/2012 | Ortiz et al. | |
| 8,241,320 B2 | 8/2012 | Lyons et al. | |
| 8,292,147 B2 | 10/2012 | Viola | |
| 8,292,889 B2 | 10/2012 | Cunningham et al. | |
| 8,308,659 B2 | 11/2012 | Scheibe et al. | |
| 8,317,811 B2 | 11/2012 | Laporte Rosello et al. | |
| 8,323,239 B2 | 12/2012 | Bednarek et al. | |
| 8,323,297 B2 | 12/2012 | Hinman et al. | |
| 8,353,902 B2 | 1/2013 | Prakash | |
| 8,357,161 B2 | 1/2013 | Mueller | |
| 8,361,067 B2 | 1/2013 | Pellegrino et al. | |

(56) References Cited

U.S. PATENT DOCUMENTS

| | | |
|---|---|---|
| 8,366,709 B2 | 2/2013 | Schechter et al. |
| 8,372,064 B2 | 2/2013 | Douglass et al. |
| 8,398,673 B2 | 3/2013 | Hinchliffe et al. |
| 8,403,832 B2 | 3/2013 | Cunningham et al. |
| 8,403,945 B2 | 3/2013 | Whitfield et al. |
| 8,789,741 B2 | 7/2014 | Baxter, III et al. |
| 9,089,327 B2 | 7/2015 | Worrell et al. |
| 9,545,253 B2 | 1/2017 | Worrell et al. |
| 9,545,323 B2 | 1/2017 | Cully |
| 2003/0163085 A1 | 8/2003 | Tanner et al. |
| 2006/0259071 A1 | 11/2006 | Nicholas et al. |
| 2007/0043353 A1 | 2/2007 | Dycus et al. |
| 2007/0095877 A1 | 5/2007 | Racenet et al. |
| 2007/0175961 A1 | 8/2007 | Shelton et al. |
| 2007/0219550 A1 | 9/2007 | Thompson et al. |
| 2007/0282324 A1 | 12/2007 | Vaska et al. |
| 2008/0161798 A1 | 7/2008 | Podmore et al. |
| 2009/0088792 A1 | 4/2009 | Hoell et al. |
| 2009/0125019 A1 | 5/2009 | Douglass et al. |
| 2009/0188965 A1 | 7/2009 | Levin et al. |
| 2009/0198272 A1 | 8/2009 | Kerver et al. |
| 2009/0283568 A1 | 11/2009 | Racenet et al. |
| 2010/0094289 A1 | 4/2010 | Taylor et al. |
| 2010/0179540 A1 | 7/2010 | Marczyk |
| 2010/0179545 A1 | 7/2010 | Twomey |
| 2010/0193566 A1 | 8/2010 | Scheib et al. |
| 2010/0249759 A1 | 9/2010 | Hinman et al. |
| 2010/0298824 A1 | 11/2010 | Rothstein et al. |
| 2011/0009863 A1 | 1/2011 | Marczyk et al. |
| 2011/0087218 A1 | 4/2011 | Boudreaux et al. |
| 2011/0184459 A1 | 7/2011 | Malkowski et al. |
| 2011/0213361 A1 | 9/2011 | Cunningham et al. |
| 2011/0213363 A1 | 9/2011 | Cunningham et al. |
| 2011/0230875 A1 | 9/2011 | Walberg et al. |
| 2011/0264074 A1 | 10/2011 | Tegg et al. |
| 2011/0282176 A1 | 11/2011 | Tegg |
| 2012/0074200 A1 | 3/2012 | Schmid et al. |
| 2012/0109186 A1 | 5/2012 | Parrott et al. |
| 2012/0143088 A1 | 6/2012 | Schultz |
| 2012/0179151 A1 | 7/2012 | Mueller |
| 2012/0203169 A1 | 8/2012 | Tegg |
| 2012/0215220 A1 | 8/2012 | Kerver et al. |
| 2012/0253326 A1 | 10/2012 | Kleyman |
| 2012/0265186 A1 | 10/2012 | Burger et al. |
| 2012/0303013 A1 | 11/2012 | Burell et al. |
| 2012/0316560 A1 | 12/2012 | Hassoun |
| 2013/0012929 A1 | 1/2013 | Malkowski |
| 2013/0012986 A1 | 1/2013 | Suzuki |
| 2013/0026868 A1 | 1/2013 | Klafter et al. |
| 2013/0032627 A1 | 2/2013 | Viola |
| 2013/0041403 A1 | 2/2013 | Cunningham et al. |
| 2013/0096407 A1 | 4/2013 | Bednarek et al. |

FOREIGN PATENT DOCUMENTS

| | | |
|---|---|---|
| CN | 102647949 A | 8/2012 |
| DE | 43 00 307 | 7/1994 |
| EP | 1637086 | 3/2006 |
| EP | 2151204 | 2/2010 |
| EP | 2 198 787 | 6/2010 |
| FR | 2 915 873 | 11/2008 |
| WO | WO 00/67834 | 11/2000 |
| WO | WO 2008/045348 | 4/2008 |
| WO | WO 2010/104755 | 8/2010 |
| WO | WO 2011/044343 | 4/2011 |
| WO | WO 2012/067468 | 5/2012 |
| WO | WO 2012/078951 | 6/2012 |

OTHER PUBLICATIONS

International Search Report dated Dec. 28, 2011 for Application No. PCT/US2011/052712.
International Search Report dated Mar. 19, 2012 for Application No. PCT/US2011/053028.
International Search Report and Written Opinion dated Jan. 24, 2012 for PCT/US2011/052734.
U.S. Appl. No. 13/151,481, filed Jun. 2, 2011, Yates et al.
U.S. Appl. No. 13/235,648, filed Sep. 19, 2011, Worrell et al.
U.S. Appl. No. 13/235,660, filed Sep. 19, 2011, Worrell et al.
U.S. Appl. No. 13/235,683, filed Sep. 19, 2011, Worrell et al.
International Search Report dated Jan. 30, 2014 for Application No. PCT/US2013/060537.
International Search Report dated Jan. 31, 2014 for Application No. PCT/US2013/060536.
Restriction Requirement dated Sep. 4, 2014 for U.S. Appl. No. 13/235,648.
Office Action Non Final dated Sep. 5, 2014 for U.S. Appl. No. 13/622,729.
U.S. Appl. No. 61/410,603, filed Nov. 5, 2010.
Australian Examiner's Report dated Aug. 15, 2013 for Application No. AU 2011305198, 5 pages.
Australian Examiner's Report dated Aug. 14, 2013 for Application No. AU 2011305205, 4 pages.
Australian Examiner's Report dated Aug. 8, 2013 for Application No. AU 2011305397, 5 pages.
Chinese First Office Action dated Dec. 17, 2014 for Application No. CN 2011800460673, 13 pages.
International Written Opinion dated Dec. 16, 2011 for Application No. PCT/US2011/052707, 7 pages.
International Written Opinion dated Dec. 28, 2011 for Application No. PCT/US2011/052712, 8 pages.
International Written Opinion dated Jun. 13, 2012 for Application No. PCT/US2011/053016, 8 pages.
International Written Opinion dated Mar. 19, 2012 for Application No. PCT/US2011/053028, 7 pages.
International Written Opinion dated Jan. 31, 2014 for Application No. PCT/US2013/060536, 5 pages.
International Written Opinion dated Jan. 30, 2014 for Application No. PCT/US2013/060537, 5 pages.
U.S. Office Action, Notice of Allowance, dated Dec. 17, 2014 for U.S. Appl. No. 13/622,729, 5 pages.
U.S. Office Action, Non-Final, dated Dec. 19, 2014 for U.S. Appl. No. 13/622,735, 7 pages.
Abstract and Machine Translation of German Patent No. DE 43 00 307.
Abstract and Machine Translation of French Patent No. FR 2 915 873.
U.S. Appl. No. 13/241,629.
Australian Examiner's Report dated May 28, 2015 for Application No. AU 2011305395, 4 pages.
Chinese First Office Action dated Dec. 8, 2014 for Application No. CN 2011800460565, 9 pages.
Chinese Second Office Action dated Sep. 1, 2015 for Application No. CN 2011800460565, 16 pages.
Chinese Third Office Action dated Feb. 1, 2016 for Application No. CN 2011800460565, 3 pages.
Chinese First Office Action dated Dec. 29, 2014 for Application No. CN 2011800460599, 15 pages.
Chinese Second Office Action dated Sep. 8, 2015 for Application No. CN 2011800460599, 5 pages.
Chinese Third Office Action dated Mar. 22, 2016 for Application No. CN 2011800460599, 5 pages.
Chinese First Office Action dated Feb. 4, 2015 for Application No. CN 2011800460654, 11 pages.
Chinese Second Office Action dated Oct. 10, 2015 for Application No. CN 2011800460654, 6 pages.
Japanese Office Action, Notification of Reasons for Refusal, dated Jun. 23, 2015 for Application No. JP 2013-530302, 4 pages.
Japanese Office Action, Notification of Reasons for Refusal, dated Jun. 9, 2015 for Application No. JP 2013-530303, 5 pages.
Japanese Office Action, Notification of Reasons for Refusal, dated Jun. 23, 2015 for Application No. JP 2013-530363, 4 pages.
Japanese Office Action, Notification of Reasons for Refusal, dated Jun. 23, 2015 for Application No. JP 2013-530365, 4 pages.
Russian Office Action dated Jul. 1, 2015 for Application No. 2013118706, 5 pages.

(56) References Cited

OTHER PUBLICATIONS

U.S. Office Action, Non-Final, dated Mar. 5, 2015 for U.S. Appl. No. 13/235,648, 11 pages.
U.S. Office Action, Final, dated Oct. 1, 2015 for U.S. Appl. No. 13/235,648, 14 pages.
U.S. Office Action, Non-Final, dated Oct. 6, 2016 for U.S. Appl. No. 13/235,648, 14 pages.
U.S. Office Action, Notice of Allowance, dated Mar. 2, 2015 for U.S. Appl. No. 13/622,729, 5 pages.
U.S. Office Action, Notice of Allowance, dated Apr. 14, 2016 for U.S. Appl. No. 13/622,735, 5 pages.
International Search Report dated Jun. 13, 2012 for Application No. PCT/US2011/053016.
Chinese Office Action dated Oct. 10, 2016 for Application No. CN 201380048783.4, 7 pgs.
Chinese Office Action dated Oct. 10, 2016 for Application No. CN 201380048566.5, 11 pgs.
U.S. Appl. No. 61/386,094, filed Sep. 24, 2010.
U.S. Appl. No. 13/235,648.
U.S. Appl. No. 13/622,729.
U.S. Appl. No. 13/622,735.
Canadian Office Action dated Jun. 16, 2017 for Application No. CA 2,811,337, 6 pgs.
Canadian Office Action dated Jul. 7, 2017 for Application No. CA 2,812,146, 4 pgs.

* cited by examiner

CONTROL FEATURES FOR ARTICULATING SURGICAL DEVICE

PRIORITY

This application claims priority to U.S. Provisional Application Ser. No. 61/386,094, filed Sep. 24, 2010, entitled "Articulating Surgical Device," the disclosure of which is incorporated by reference herein.

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. Pat. App. No. 13/151,481, entitled "Motor Driven Electrosurgical Device with Mechanical and Electrical Feedback," filed Jun. 2, 2011, now U.S. Pat. No. 9,161,803, issued Oct. 20, 2015, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
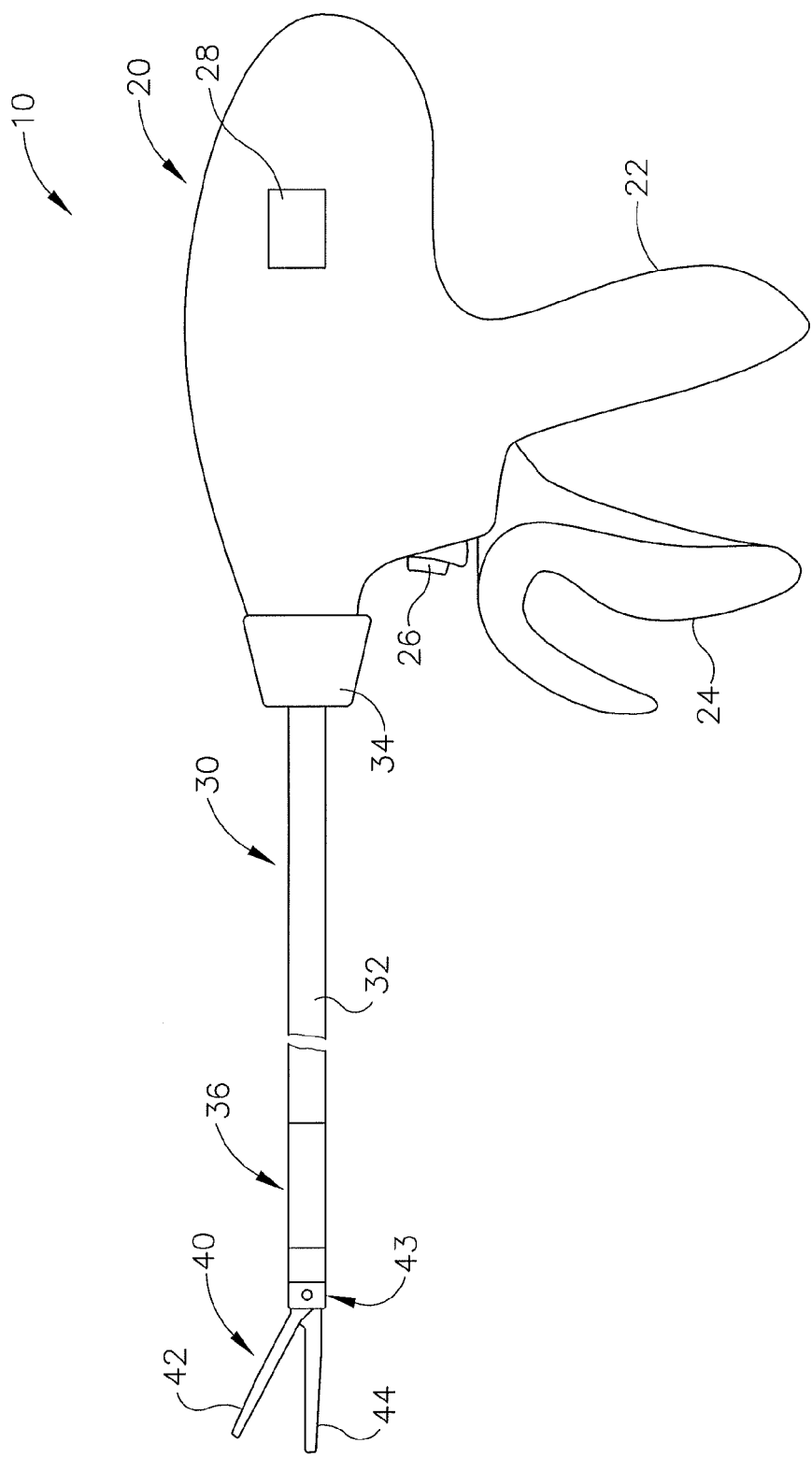
FIG. 1 depicts a side elevational view of an exemplary electrosurgical medical device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218; and/or U.S. Pat. App. No. 13/151,481, now published as U.S. Pub. No. 2012/0116379, now U.S. Pat. No. 9,161,803, issued Oct. 20 2015. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL®Tissue Sealing Device by Ethicon Endo-Surgery, Inc., of Cincinnati, OH. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL®Tissue Sealing Device by Ethicon Endo-Surgery, Inc., of Cincinnati, OH, and the following teachings relating to electrosurgical instrument (10), there is no intent for any of the description herein to be presumed as admitted prior art. Several teachings below will in fact go beyond the scope of the teachings of the references cited herein and the ENSEAL®Tissue Sealing Device by Ethicon Endo-Surgery, Inc., of Cincinnati, OH.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. It should be understood that pistol grip (22), trigger (24), and button (26) may be modified, substituted, supplemented, etc. in any suitable way, and that the descriptions of such components herein are merely illustrative. Articulation control (28) of the present example is operable to selectively control articulation section (36) of shaft (30), which will be described in greater detail below. Various examples of forms that articulation control (28) may take will also be described in greater detail below, while further examples will be apparent to those of ordinary skill in the art in view of the teachings herein.

Shaft (30) of the present example includes an outer sheath (32) and an articulation section (36). Articulation section (36) is operable to selectively position end effector (40) at various angles relative to the longitudinal axis defined by sheath (32). Various examples of forms that articulation section (36) and other components of shaft (30) may take will be described in greater detail below, while further examples will be apparent to those of ordinary skill in the art in view of the teachings herein. For instance, it should be understood that various components that are operable to actuate articulation section (36) may extend through the interior of sheath (32). In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

B. Exemplary End Effector

End effector (40) of the present example comprises a first jaw (42) and a second jaw (44). In the present example, second jaw (44) is substantially fixed relative to shaft (30); while first jaw (42) pivots relative to shaft (30), toward and away from second jaw (42). In some versions, actuators such as rods or cables, etc., may extend through sheath (32) and be joined with first jaw (42) at a pivotal coupling (43), such that longitudinal movement of the actuator rods/cables/etc. through shaft (30) provides pivoting of first jaw (42) relative to shaft (30) and relative to second jaw (44). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
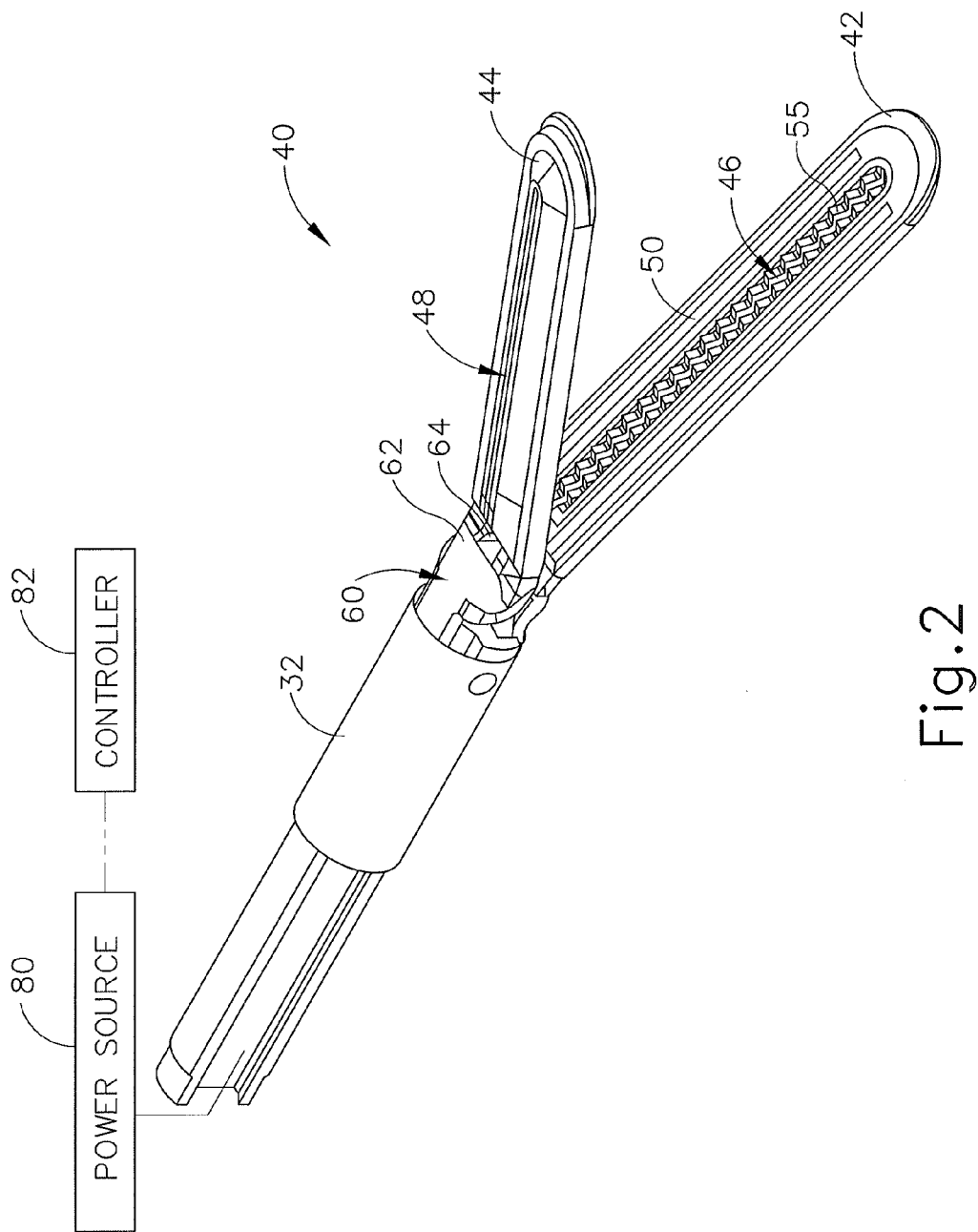
FIG. 2 depicts a perspective view of the end effector of the device of FIG. 1, in an open configuration.
Figure 3:
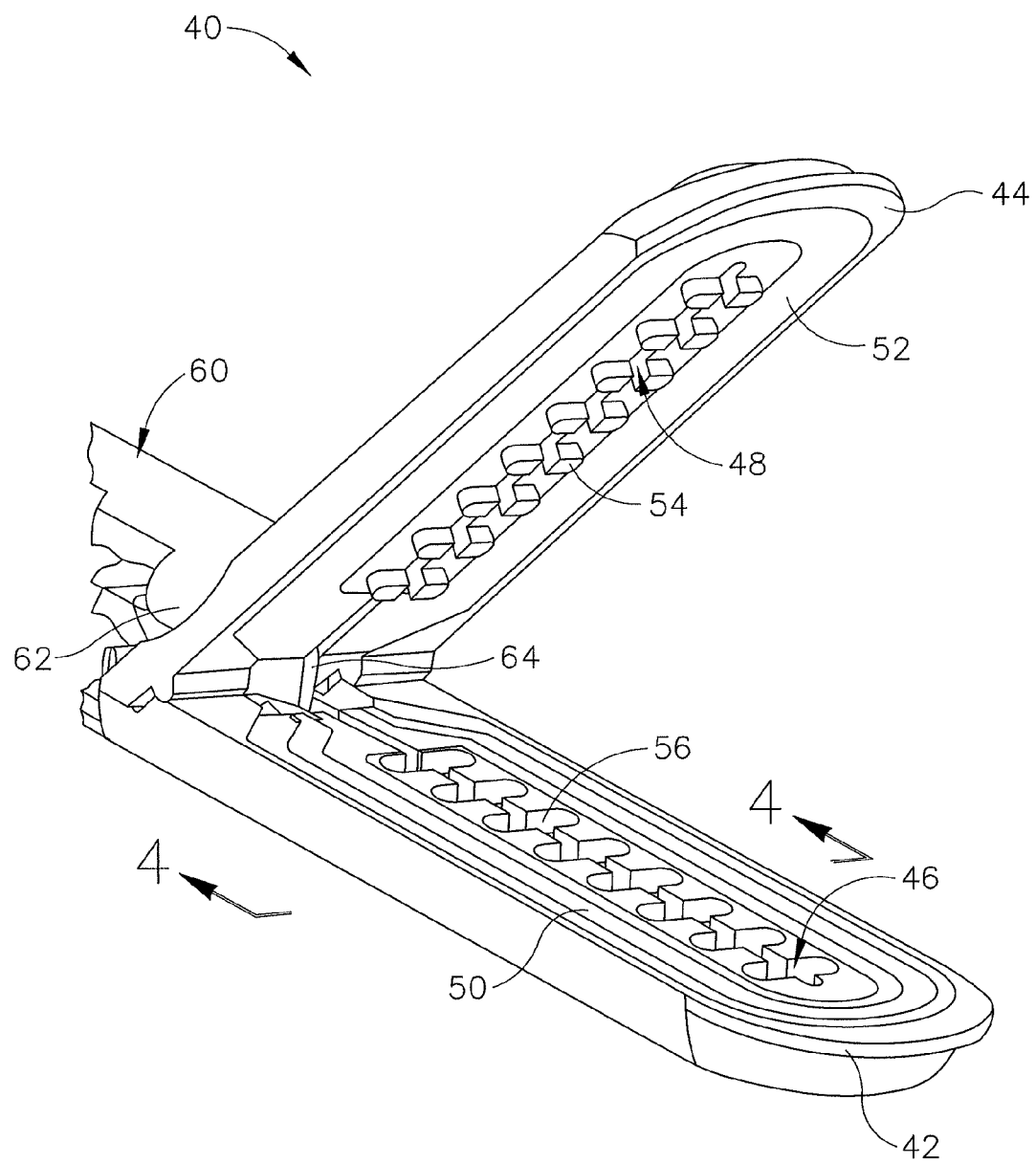
FIG. 3 depicts another perspective view of the end effector of the device of FIG. 1, in an open configuration.
Figure 4:
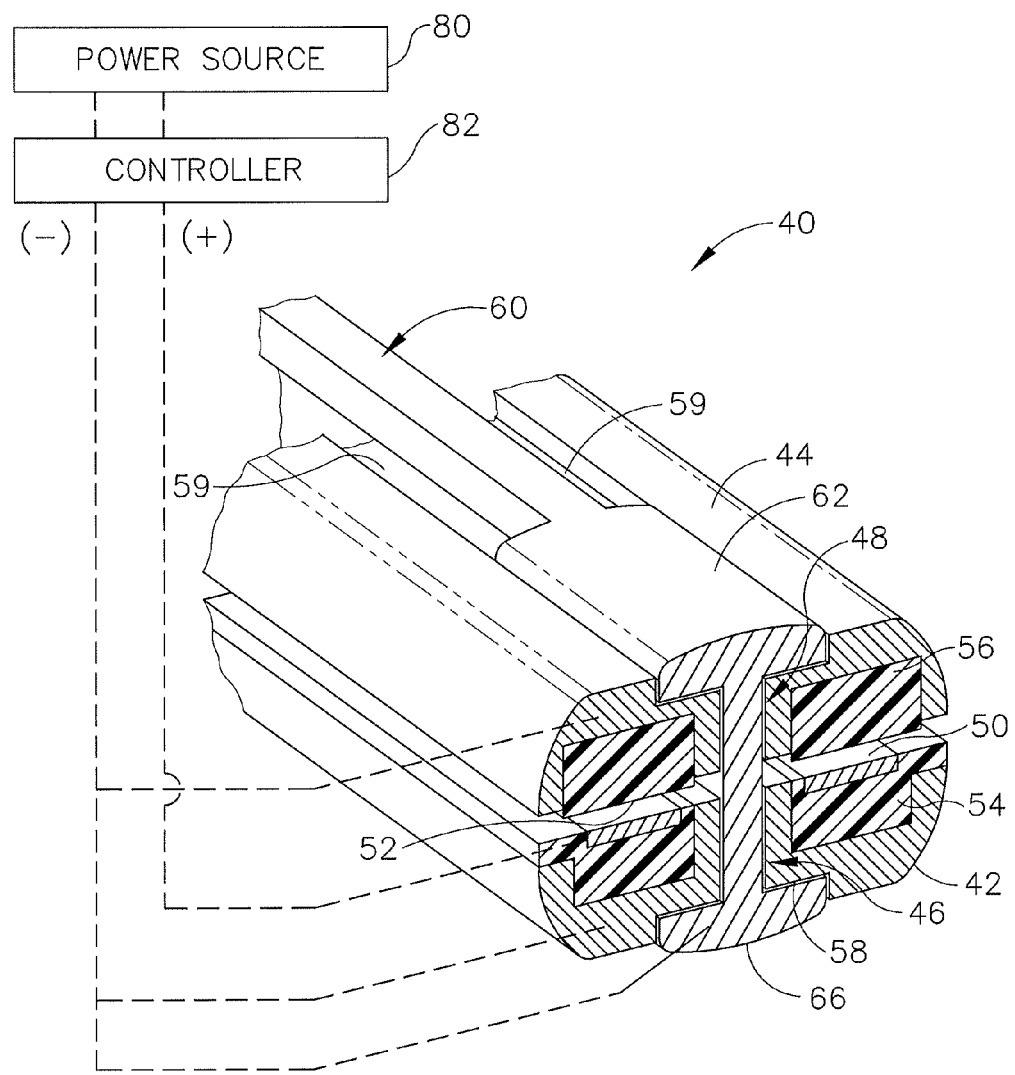
FIG. 4 depicts a cross-sectional end view of the end effector of FIG. 2, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (58) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from the tissue captured between jaws (42, 44). Of course, any other suitable staging may be provided.

In the present example, flange (62) is configured to cam against a ramp feature at the proximal end of jaw (44) to open jaw (42) when firing beam (60) is retracted to a proximal position and to hold jaw (42) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood veseel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (44) toward jaw (44) when firing beam (60) is actuated distally by squeezing trigger (24) toward pistol grip (22).

With tissue layers captured between jaws (42, 44) firing beam (60) continues to advance distally by the user squeezing trigger (24) toward pistol grip (22). As firing beam (60) advances distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52).

While several of the teachings below are described as variations to electrosurgical instrument (10), it should be understood that various teachings below may also be incorporated into various other types of devices. By way of example only, in addition to being readily incorporated into electrosurgical instrument (10), various teachings below may be readily incorporated into the devices taught in any of the references cited herein, other types of electrosurgical devices, surgical staplers, surgical clip appliers, and tissue graspers, among various other devices. Other suitable devices into which the following teachings may be incorporated will be apparent to those of ordinary skill in the art in view of the teachings herein.

II. Exemplary Articulation Joint Configurations

Articulation section (36) of shaft (30) may take a variety of forms. By way of example only, articulation section (36) may be configured in accordance with one or more teachings of U.S. patent application Ser. No. 13/235,660, entitled "Articulation Joint Features for Articulating Surgical Device," filed Sep. 19, 2011, now U.S. Pat. No. 9,402,682, issued Aug. 2, 2016, the disclosure of which is incorporated by reference herein. As another merely illustrative example, articulation section (36) may be configured in accordance with one or more teachings of U.S. patent application Ser. No. 13/235,683, entitled "Articulation Joint Features for Articulating Surgical Device," filed on even date herewith September 19, 2011, published Mar. 29, 2012 as U.S. Pub. No. 2012/0078248, now U.S. Pat. No. 9,220,559, issued Dec. 29, 2015, the disclosure of which is incorporated by reference herein. Furthermore, articulation section may be configured in accordance with the teachings of at least one other of the references cited herein. Various other suitable forms that articulation section (36) may take will be apparent to those of ordinary skill in the art in view of the teachings herein.

III. Exemplary Articulation Control Configurations

As noted above, some versions of handpiece (20) include an articulation control (28), which is operable to control articulation section (36) of shaft (30) to thereby selectively position end effector (40) at various angles relative to the longitudinal axis defined by sheath (32). Several examples of forms that articulation control (28) and other components of handpiece (20) may take will be described in greater detail below, while further examples will be apparent to those of ordinary skill in the art in view of the teachings herein. By way of example only, some merely illustrative alternative examples of articulation control (28) are disclosed in U.S. patent application Ser. No. 13/235,648, entitled "Control Features for Articulating Surgical Device," filed Sep. 19, 2011, published as U.S. Pub. No. 2012/0078244 on Mar. 29, 2012, the disclosure of which is incorporated by reference herein.

A. Exemplary Articulation Control with Perpendicular Rotary Knob

Figure 5:
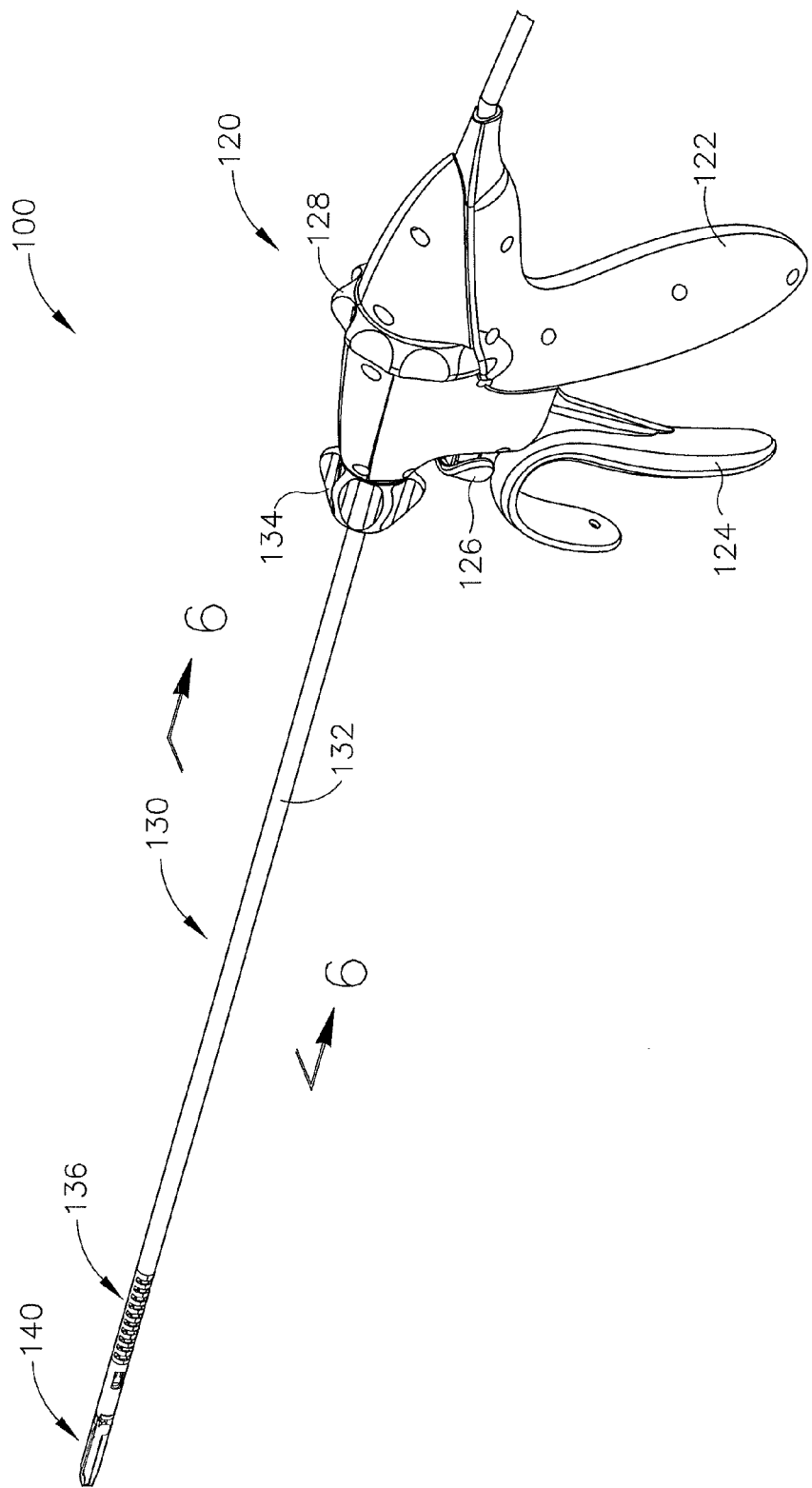
FIG. 5 depicts a perspective view of another exemplary electrosurgical medical device, with an articulation control knob.

FIG. 5 depicts an exemplary electrosurgical instrument (100) that includes a handpiece (120), a shaft (130) extending distally from handpiece (120), and an end effector (140) disposed at a distal end of shaft (130). Handpiece (120) of the present example includes a pistol grip (122), a pivoting trigger (124), an activation button (126), and a rotary articulation knob (128). Trigger (124) is pivotable toward and away from pistol grip (122) to selectively actuate end effector (140) as described above and as described in one or more reference cited herein. Activation button (126) is operable to selectively activate RF circuitry that is in communication with end effector (140), as also described above and as described in one or more reference cited herein. In some versions, activation button (126) also serves as a mechanical lockout against trigger (124), such that trigger (124) cannot be fully actuated unless button (126) is being pressed simultaneously. Examples of how such a lockout may be provided are disclosed in one or more of the references cited herein. It should be understood that pistol grip (122), trigger (124), and button (126) may be modified, substituted, supplemented, etc. in any suitable way, and that the descriptions of such components herein are merely illustrative. Articulation knob (128) of the present example is operable to selectively control articulation section (136) of shaft (130), as will be described in greater detail below.

Shaft (130) of the present example includes an outer sheath (132), an articulation section (136) at the distal end of sheath (132), and a cutting member driver tube (138) that is slidably and coaxially disposed within sheath (132). Cutting member driver tube (138) is secured to a driver block (139), which is further secured to a cutting member (146) of end effector (140). Cutting member driver tube (138) is movable longitudinally to drive driver block (139) longitudinally, to thereby move cutting member (146) longitudinally. Cutting member (146) is essentially equivalent to firing beam (60) described above. The proximal portion (148) of end effector (140) includes an insert (not shown) that defines a channel containing the part of cutting member (146) that extends through proximal portion (148). This channel is configured to permit cutting member (146) to readily translate relative to the insert, while also preventing cutting member (146) from buckling within the insert when cutting member (146) encounters a load during distal advancement of cutting member (146).

Figure 13:
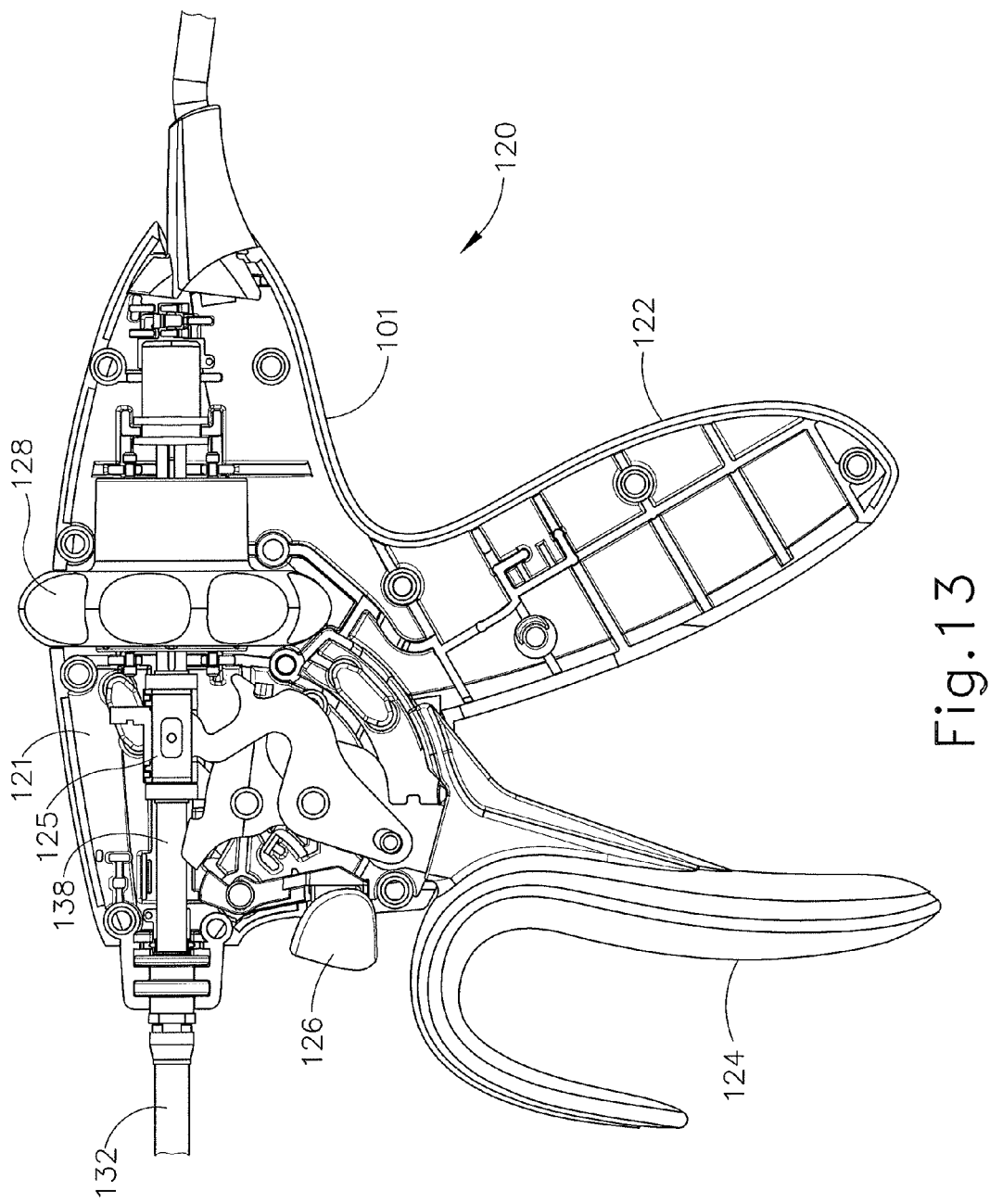
FIG. 13 depicts a side elevational view of the handle assembly of the device of FIG. 5, with a housing half removed.

In the present example, driver tube (138) is advanced distally by squeezing trigger (124) toward pistol grip (122); while driver tube (138) is retracted proximally by releasing trigger (124) and/or by actively moving trigger (124) away from pistol grip (122). As shown in FIG. 13, a yoke (125) couples trigger (124) with driver tube (138). Of course, cutting member (146) may be moved in any other suitable fashion. Articulation section (136) of the present example is operable to selectively position end effector (140) at various angles relative to the longitudinal axis defined by sheath (132). Various examples of forms that articulation section (136) and other components of shaft (130) may take are described in various references cited herein, while further examples will be apparent to those of ordinary skill in the art in view of the teachings herein. Similarly, end effector (140) may be configured in accordance with end effector (40) described above, in accordance with the teachings of various references cited herein, and/or in any other suitable way as will be apparent to those of ordinary skill in the art in view of the teachings herein.

In some versions, shaft (130) is also rotatable about the longitudinal axis defined by sheath (132), relative to handpiece (120), via a knob (134). Such rotation may provide rotation of end effector (140) and shaft (130) unitarily. In some other versions, knob (134) is operable to rotate end effector (140) without rotating any portion of shaft (130) that is proximal of articulation section (136). As another merely illustrative example, electrosurgical instrument (100) may include one rotation control that provides rotatability of shaft (130) and end effector (140) as a single unit; and another rotation control that provides rotatability of end effector (140) without rotating any portion of shaft (130) that is proximal of section (136). Other suitable rotation schemes will be apparent to those of ordinary skill in the art in view of the teachings herein. Of course, rotatable features may simply be omitted if desired. In any versions of a device that provide rotation of a shaft (130) and/or end effector (140), a rotation knob (134) and/or shaft (130) and/or end effector (140) may include one or more markings facilitating visual identification of the rotational position. For instance, a user may correlate a marking on a rotation knob (134) with a corresponding marking on a shaft (130) and/or end effector (140) to better understand the orientation of such components with respect to the patient and instrument (100).

Figure 6:
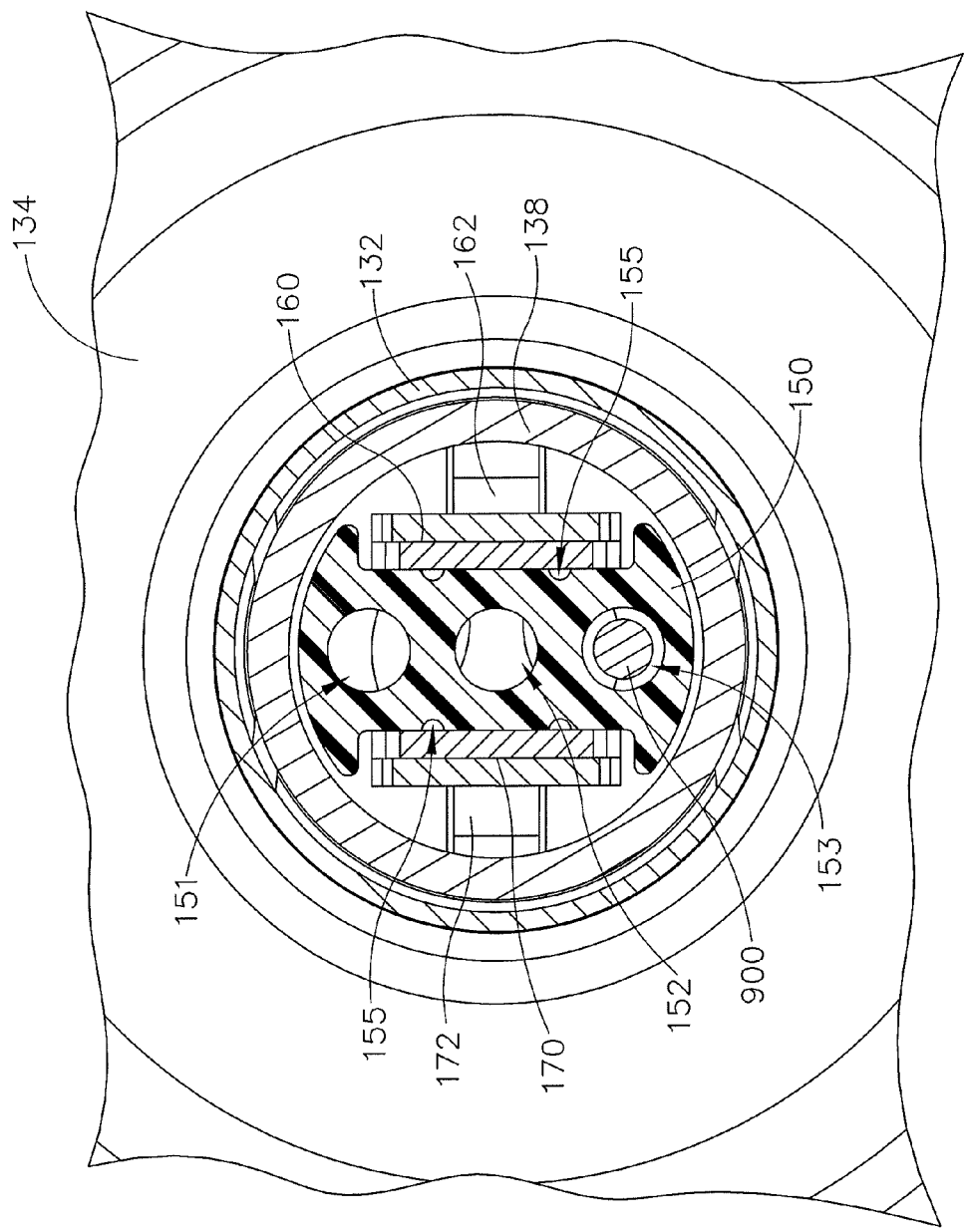
FIG. 6 depicts a cross-sectional end view of a shaft assembly of the device of FIG. 5, taken along line 6-6 of FIG. 5.

FIGS. 6-12 show various components of shaft (130) that provide control for articulation of articulation section (136). In particular, these components include a separator (150), a first articulation band (160) with an associated drive member (162), and a second articulation band (170) with an associated drive member (172). As best seen in FIG. 6, separator (150) includes an upper lumen (151), a middle lumen (152), and a lower lumen (153). Separator (150) also includes side recesses (154), a distal projection (156), and a gap (158). Separator (150) is disposed within cutting member driver tube (138) and maintains a fixed longitudinal position during operation of instrument (100). Thus, separator (150) and outer sheath (132) remain stationary relative to each other and relative to handpiece (120); while cutting member driver tube (138) reciprocates relative to separator (150), outer sheath (132), and handpiece (120). Distal projection (156) is configured to permit translation of driver block (139) substantially free from interference by distal projection (156) or by any other portion of separator (150).

In the present example, separator (150) is formed as two pieces arranged in an end-to-end configuration, with a distal projection from the proximal piece helping to define gap (158). Of course, separator (150) may alternatively be formed as a single piece or any other suitable number of pieces. By way of example only, gap (158) may be formed as a cutout from a single piece of material.

As will be described in greater detail below, a wire (900) extends through separator (150) to provide electrical communication to end effector (140). In particular, wire (900) extends through middle lumen (152) from the proximal end of separator (150) until wire (900) reaches gap (158). At gap (158), wire (900) transitions down to lower lumen (153), and extends through lower lumen (153) until reaching the distal end of separator (150). Wire (900) then extends across articulation section (136) to end effector (140). Wire (900) is thus operable to communicate power from a power source to end effector (140) in accordance with the teachings herein and in accordance with the teachings of various references cited herein. Distal projection (156) protects wire (900) from driver block (139), such that driver block (139) is unable to contact wire (900) regardless of the longitudinal position of driver block (139) along distal projection (156).

Figure 7:
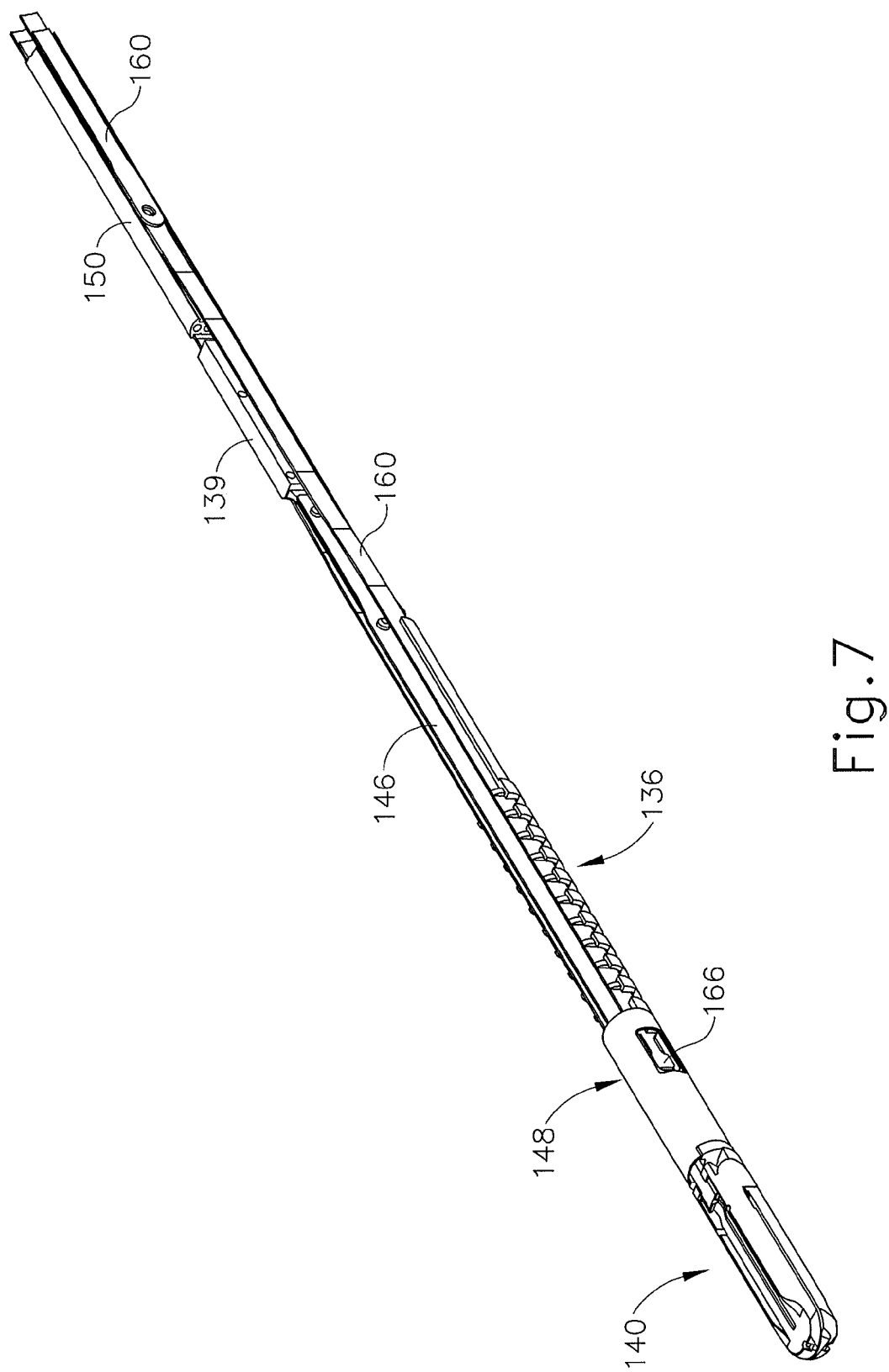
FIG. 7 depicts a perspective view of components of the shaft assembly and end effector of the device of FIG. 5.
Figure 8:
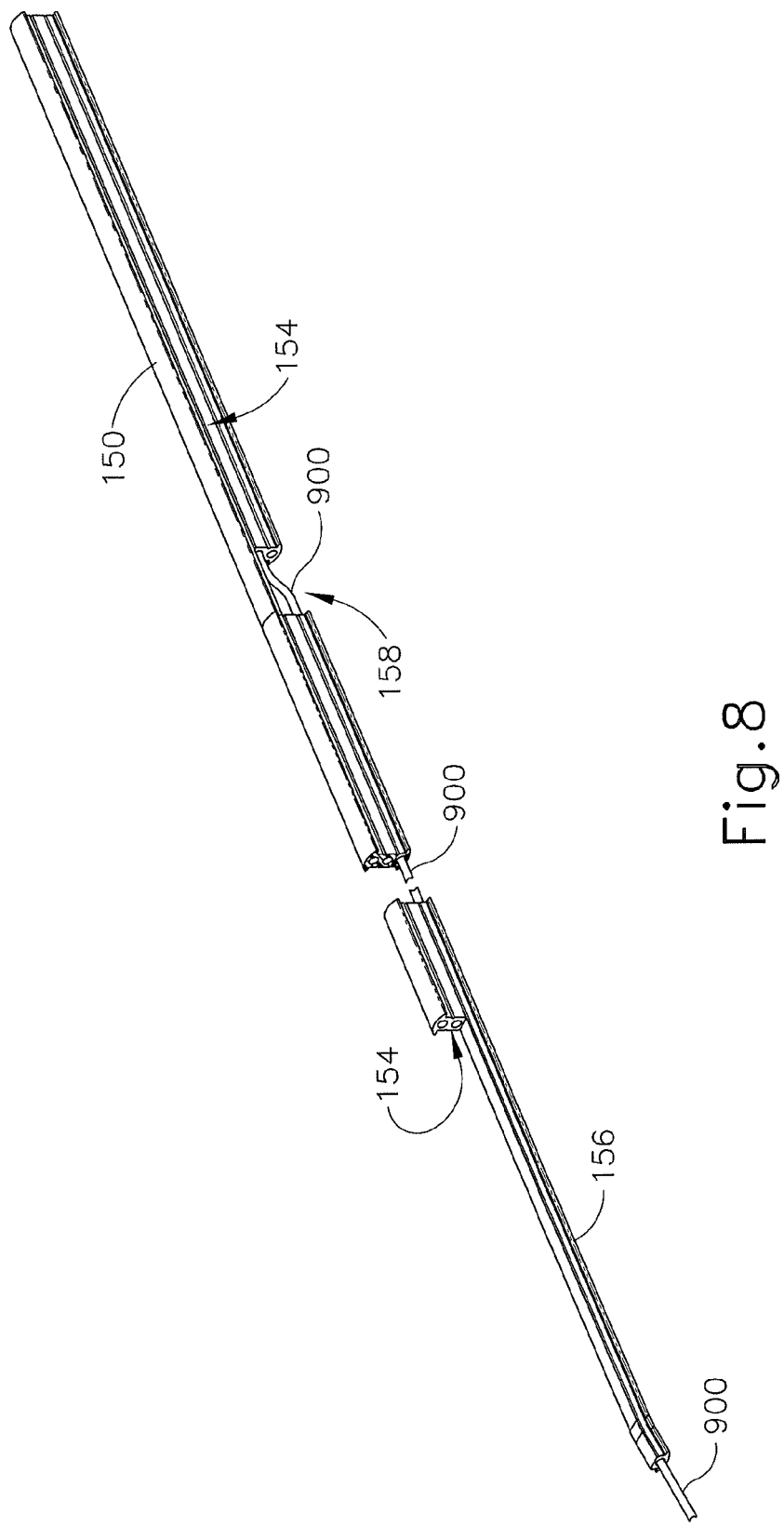
FIG. 8 depicts a perspective view of a support member of the shaft assembly of the device of FIG. 5.

First articulation band (160) is slidably disposed in one side recess (154) of separator (150) while second articulation band (170) is slidably disposed in the other side recess (154) of separator (150). Referring back to FIG. 6, side recesses (154) include longitudinally extending grooves (155) that are configured to reduce the contact surface area with articulation bands (160, 170), thereby reducing friction between separator (150) and articulation bands (160, 170). Separator (150) may also be formed of a low friction material and/or include a surface treatment to reduce friction. Articulation bands (160, 170) both extend longitudinally along the entire length of shaft (130), including through articulation section (136). As shown in FIG. 7, the distal end (166) of first articulation band (160) is secured to one side of the proximal portion (148) of end effector (140) at an anchor point. The distal end (176) of second articulation band (170) is secured to the other side of proximal portion (148) of end effector (140) at an anchor point. As will be described in greater detail below, rotary articulation knob (128) is operable to selectively advance one articulation band (160, 170) distally while simultaneously retracting the other articulation band (160, 170) proximally, and vice-versa. It should be understood that this opposing translation will cause articulation section (136) to bend, thereby articulating end effector (140). In particular, end effector (140) will deflect toward whichever articulation band (160, 170) is being retracted proximally; and away from whichever articulation band (160, 170) is being advanced distally.

Figure 9:
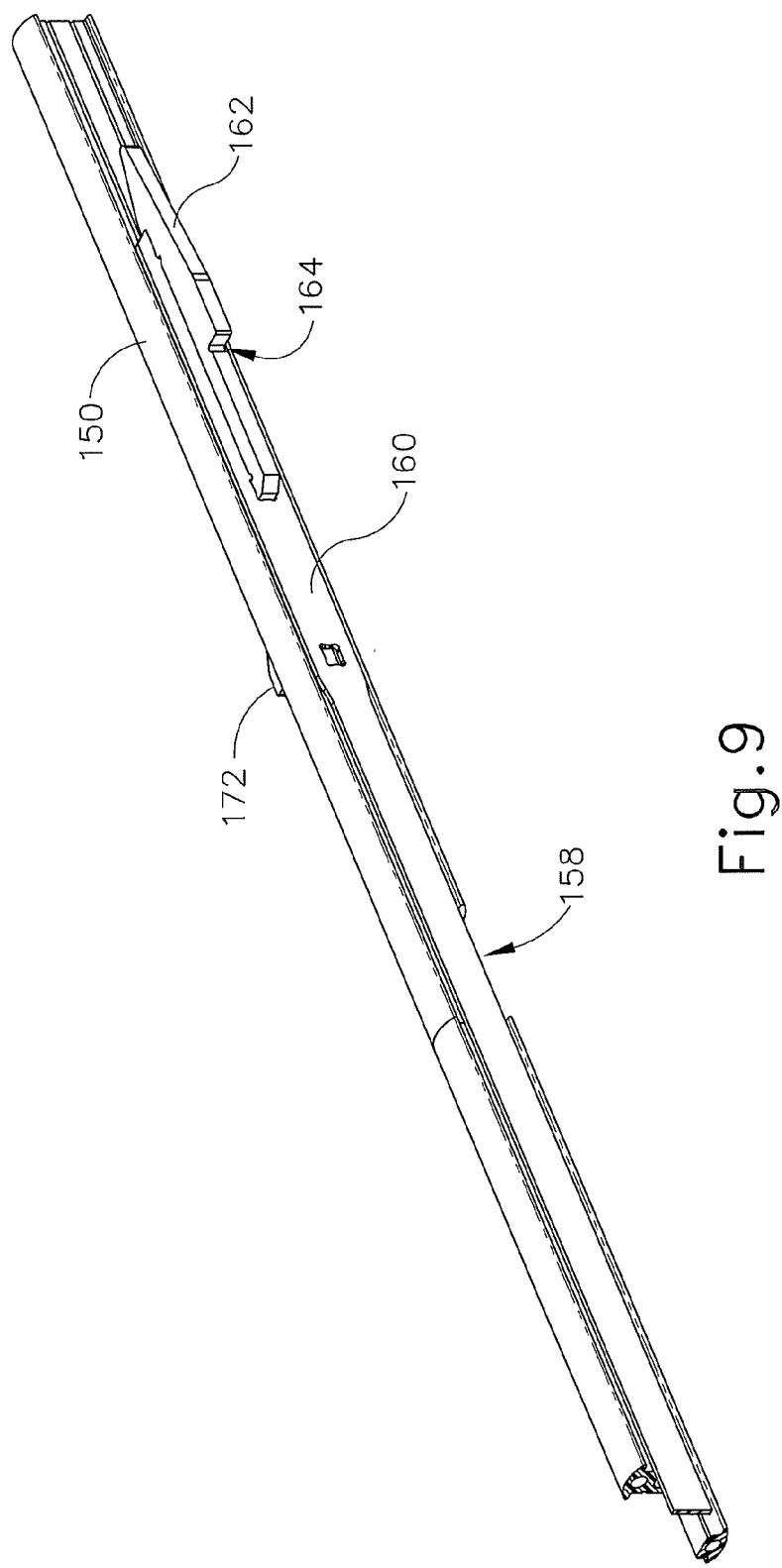
FIG. 9 depicts a partial perspective view of articulation control components of the device of FIG. 5, along one side of the support member.
Figure 10:
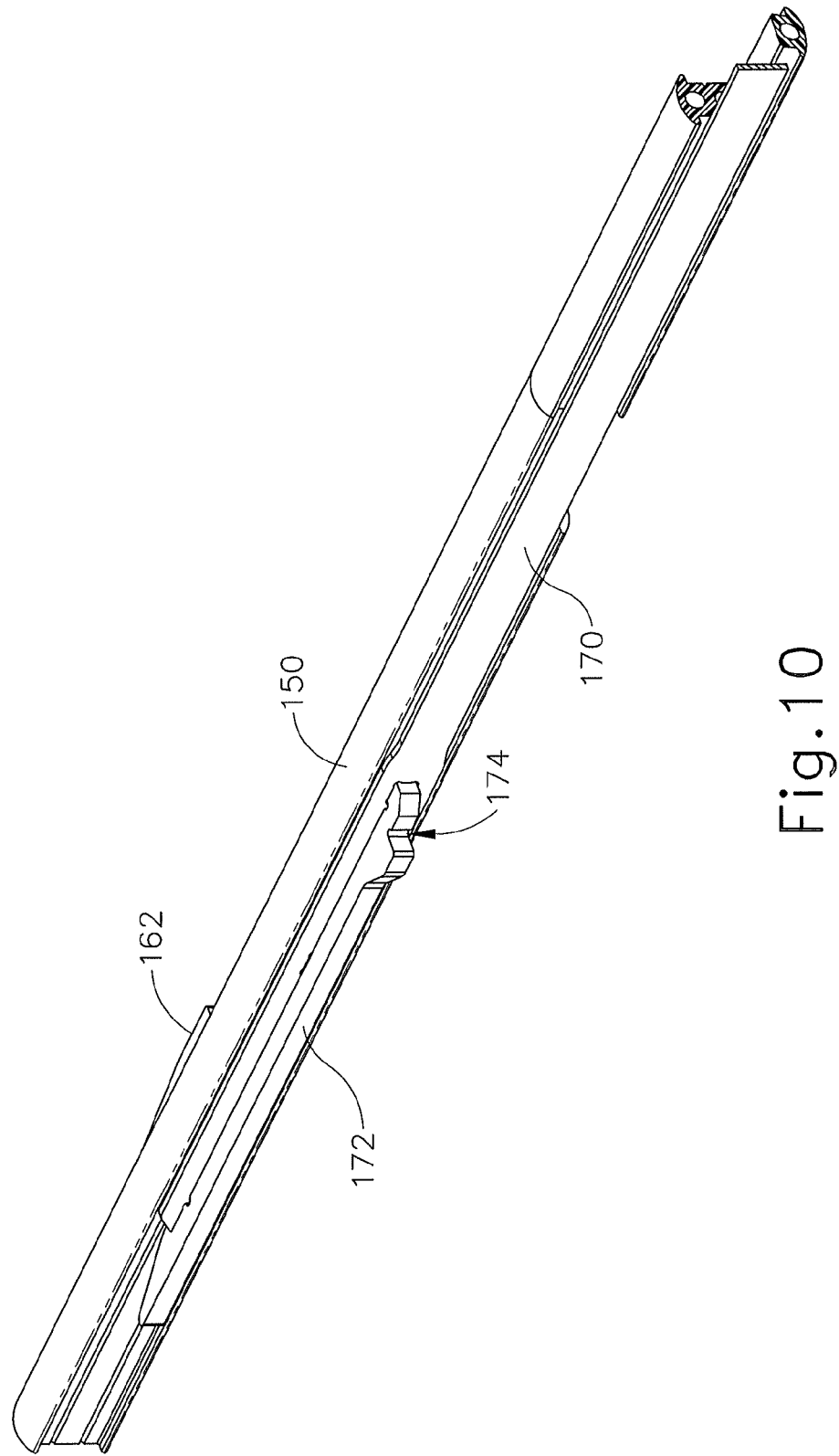
FIG. 10 depicts a partial perspective view of articulation control components of the device of FIG. 5, along another side of the support member.
Figure 11:
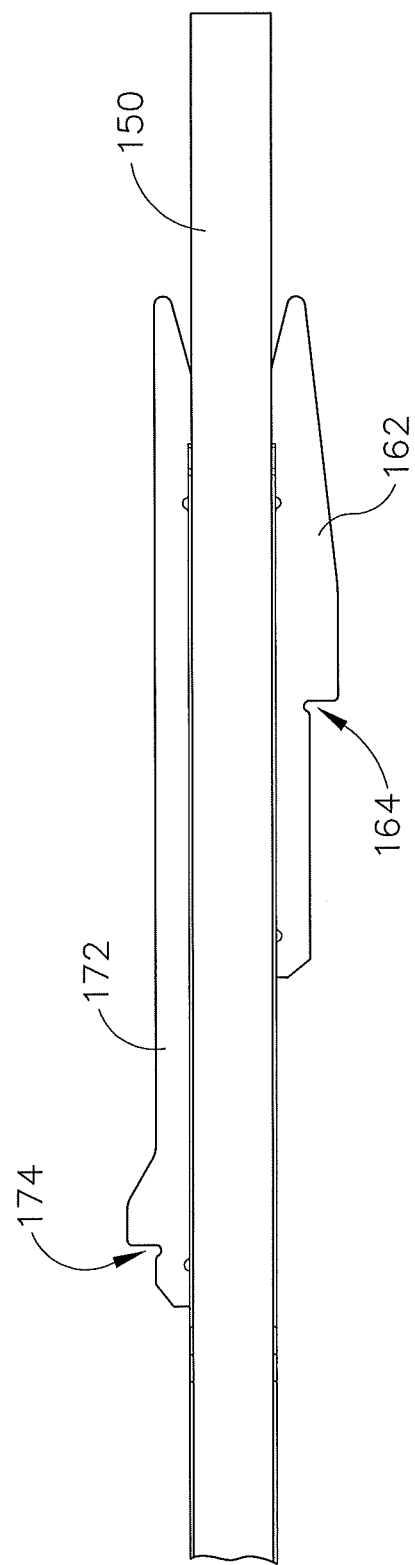
FIG. 11 depicts a top plan view of the articulation control components of FIGS. 9-10.
Figure 12:
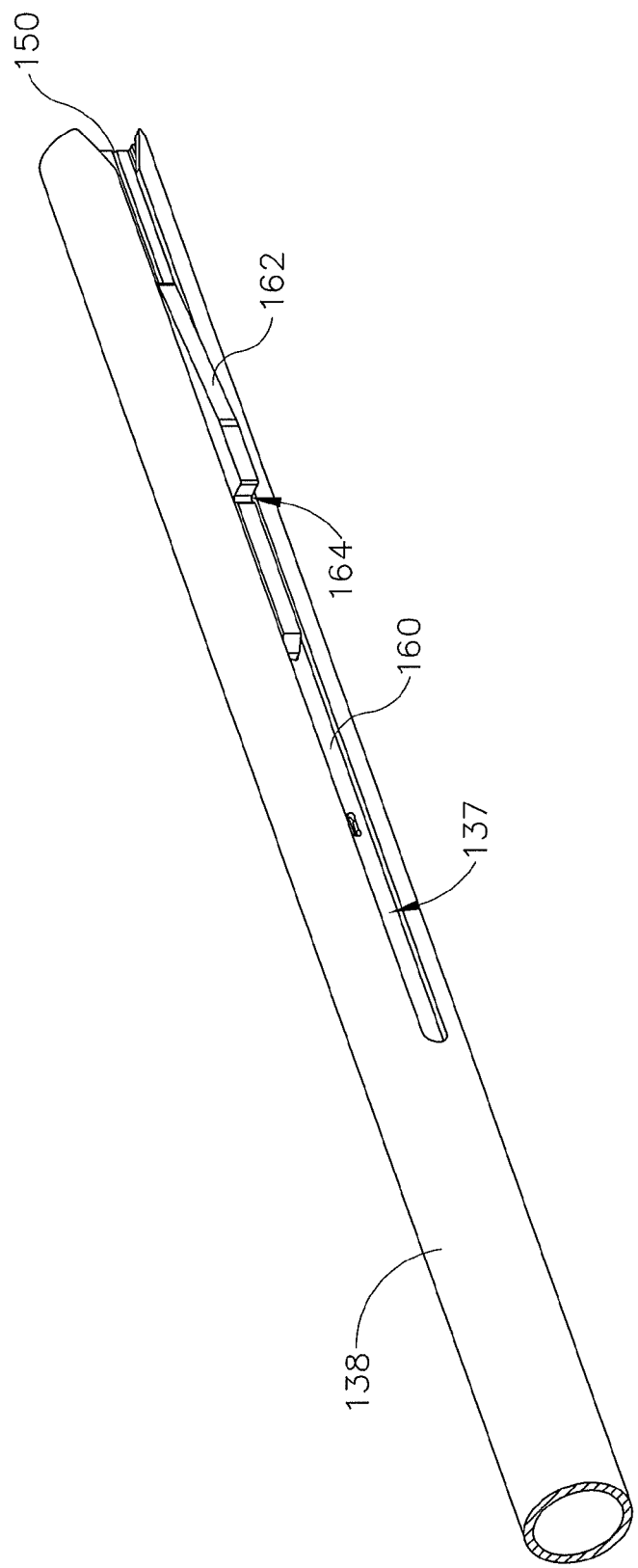
FIG. 12 depicts a partial perspective view of the articulation control components of FIG. 9 surrounded by a sheath.

As best seen in FIG. 9, drive member (162) is unitarily secured to articulation band (160) and includes a notch (164) extending laterally inwardly. As best seen in FIG. 10, drive member (172) is unitarily secured to articulation band (170) and includes a notch (174) extending laterally inwardly. As best seen in FIG. 11, drive members (162, 164) are spaced and configured such that notches (164, 174) are at different longitudinal positions along the length of separator (150). As best seen in FIG. 12, the proximal portion of cutting member driver tube (138) includes longitudinally extending slots (137). Drive members (162, 172) are slidably disposed in slots (137) and notches (164, 174) are radially positioned outside the outer circumference of cutting member driver tube (138). Slots (137) are configured to enable free translation of cutting member driver tube (138) relative to drive members (162, 172), to thus enable free actuation of cutting member (164) regardless of the articulation state of articulation section (136). In other words, slots (137) are configured to enable free translation of drive members (162, 172) relative to cutting member driver tube (138), to thus enable free articulation of articulation section (136) regardless of the longitudinal position of cutting member (164).

Figure 14:
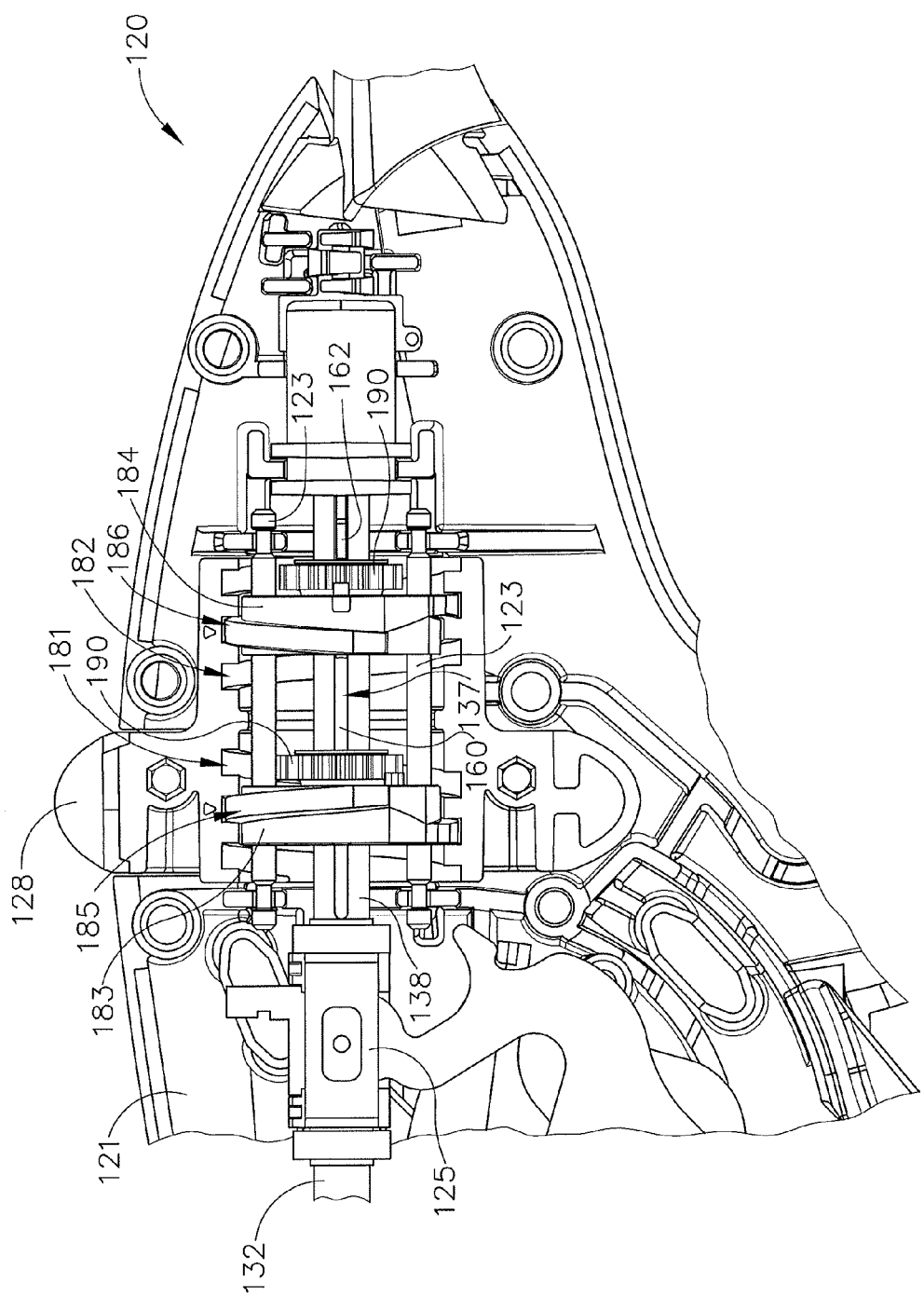
FIG. 14 depicts a side elevational view of articulation control components of the handle assembly of FIG. 13, with half of an articulation control knob body removed.

As shown in FIGS. 13-14, rotary articulation knob (128) is coaxially positioned about the proximal portion of driver tube (138) and encompasses drive members (162, 172). Articulation knob (128) is oriented perpendicular to the longitudinal axis defined by shaft (130) and is rotatable about the longitudinal axis defined by shaft (130). As will be described in greater detail below, such rotation of articulation knob (128) will cause opposing translation of drive members (162, 172), with the directions of such opposing translations depending on the direction in which articulation knob (128) is rotated, such that rotation of articulation knob (128) will articulate end effector (140). As shown in FIGS. 14, articulation knob (128) includes a first internal threading (180) and a second internal threading (182). Threadings (181, 182) have opposing pitch angles or orientations in this example.

Figure 15:
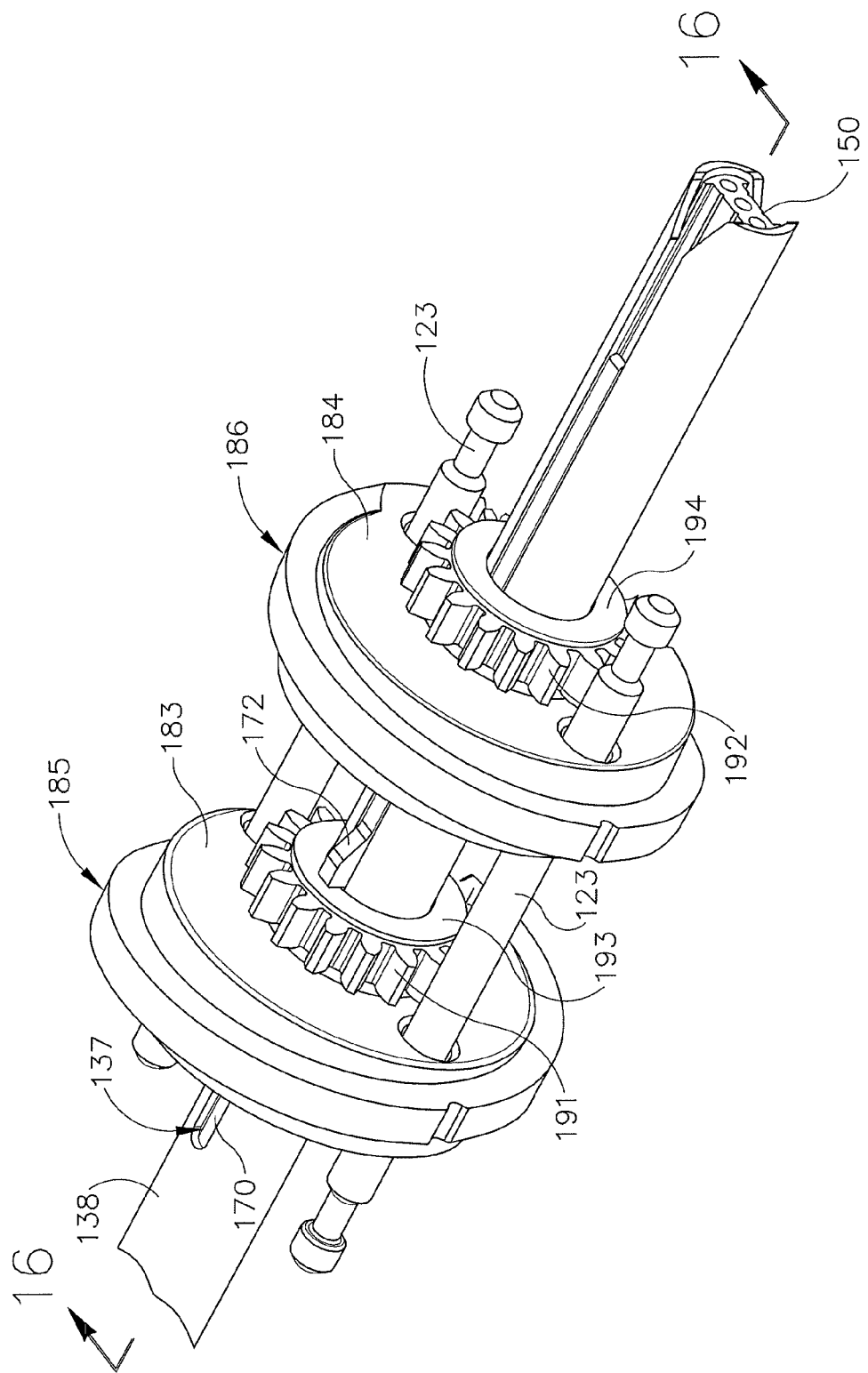
FIG. 15 depicts a perspective view of articulation control components of the handle assembly of FIG. 13, coupled with the articulation control components of FIGS. 9-10.

As best seen in FIGS. 14-15, a first lead screw (183) and a second lead screw (184) are slidably disposed along a pair of pins (123), which are secured to housing (121). Thus, lead screws (183, 184) are operable to translate within housing (121) but are prevented from rotating within housing (121). First lead screw (183) includes exterior threading (185) that is engaged with threading (181) of articulation knob (128); while second lead screw (184) includes exterior threading (186) that is engaged with threading (182) of articulation knob (128). The pitch angle of threading (185) complements the pitch angle of threading (181); while the pitch angle of threading (186) complements the pitch angle of threading (182). It should therefore be understood that, due to the opposing pitch angles, rotation of knob (128) in a first direction will drive lead screw (183) distally while simultaneously driving lead screw (184) proximally; and rotation of knob in a second direction will drive lead screw (183) proximally while simultaneously driving lead screw (184) distally.

The angles of threading (181, 182, 185, 186) are also configured such that articulation section (136) will be effectively locked in any given articulated position, such that transverse loads on end effector (140) will generally not bend articulation section (136), due to friction between threading (181, 182, 185, 186). In other words, articulation section (136) will only change its configuration when knob (128) is rotated. While the angles of threading may substantially prevent bending of articulation section (136) in response to transverse loads on end effector (140), the angles may still provide ready rotation of articulation knob (128) to translate lead screws (183, 184). By way of example only, the angles of threading (181, 182, 185, 186) may be approximately +/−2 degrees or approximately +/−3 degrees. Other suitable angles will be apparent to those of ordinary skill in the art in view of the teachings herein. It should also be understood that threading (181, 182, 185, 186) may have a square or rectangular cross-section or any other suitable configuration.

Figure 16:
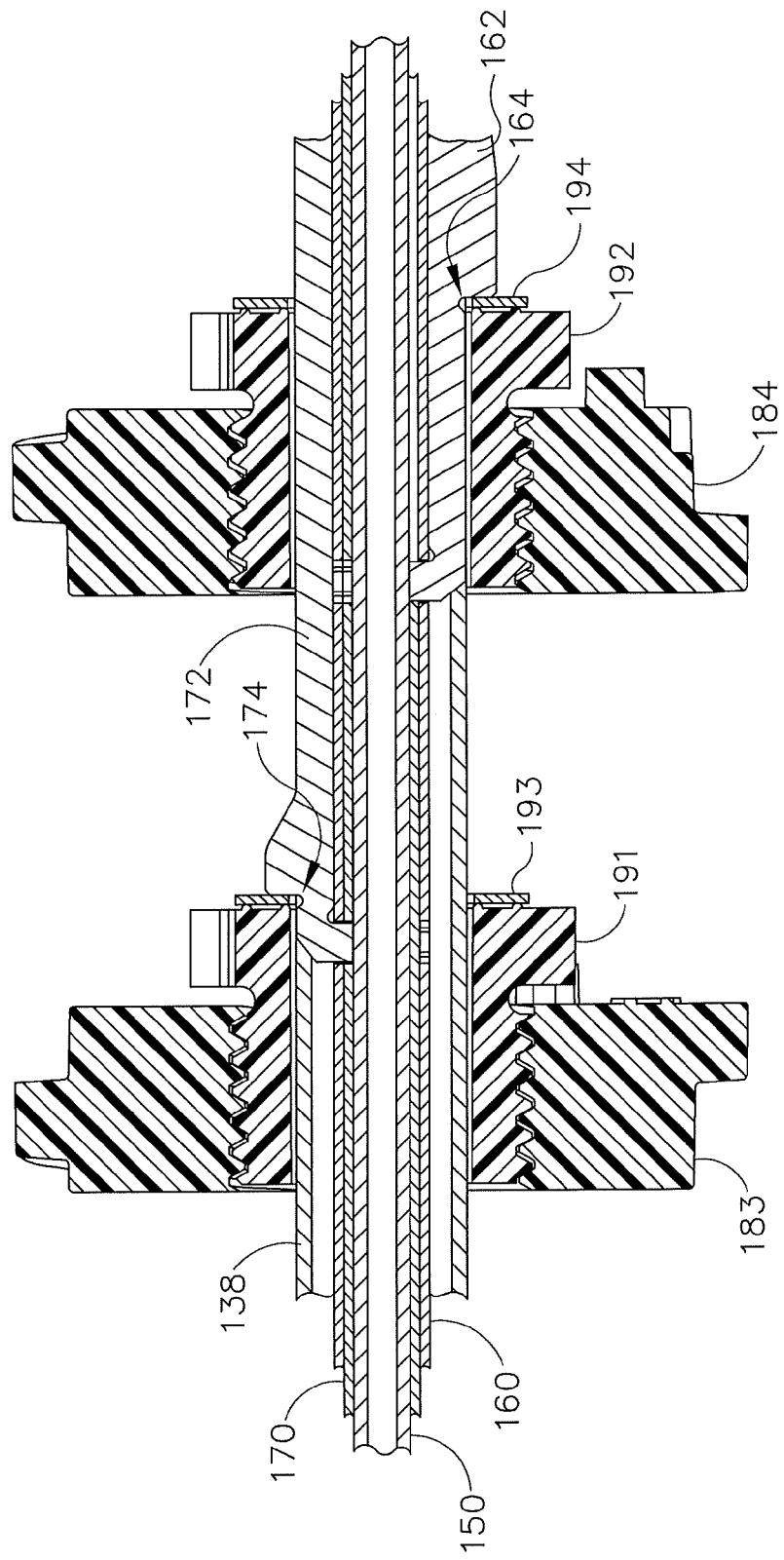
FIG. 16 depicts a side cross-sectional view of the articulation control components of FIG. 15, taken along line 16-16 of FIG. 15.

As best seen in FIGS. 15-16, a first tensioner gear (191) is threadably engaged with first lead screw (183); while a second tensioner gear (192) is threadably engaged with second lead screw (184). Thus, the longitudinal position of first tensioner gear (191) relative to first lead screw (183) may be adjusted by rotating first tensioner gear (191) relative to first lead screw (183); while the longitudinal position of second tensioner gear (192) relative to second lead screw (184) may be adjusted by rotating second tensioner gear (192) relative to second lead screw (184). Otherwise, first tensioner gear (191) will translate unitarily with first lead screw (183); while second tensioner gear (192) will translate unitarily with second lead screw (184).

First tensioner gear (191) is also engaged with a washer (193), which is further engaged with notch (174) of drive member (172). The engagement between washer (193) and drive member (172) is such that washer (193) and drive member (172) will translate together. In some versions, washer (193) is secured to tensioner gear (191) in such a manner that tensioner gear (191) both pulls washer (193) distally and pushes washer (193) proximally. Thus, in some such versions, first lead screw (183) is operable to both push articulation band (170) distally and pull articulation band (170) proximally, depending on which direction knob (128) is rotated. In the present example, however, tensioner gear (191) merely abuts washer (193), such that tensioner gear (191) is operable to push washer (193) proximally but cannot pull washer (193) distally. Thus, in the present example, first lead screw (183) is operable to pull articulation band (170) proximally but cannot actively push articulation band (170) distally. Instead, first lead screw (183) may simply pull tensioner gear (191) distally to enable articulation band (170), drive member (172), and washer (193) to be driven distally in response to proximal retraction of articulation band (160) as communicated through articulation section (136). Other suitable relationships will be apparent to those of ordinary skill in the art in view of the teachings herein. It should also be understood that drive member (172) and/or washer (193) may be rotatable relative to tensioner gear (191), which may permit rotation of shaft (130) by knob (134). As described in greater detail below, tensioner gear (191) may be used to take out any tolerance gaps between drive member (172) and lead screw (183).

Similarly, second tensioner gear (192) is engaged with a washer (194), which is further engaged with notch (164) of drive member (162). The engagement between washer (194) and drive member (162) is such that washer (194) and drive member (162) will translate together. In some versions, washer (194) is secured to tensioner gear (192) in such a manner that tensioner gear (192) both pulls washer (194) distally and pushes washer (194) proximally. Thus, in some such versions, second lead screw (184) is operable to both push articulation band (160) distally and pull articulation band (160) proximally, depending on which direction knob (128) is rotated. In the present example however, tensioner gear (192) merely abuts washer (194), such that tensioner gear (192) is operable to push washer (194) proximally but cannot pull washer (194) distally. Thus, in the present example, second lead screw (184) is operable to pull articulation band (160) proximally but cannot actively push articulation band (160) distally. Instead, second lead screw (184) may simply pull tensioner gear (192) distally to enable articulation band (160), drive member (162), and washer (194) to be driven distally in response to proximal retraction of articulation band (170) as communicated through articulation section (136). Other suitable relationships will be apparent to those of ordinary skill in the art in view of the teachings herein. It should also be understood that drive member (162) and/or washer (194) may be rotatable relative to tensioner gear (192), which may permit rotation of shaft (130) by knob (134). As described in greater detail below, tensioner gear (192) may be used to take out any tolerance gaps between drive member (162) and lead screw (184).

Figure 17A:
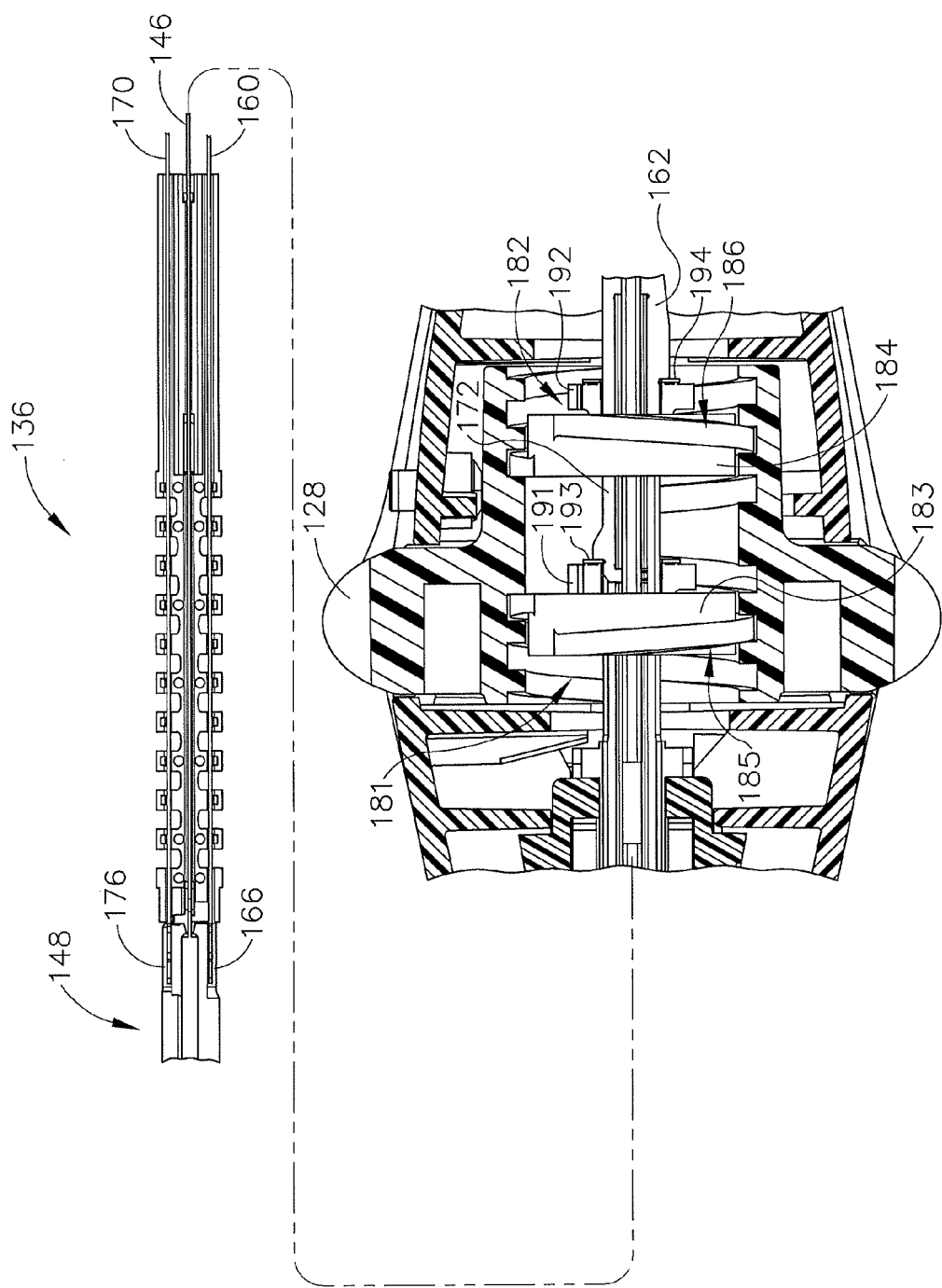
FIG. 17A depicts a partial cross-sectional view of articulation control components and the articulation section of the shaft of the device of FIG. 5, with the articulation section in a substantially straight configuration.
Figure 17B:
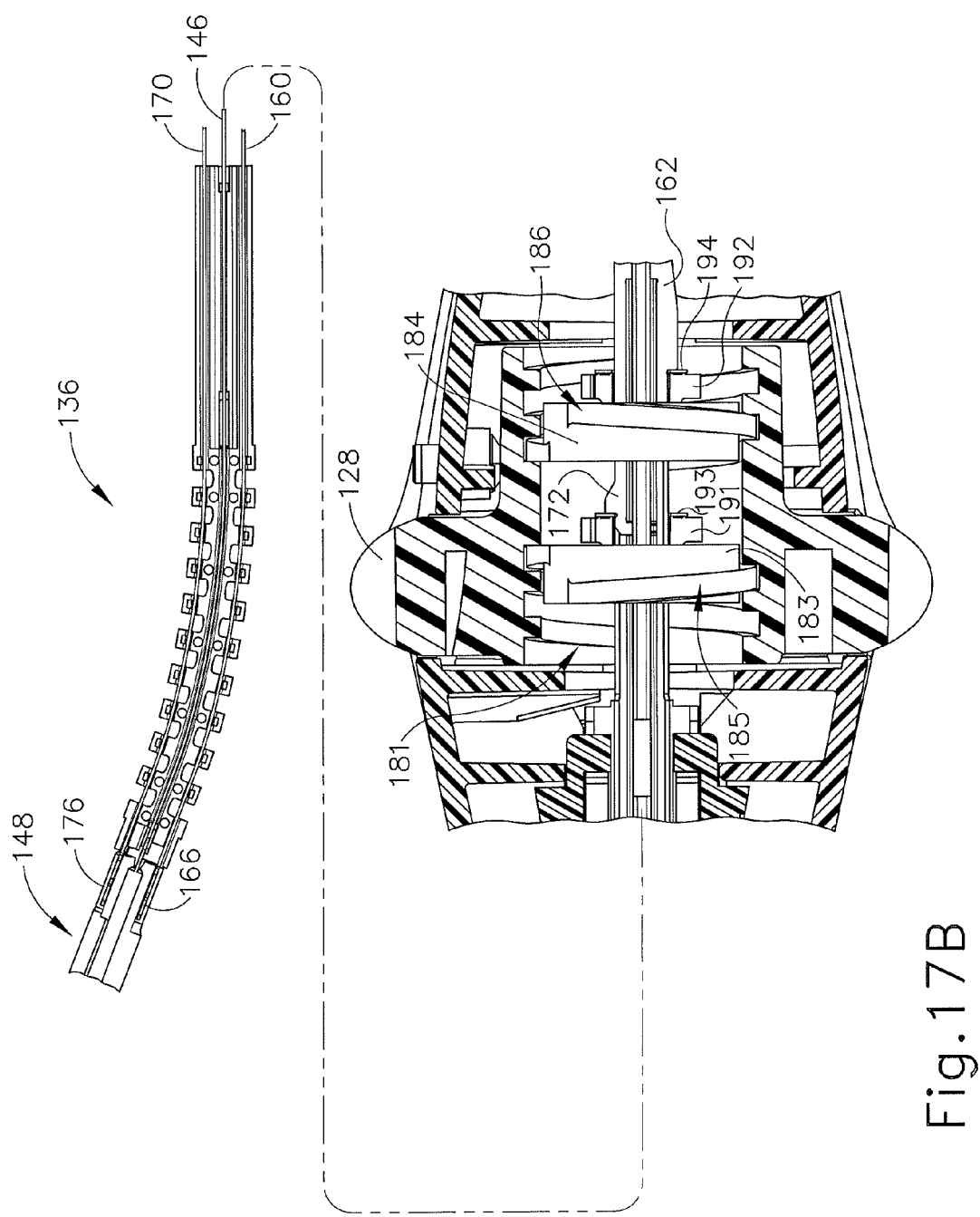
FIG. 17B depicts a partial cross-sectional view of the components of FIG. 17A, with the articulation section in a first stage of articulation.
Figure 17C:
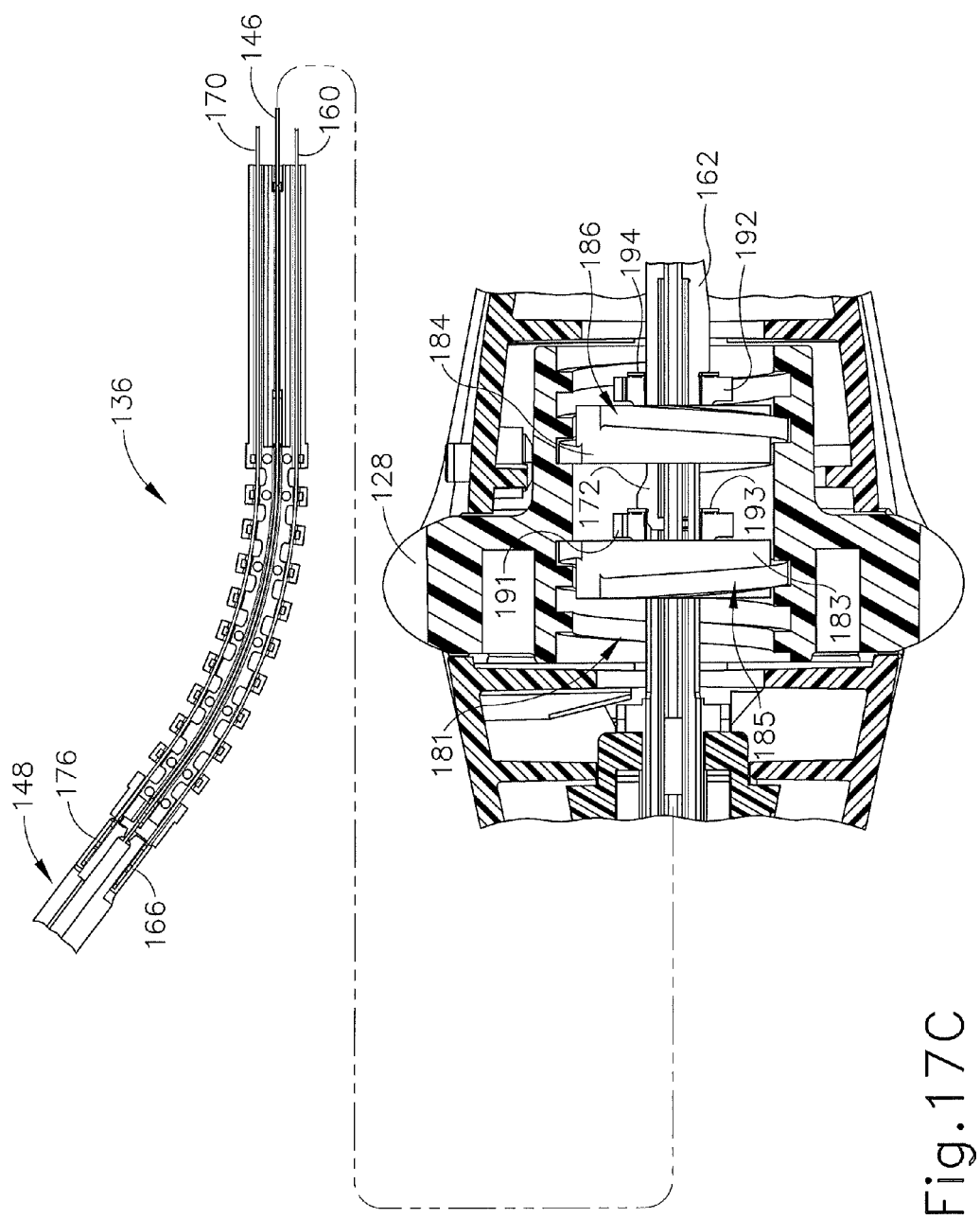
FIG. 17C depicts a partial cross-sectional view of the components of FIG. 17A, with the articulation section in a second stage of articulation.

FIGS. 17A-17C show several of the above described components interacting to bend articulation section (136) to articulate end effector (140). In FIG. 17A, articulation (136) is in a substantially straight configuration. Then, knob (128) is rotated, which causes lead screw (183) to translate proximally and lead screw (184) to advance distally. This proximal translation of lead screw (183) pulls articulation band (170) proximally, which causes articulation section (136) to start bending as shown in FIG. 17B. This bending of articulation section (136) pulls articulation band (160) distally. The distal advancement of lead screw (184) in response to rotation of knob (128) enables articulation band (160) and drive member (162) to advance distally. In some other versions, the distal advancement of lead screw (184) actively drives drive member (162) and articulation band (160) distally. As the user continues rotating knob (128), the above described interactions continue in the same fashion, resulting in further bending of articulation section (136) as shown in FIG. 17C. It should be understand that rotating knob (128) in the opposite direction will cause articulation section (136) to straighten, and further rotation in the opposite direction will cause articulation section (136) to bend in the opposite direction.

In some versions, knob (128) includes a visual indicator that is associated with articulation section (136) being in a substantially straight configuration. Such a visual indicator may align with a corresponding visual indicator on housing (121) of handpiece (120). Thus, when a user has rotated knob (128) to make articulation section (136) approach a substantially straight configuration, the user may observe such indicators to confirm whether articulation section (136) has in fact reached a substantially straight configuration. By way of example only, this may be done right before instrument (100) is withdrawn from a trocar to reduce the likelihood of articulation section (136) snagging on a distal edge of the trocar. Of course, such indicators are merely optional.

In some instances, manufacturing inconsistencies may result in articulation bands (160, 170) having slightly different lengths. In addition or in the alternative, there may be inherent manufacturing related inconsistencies in the initial positioning of lead screws (183, 184) relative to articulation knob (128), inconsistencies in the initial positioning of tensioner gears (191, 192) relative to lead screws (183, 184), and/or other inconsistencies that might result in undesirable positioning/relationships of articulation bands (160, 170). Such inconsistencies may result in lost motion or slop in the operation of the articulation features of instrument (100). To address such issues, tensioner gears (191, 192) may be rotated relative to lead screws (183, 184) to adjust the longitudinal position of drive members (162, 172) relative to lead screws (183, 184). For instance, if there is insufficient tension in articulation band (170), tensioner gear (191) may be rotated to drive washer (193) and drive member (172) proximally until articulation band (170) reaches a sufficient degree of tension. Similarly, if there is insufficient tension in articulation band (160), tensioner gear (192) may be rotated to drive washer (195) and drive member (162) proximally until articulation band (160) reaches a sufficient degree of tension. Lead screws (183, 184) may remain substantially stationary during such adjustments. Articulation section (136) may remain substantially straight during such adjustments and may even be held substantially straight during such adjustments.

In some versions, tensioner gears (191, 192) are rotated manually. In some other versions, tensioner gears (191, 192) are rotated automatically by a rack or other gear. In some such automated calibration systems, a control logic may monitor the load on a motor that is being used to drive a calibrating rack or gear that is engaged with tensioner gear (191, 192), and may automatically stop driving such a rack or gear when the load reaches a threshold associated with proper tensioning of band (160, 170). For instance, in cases where manufacturing inconsistencies or tolerance provide an initial gap between tensioner gears (191, 192) and washers (193, 194), or between washers (193, 194) and drive members (162, 172), tensioner gears (191, 192) may be rotated until such gaps are closed and sufficient contact is made between previously gapped components. As another merely illustrative variation, tensioner gears (191, 192) may be automatically stopped when the proximal ends of bands (160, 170) and/or drive members (162, 172) reach a certain point. Various suitable ways in which tensioner gears (191, 192) may be adjusted will be apparent to those of ordinary skill in the art in view of the teachings herein. It should also be understood that tensioner gears (191, 192) may be heat staked, glued, welded, or otherwise bonded to the respective lead screws (183, 184) when the gaps between drive members (162, 172) and their respective washers (193, 194) reach zero. Such bonding may prevent subsequent movement of tensioner gears (191, 192) relative to their respective lead screws (183, 184).

As another merely illustrative example, manufacturing inconsistencies may be addressed at the distal ends of bands (160, 170). For instance, before the distal ends of bands (160, 170) are secured to the proximal portion (148) of end effector (140), articulation section (136) may be held in a straight configuration and bands (160, 170) may be pulled distally to remove any slack in bands (160, 170). With bands (160, 170) both being in tension, bands (160, 170) may then be welded or otherwise secured to proximal portion (148) of end effector (140). It should be understood that this form of calibration is not limited to instrument (100), such that this form of calibration may be readily applied to various other instruments described herein, among others. Other suitable structures and methods for calibration will be apparent to those of ordinary skill in the art in view of the teachings herein.

B. Exemplary Articulation Control with Angled Rotary Knob

Figure 18:
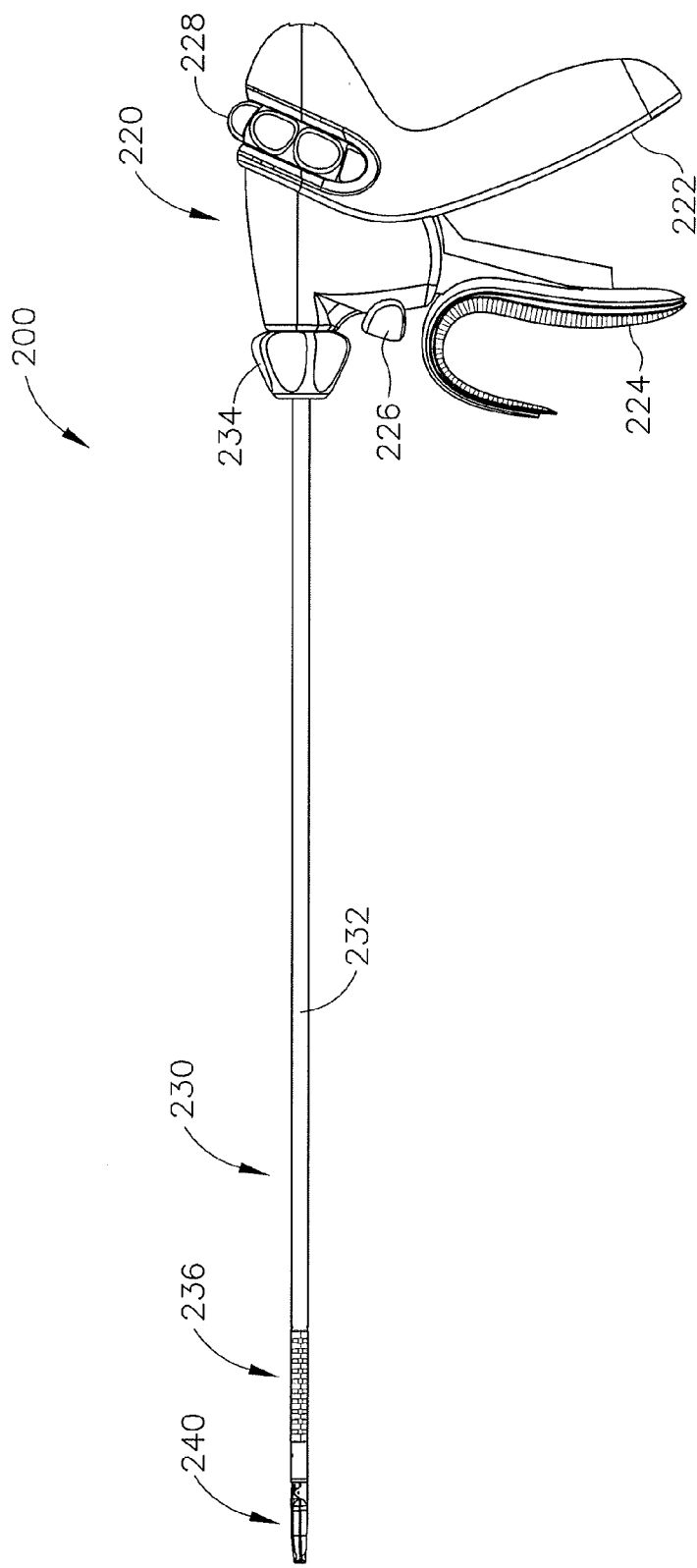
FIG. 18 depicts a side elevational view of another exemplary electrosurgical medical device, with an angled articulation control knob.

FIG. 18 depicts an exemplary electrosurgical instrument (200) that includes a handpiece (220), a shaft (230) extending distally from handpiece (220), and an end effector (240) disposed at a distal end of shaft (230). Handpiece (220) of the present example includes a pistol grip (222), a pivoting trigger (224), an activation button (226), and a rotary articulation knob (228). Trigger (224) is pivotable toward and away from pistol grip (222) to selectively actuate end effector (240) as described above and as described in one or more reference cited herein. Activation button (226) is operable to selectively activate RF circuitry that is in communication with end effector (240), as also described above and as described in one or more reference cited herein. In some versions, activation button (226) also serves as a mechanical lockout against trigger (224), such that trigger (224) cannot be fully actuated unless button (226) is being pressed simultaneously. Examples of how such a lockout may be provided are disclosed in one or more of the references cited herein. It should be understood that pistol grip (222), trigger (224), and button (226) may be modified, substituted, supplemented, etc. in any suitable way, and that the descriptions of such components herein are merely illustrative. Articulation knob (228) of the present example is operable to selectively control articulation section (236) of shaft (230), as will be described in greater detail below.

Figure 19:
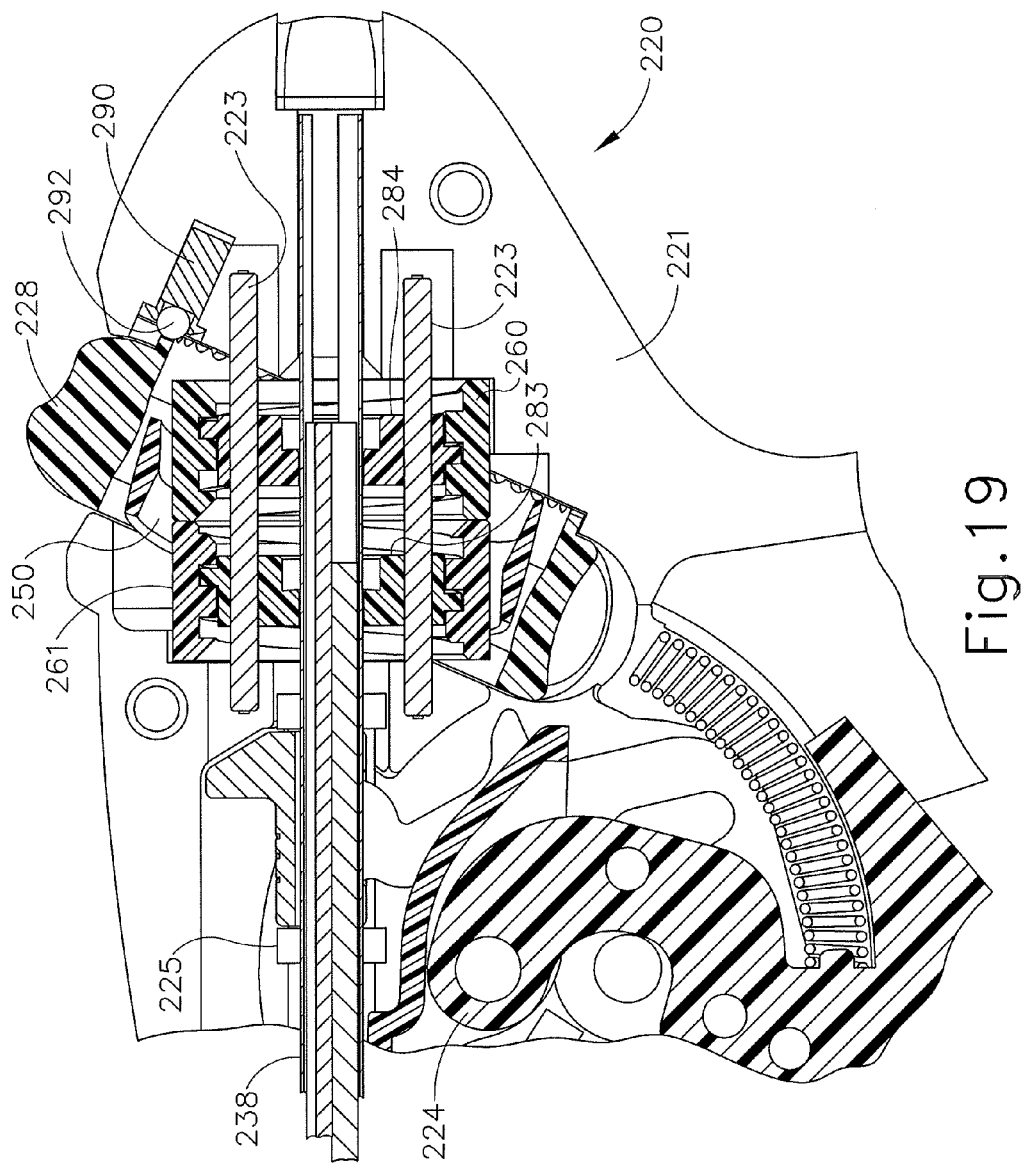
FIG. 19 depicts a cross-sectional view of articulation control components in the handle assembly of the device of FIG. 18.

Shaft (230) of the present example includes an outer sheath (232), an articulation section (236) at the distal end of sheath (232), and a cutting member driver tube (238) that is slidably and coaxially disposed within sheath (232). Cutting member driver tube (238) is secured to a firing beam (not shown), which is essentially equivalent to firing beam (60) described above. Cutting member driver tube (238) is movable longitudinally to drive the firing beam longitudinally. In the present example, driver tube (238) is advanced distally by squeezing trigger (224) toward pistol grip (222); while driver tube (238) is retracted proximally by releasing trigger (224) and/or by actively moving trigger (224) away from pistol grip (222). As shown in FIG. 19, a yoke (225) couples trigger (224) with driver tube (238). Of course, the firing beam may be moved in any other suitable fashion. Articulation section (236) of the present example is operable to selectively position end effector (240) at various angles relative to the longitudinal axis defined by sheath (232). Various examples of forms that articulation section (236) and other components of shaft (230) may take are described in various references cited herein, while further examples will be apparent to those of ordinary skill in the art in view of the teachings herein. Similarly, end effector (240) may be configured in accordance with end effector (40) described above, in accordance with the teachings of various references cited herein, and/or in any other suitable way as will be apparent to those of ordinary skill in the art in view of the teachings herein.

In some versions, shaft (230) is also rotatable about the longitudinal axis defined by sheath (232), relative to handpiece (220), via a knob (234). Such rotation may provide rotation of end effector (240) and shaft (230) unitarily. In some other versions, knob (234) is operable to rotate end effector (240) without rotating any portion of shaft (230) that is proximal of articulation section (236). As another merely illustrative example, electrosurgical instrument (200) may include one rotation control that provides rotatability of shaft (230) and end effector (240) as a single unit; and another rotation control that provides rotatability of end effector (240) without rotating any portion of shaft (230) that is proximal of section (236). Other suitable rotation schemes will be apparent to those of ordinary skill in the art in view of the teachings herein. Of course, rotatable features may simply be omitted if desired. In any versions of a device that provide rotation of a shaft (230) and/or end effector (240), a rotation knob (234) and/or shaft (230) and/or end effector (240) may include one or more markings facilitating visual identification of the rotational position. For instance, a user may correlate a marking on a rotation knob (234) with a corresponding marking on a shaft (230) and/or end effector (240) to better understand the orientation of such components with respect to the patient and instrument (200).

It should be understood that the components of shaft (230) that provide control for articulation section (236) may be substantially the same as those described above with reference to FIGS. 6-12 in the context of instrument (100). In other words, the features of FIGS. 19-20 may be readily incorporated with the features of FIGS. 6-12. In the present example, an articulation band (276) is the functional equivalent of articulation band (160) described above; while an articulation band (270) is the functional equivalent of articulation band (170) described above. In particular, articulation bands (270, 276) may translate in opposite directions to selectively bend articulation section (236) in either direction.

Figure 20:
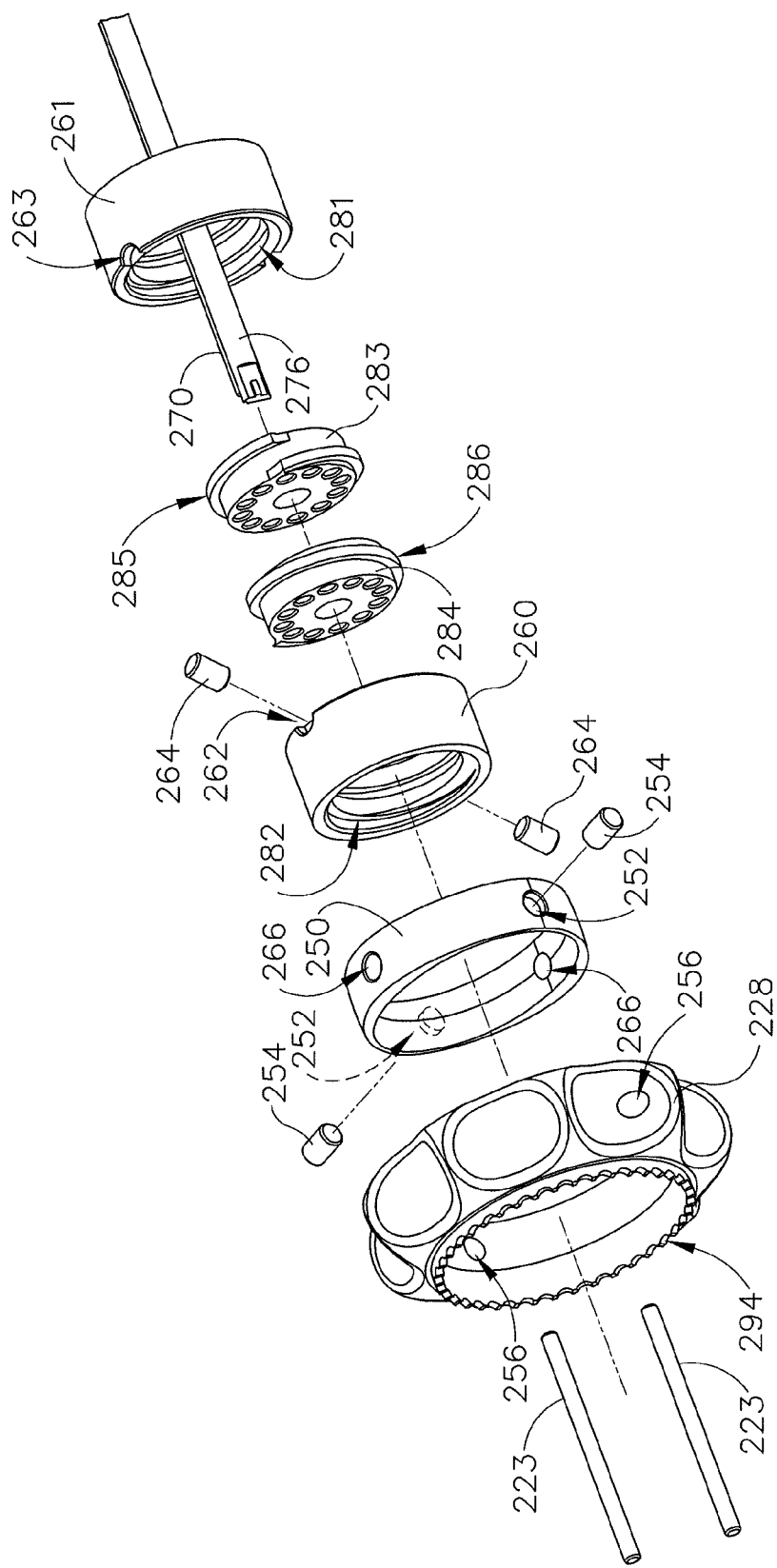
FIG. 20 depicts an exploded perspective view of some of the articulation control components of FIG. 19.

FIGS. 19-20 show various components of handpiece (220) that provide control for articulation of articulation section (236). In particular, these components include a proximal drive nut (260), a distal drive nut (261), a proximal lead screw (284), a distal lead screw (283), a gimbal drive ring (250), and knob (228). Lead screws (283, 284) are positioned along pins (223), which are secured to housing (221) of handpiece (220) such that lead screws (283, 284) translate within handpiece (220) but do not rotate within handpiece (220). Articulation band (270) is secured to distal lead screw (283) while articulation band (276) is secured to proximal lead screw (284). These relationships may be similar to those described above with respect to instrument (100). It should therefore be understood that articulation band (270) may translate concomitantly with distal lead screw (283) in either direction; while articulation band (276) may translate concomitantly with proximal lead screw (284) in either direction.

Distal lead screw (283) is threadingly engaged with distal drive nut (261). In particular, distal lead screw (283) includes external threading (285) that meshes with internal threading (281) of distal drive nut (261). Similarly, proximal lead screw (284) is threadingly engaged with proximal drive nut (260). In particular, proximal lead screw (284) includes external threading (286) that meshes with internal threading (282) of distal drive nut (260). Threading (281, 285) is oriented/angled in one direction while threading (282, 286) is oriented/angled in the opposite direction. Thus, threadings (281, 282, 285, 286) are analogous to threadings (181, 182, 185, 186) described above. Drive nuts (260, 261) are secured together in the present example such that drive nuts (260, 261) rotate together. Thus, when drive nuts (260, 261) are rotated, articulation band (270) translates in one direction while articulation band (276) translates in the other direction, depending on which direction drive nuts (260, 261) are rotated.

Drive nut (261) comprises an upper recess (263) and an opposing lower recess (not shown). Similarly, drive nut (260) comprises an upper recess (262) and an opposing lower recess (not shown). These recesses (262, 263) align and cooperate to receive pins (264) when drive nuts (260, 261) are joined together. These pins (264) are used to rotate drive nuts (260, 261). In particular, pins (264) are disposed in corresponding openings (266) of gimbal ring (250). Thus, drive nuts (260, 261) will rotate in response to rotation of gimbal ring (250). Gimbal ring (250) also includes another pair of opposing openings (252), which also receive a set of pins (254). These pins (254) are used to rotate gimbal ring (250). In particular, pins (254) are disposed in corresponding openings (256) of knob (228). Thus, gimbal ring (250) and drive nuts (260, 261) will rotate in response to rotation of knob (228). Unlike knob (128) described above, knob (228) of this example is oriented at an angle that is oblique relative to the longitudinal axis defined by shaft (230). Knob (228) is still nevertheless rotatable about the longitudinal axis defined by shaft (230). This configuration and operability is permitted by the pivotal couplings of pins (254, 264) in gimbal ring (250). In other words, gimbal ring (250) provides transfer of rotary motion of knob (228) to drive nuts (260, 261) in a manner similar to a universal joint, with simultaneous pivoting and rotation.

In some versions, the edges along which drive nuts (260, 261) contact each other include serrations or other mating features that enable the rotational positions of drive nuts (260, 261) relative to each other to be adjusted before drive nuts (260, 261) are secured together. By way of example only, this may enable the rotational positions of drive nuts (260, 261) to be adjusted to take up slack in articulation bands (270, 276) and/or to compensate for other manufacturing inconsistencies.

As also shown in FIG. 19, handpiece (220) includes a detent post (290) with a ball (292). Ball (292) is engaged with one of a series of recesses (294) arrayed about a proximal edge of knob (228). Post (290) is resiliently biased to urge ball (292) into a recess (294), such that ball (292) and recesses (294) form a detent feature. Such a feature may prevent inadvertent rotation of knob (228), thereby substantially preventing articulation section (236) from being inadvertently straightened or bent. Of course, instrument (100) could also include such a detent feature. Furthermore, such a detent feature may simply be omitted altogether.

Figure 21:
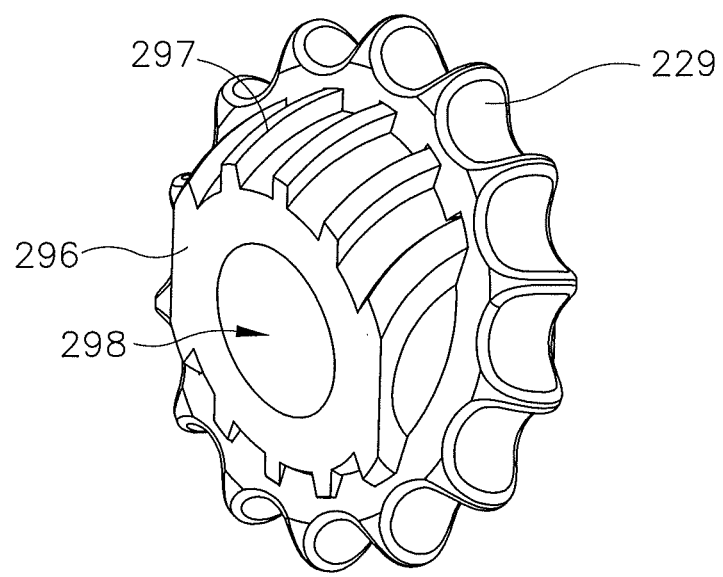
FIG. 21 depicts a perspective view of exemplary alternative articulation control components.

FIG. 21 shows exemplary alternative components that may be used to drive lead screws (283, 284). In particular, FIG. 21 shows an exemplary alternative knob (229) disposed about a ball drive (296). Ball drive (296) includes exterior ridges (297) and an inner bore (298). Knob (229) is slidably engaged with ridges (297) such that knob (229) may be used to freely rotate ball drive (296) about the longitudinal axis of bore (298), despite knob (229) being oriented along a plane that is oblique to the longitudinal axis of bore (298). Bore (298) may include two sets of opposing threading (not shown) that are essentially the same as threading (281, 282). Thus, with lead screws (283, 284), rotation of knob (229) will simultaneously translate lead screws (283, 284) in opposite directions. Still other suitable variations of components for instrument (200) will be apparent to those of ordinary skill in the art in view of the teachings herein.

C. Exemplary Articulation Control with Pivoting Semi-spherical Knob

Figure 22:
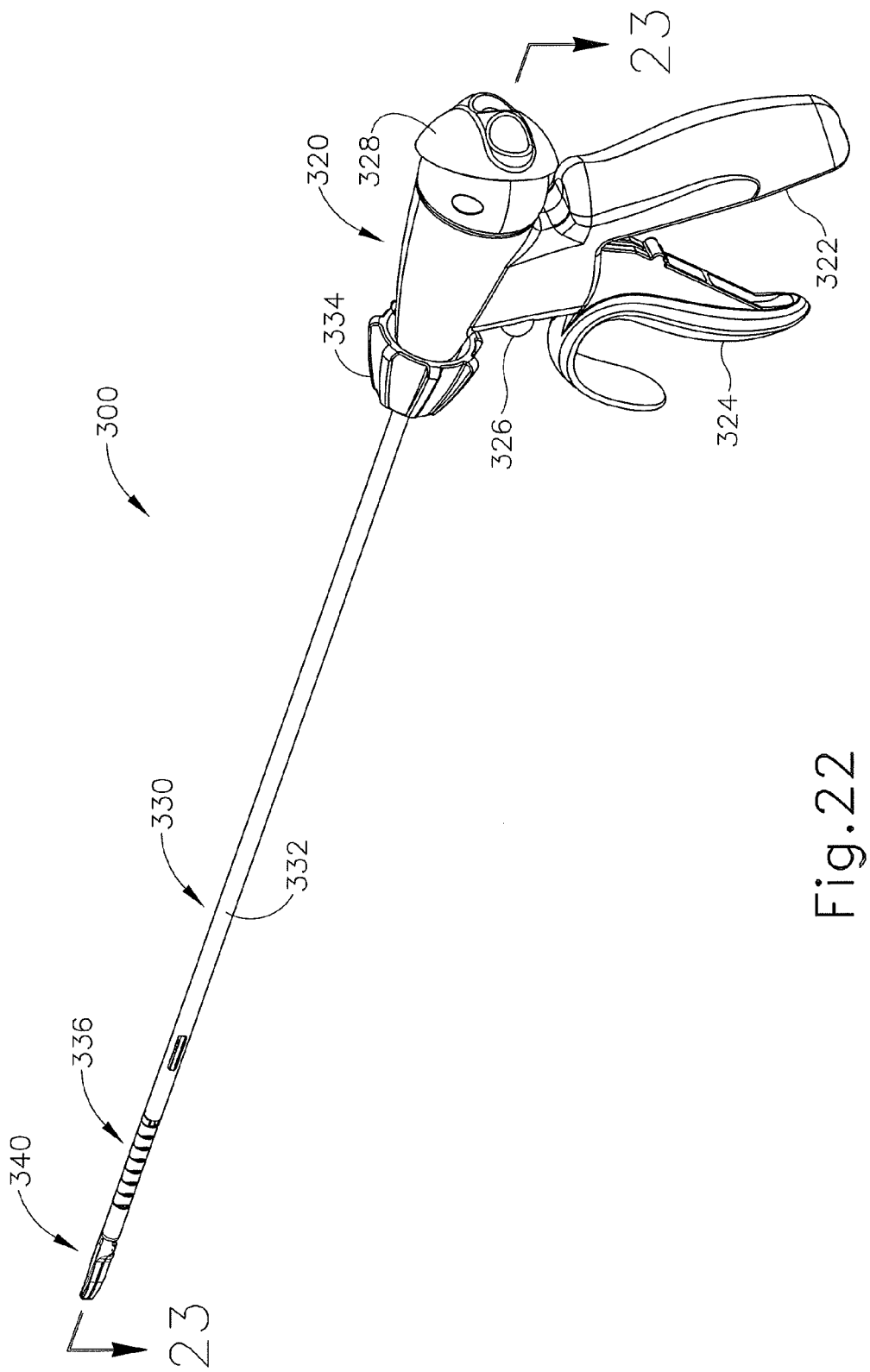
FIG. 22 depicts a perspective view of another exemplary electrosurgical medical device, with a pivoting semispherical articulation control knob.

FIG. 22 depicts an exemplary electrosurgical instrument (300) that includes a handpiece (320), a shaft (330) extending distally from handpiece (320), and an end effector (340) disposed at a distal end of shaft (330). Handpiece (320) of the present example includes a pistol grip (322), a pivoting trigger (324), an activation button (326), and a pivoting articulation knob (328). Trigger (324) is pivotable toward and away from pistol grip (322) to selectively actuate end effector (340) as described above and as described in one or more reference cited herein. Activation button (326) is operable to selectively activate RF circuitry that is in communication with end effector (340), as also described above and as described in one or more reference cited herein. In some versions, activation button (326) also serves as a mechanical lockout against trigger (324), such that trigger (324) cannot be fully actuated unless button (326) is being pressed simultaneously. Examples of how such a lockout may be provided are disclosed in one or more of the references cited herein. It should be understood that pistol grip (322), trigger (324), and button (326) may be modified, substituted, supplemented, etc. in any suitable way, and that the descriptions of such components herein are merely illustrative. Articulation knob (328) of the present example is operable to selectively control articulation section (336) of shaft (330), as will be described in greater detail below.

Figure 24:
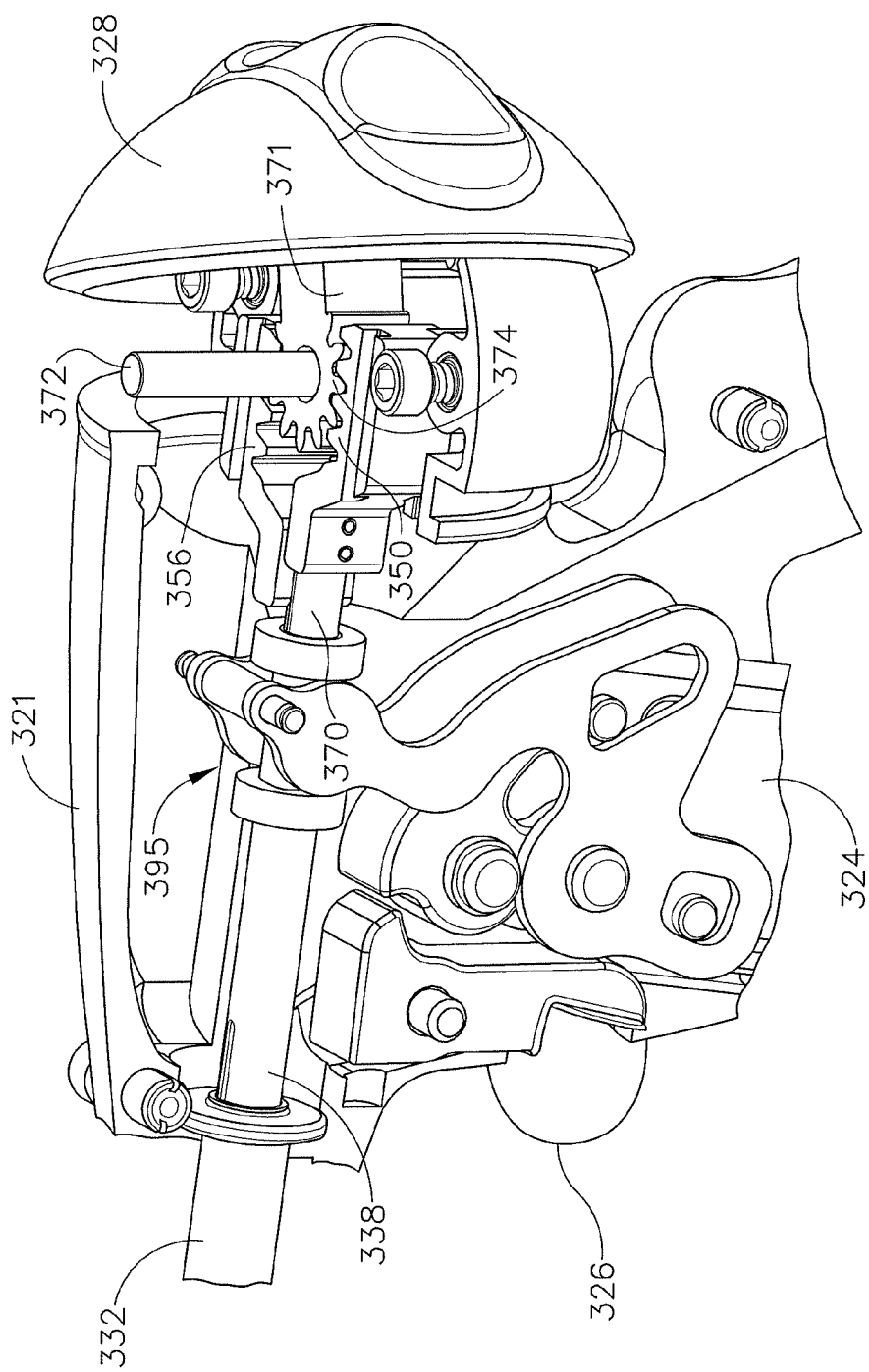
FIG. 24 depicts a perspective view of the articulation control components of FIG. 23.

Shaft (330) of the present example includes an outer sheath (332), an articulation section (336) at the distal end of sheath (332), and a cutting member driver tube (338) that is slidably and coaxially disposed within sheath (332). Cutting member driver tube (338) is secured to a firing beam (not shown), which is essentially equivalent to firing beam (60) described above. Cutting member driver tube (338) is movable longitudinally to drive the firing beam longitudinally. In the present example, driver tube (338) is advanced distally by squeezing trigger (324) toward pistol grip (322); while driver tube (338) is retracted proximally by releasing trigger (324) and/or by actively moving trigger (324) away from pistol grip (322). As shown in FIG. 24, a yoke (395) couples trigger (324) with driver tube (338). Of course, the firing beam may be moved in any other suitable fashion. Articulation section (336) of the present example is operable to selectively position end effector (340) at various angles relative to the longitudinal axis defined by sheath (332). Various examples of forms that articulation section (336) and other components of shaft (330) may take are described in various references cited herein, while further examples will be apparent to those of ordinary skill in the art in view of the teachings herein. Similarly, end effector (340) may be configured in accordance with end effector (40) described above, in accordance with the teachings of various references cited herein, and/or in any other suitable way as will be apparent to those of ordinary skill in the art in view of the teachings herein.

In some versions, shaft (330) is also rotatable about the longitudinal axis defined by sheath (332), relative to handpiece (320), via a knob (334). Such rotation may provide rotation of end effector (340) and shaft (330) unitarily. In some other versions, knob (334) is operable to rotate end effector (340) without rotating any portion of shaft (330) that is proximal of articulation section (336). As another merely illustrative example, electrosurgical instrument (300) may include one rotation control that provides rotatability of shaft (330) and end effector (340) as a single unit; and another rotation control that provides rotatability of end effector (340) without rotating any portion of shaft (330) that is proximal of section (336). Other suitable rotation schemes will be apparent to those of ordinary skill in the art in view of the teachings herein. Of course, rotatable features may simply be omitted if desired. In any versions of a device that provide rotation of a shaft (330) and/or end effector (340), a rotation knob (334) and/or shaft (330) and/or end effector (340) may include one or more markings facilitating visual identification of the rotational position. For instance, a user may correlate a marking on a rotation knob (334) with a corresponding marking on a shaft (330) and/or end effector (340) to better understand the orientation of such components with respect to the patient and instrument (300).

It should be understood that the components of shaft (330) that provide control for articulation section (336) may be substantially the same as those described above with reference to FIGS. 6-12 in the context of instrument (100). In other words, the features of FIGS. 22-24 may be readily incorporated with the features of FIGS. 6-12. In the present example, an articulation band (376) is the functional equivalent of articulation band (160) described above; while an articulation band (370) is the functional equivalent of articulation band (170) described above. In particular, articulation bands (370, 376) may translate in opposite directions to selectively bend articulation section (336) in either direction.

Figure 23:
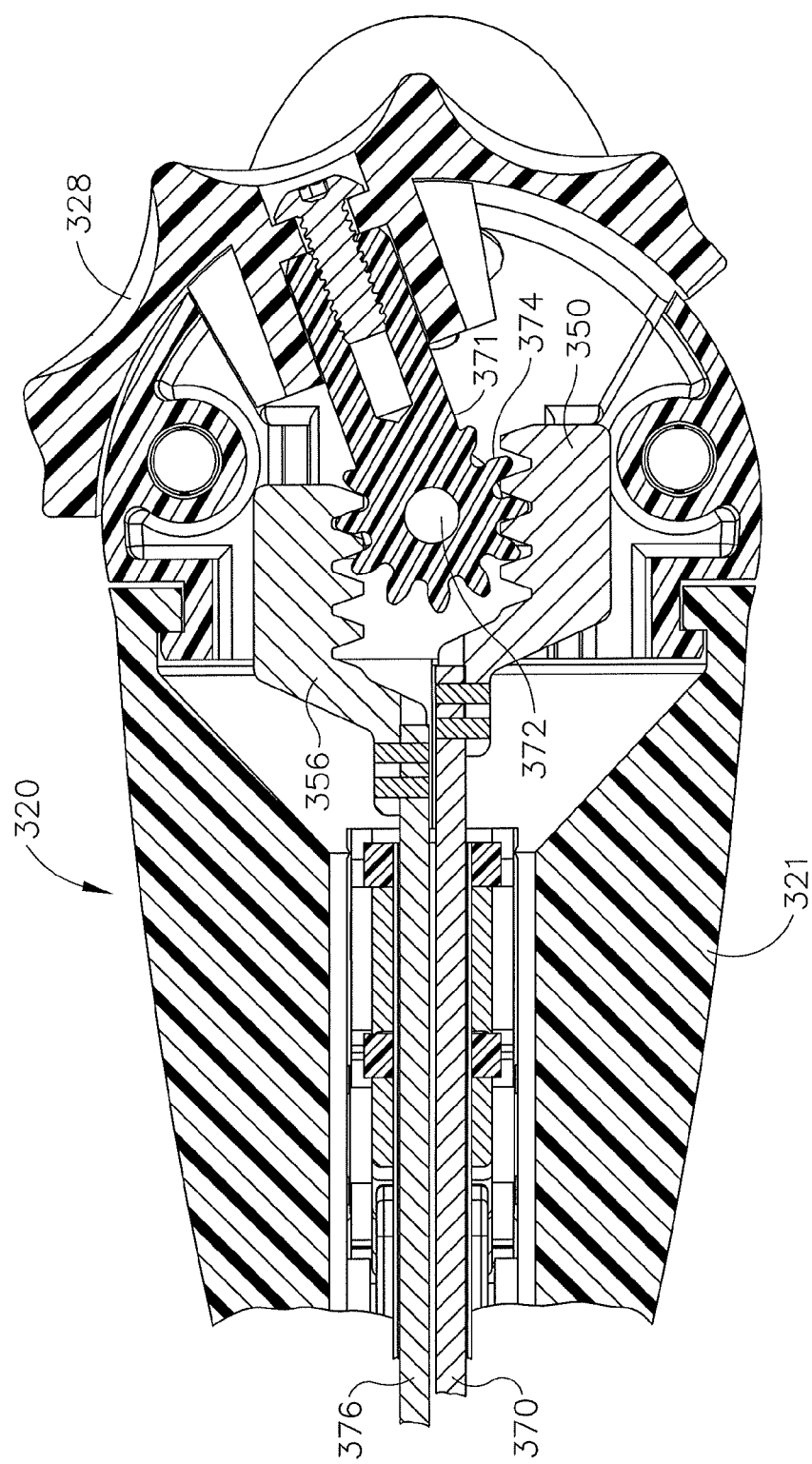
FIG. 23 depicts a cross-sectional view of articulation control components of the device of FIG. 22, taken along line 23-23 of FIG. 22.
Figure 25:
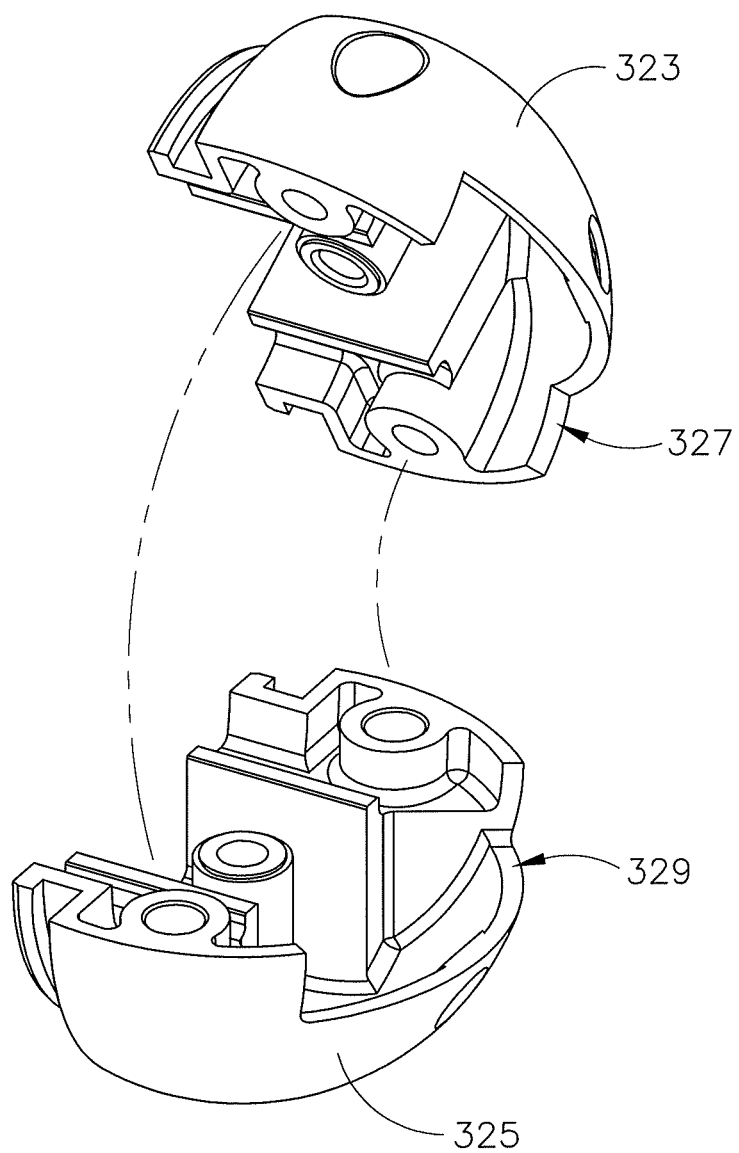
FIG. 25 depicts an exploded perspective view of housing components of the device of FIG. 22.

FIGS. 22-24 show various components of handpiece (320) that provide control for articulation of articulation section (336). In particular, these components include a pivoting knob (328) that is coupled with a post (371) having a pinion (374) at its distal end. A pin (372) is secured between a pair of housing portions (323, 325) and passes through post (371) such that post (371) pivots about pin (372). As shown in FIG. 25, housing portions (323, 325) include complementary recesses (327, 329) that provide a channel for post (371) to travel through when housing portions (323, 325) are secured together.

Pinion (374) meshes with a pair of opposing racks (350, 356), such that pivoting post (371) about pin (372) translates racks (350, 356) simultaneously in opposite directions. Rack (350) is unitarily secured to articulation band (370); while rack (356) is unitarily secured to articulation band (376). Thus, pivoting post (371) and pinion (374) in one direction will translate articulation band (370) distally while simultaneously translating articulation band (376) proximally; and pivoting post (371) and pinion (374) in the opposite direction will translate articulation band (370) proximally while simultaneously translating articulation band (376) distally. It should be understood that post (371) and pinion (374) may be pivoted by engaging knob (328). It should also be understood that such pivoting will bend articulation section (336) in a direction depending on the direction in which knob (328), post (371), and pinion (374) are pivoted. In some versions, a user may engage knob (328) with the thumb of the hand holding pistol grip (322), such that all features of instrument (300) may be entirely operated with a single hand.

As noted above, shaft (330) of the present example is rotatable relative to main housing (321) of handpiece (320). In some versions, articulation bands (370, 376), racks (350, 356), pin (372), post (371), knob (328), and housing portions (323, 325) all rotate together with shaft (330) relative to main housing (321) of handpiece (320). Thus, a user may rotate this entire assembly via either knob (334) or knob (328) and/or housing portions (323, 325). In such versions, the plane along which knob (328) pivots will also rotate with shaft (330), thereby providing the user with a more intuitive sense of the angular orientation of end effector (340) and the plane of articulation for articulation section (336). In some other versions, articulation bands (370, 376), racks (350, 356), pin (372), post (371), knob (328), and housing portions (323, 325) remain rotationally stationary relative to main housing (321) of handpiece (320) while shaft (330) rotates relative to main housing (321) of handpiece (320). Other suitable ways in which instrument (300) may be configured and operable will be apparent to those of ordinary skill in the art in view of the teachings herein.

D. Exemplary Articulation Control with Pivoting Fin

Figure 26:
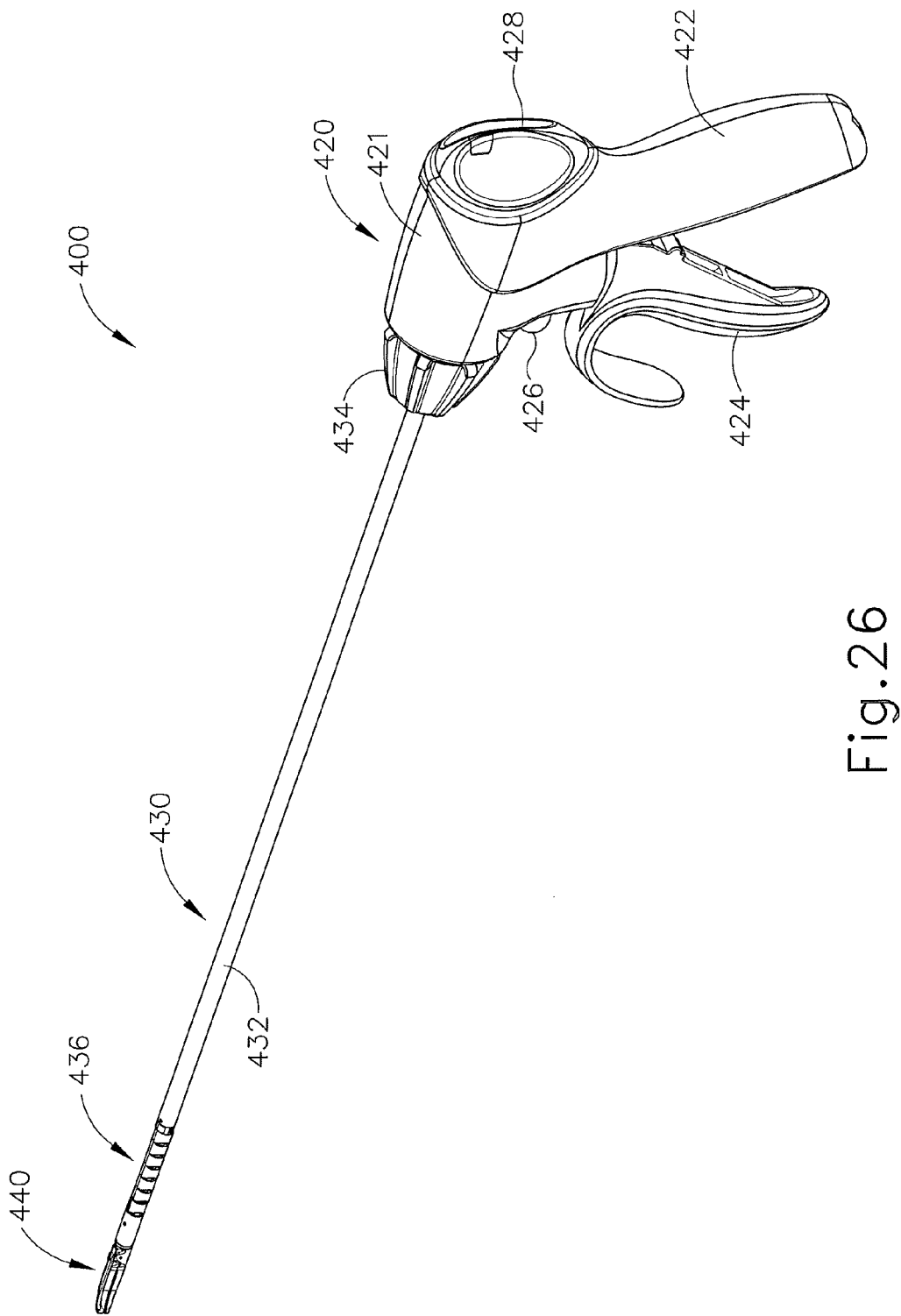
FIG. 26 depicts a perspective view of another exemplary electrosurgical medical device, with a pivoting articulation control fin.
Figure 27:
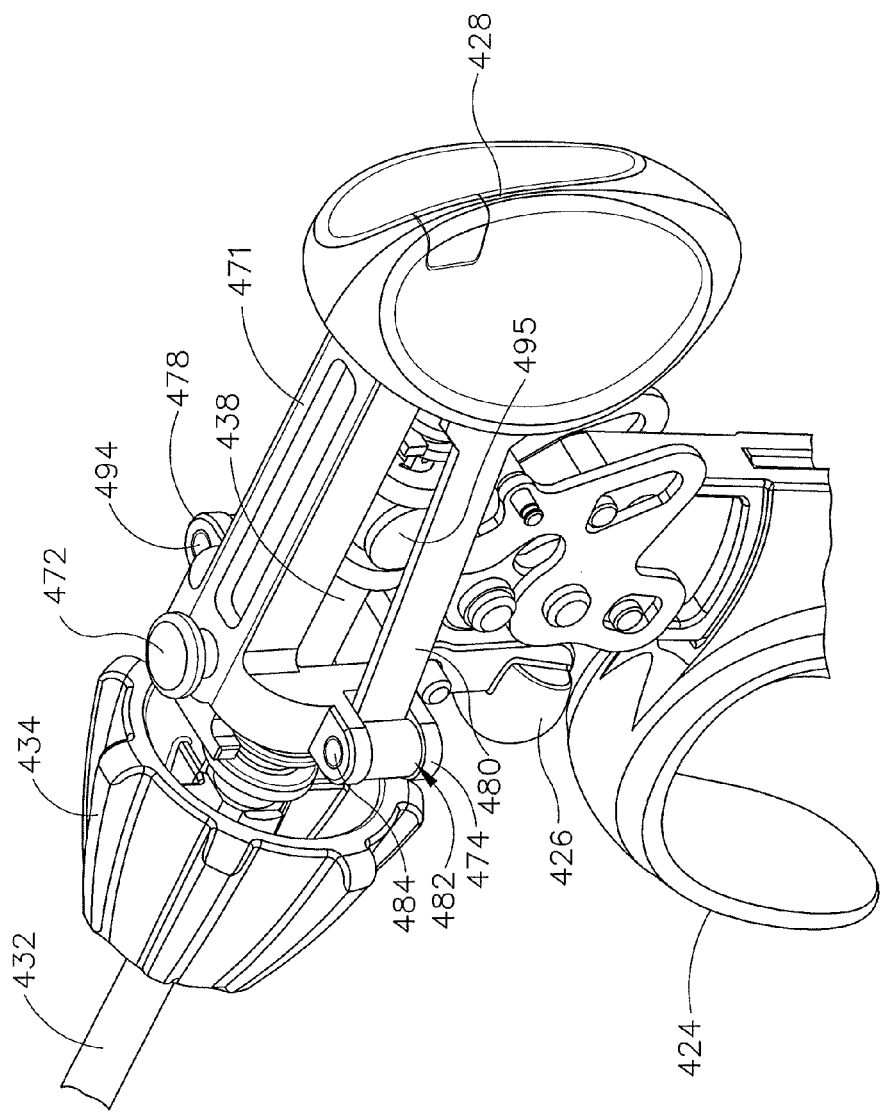
FIG. 27 depicts a perspective view of articulation control components of the device of FIG. 26.
Figure 28:
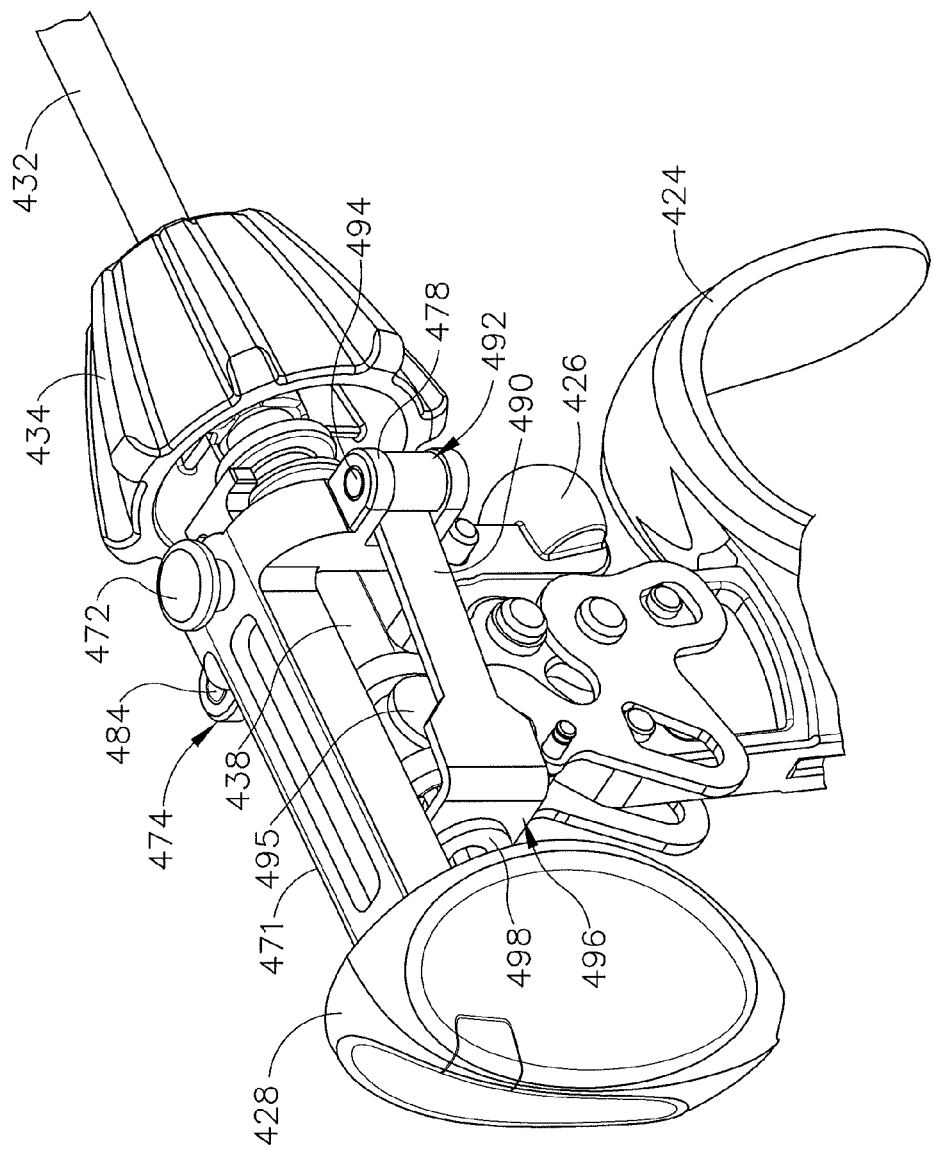
FIG. 28 depicts another perspective view of articulation control components of the device of FIG. 26.

FIG. 26 depicts an exemplary electrosurgical instrument (400) that includes a handpiece (420), a shaft (430) extending distally from handpiece (420), and an end effector (440) disposed at a distal end of shaft (430). Handpiece (420) of the present example includes a pistol grip (422), a pivoting trigger (424), an activation button (426), and a pivoting articulation fin (428). Trigger (424) is pivotable toward and away from pistol grip (422) to selectively actuate end effector (440) as described above and as described in one or more reference cited herein. Activation button (426) is operable to selectively activate RF circuitry that is in communication with end effector (440), as also described above and as described in one or more reference cited herein. In some versions, activation button (426) also serves as a mechanical lockout against trigger (424), such that trigger (424) cannot be fully actuated unless button (426) is being pressed simultaneously. Examples of how such a lockout may be provided are disclosed in one or more of the references cited herein. It should be understood that pistol grip (422), trigger (424), and button (426) may be modified, substituted, supplemented, etc. in any suitable way, and that the descriptions of such components herein are merely illustrative. Articulation fin (428) of the present example is operable to selectively control articulation section (436) of shaft (430), as will be described in greater detail below.

Shaft (430) of the present example includes an outer sheath (432), an articulation section (436) at the distal end of sheath (432), and a cutting member driver tube (438) that is slidably and coaxially disposed within sheath (432). Cutting member driver tube (438) is secured to a firing beam (not shown), which is essentially equivalent to firing beam (60) described above. Cutting member driver tube (438) is movable longitudinally to drive the firing beam longitudinally. In the present example, driver tube (438) is advanced distally by squeezing trigger (424) toward pistol grip (422); while driver tube (438) is retracted proximally by releasing trigger (424) and/or by actively moving trigger (424) away from pistol grip (422). As shown in FIG. 24, a yoke (495) couples trigger (424) with driver tube (438). Of course, the firing beam may be moved in any other suitable fashion. Articulation section (436) of the present example is operable to selectively position end effector (440) at various angles relative to the longitudinal axis defined by sheath (432). Various examples of forms that articulation section (436) and other components of shaft (430) may take are described in various references cited herein, while further examples will be apparent to those of ordinary skill in the art in view of the teachings herein. Similarly, end effector (440) may be configured in accordance with end effector (40) described above, in accordance with the teachings of various references cited herein, and/or in any other suitable way as will be apparent to those of ordinary skill in the art in view of the teachings herein.

In some versions, shaft (430) is also rotatable about the longitudinal axis defined by sheath (432), relative to handpiece (420), via a knob (434). Such rotation may provide rotation of end effector (440) and shaft (430) unitarily. In some other versions, knob (434) is operable to rotate end effector (440) without rotating any portion of shaft (430) that is proximal of articulation section (436). As another merely illustrative example, electrosurgical instrument (400) may include one rotation control that provides rotatability of shaft (430) and end effector (440) as a single unit; and another rotation control that provides rotatability of end effector (440) without rotating any portion of shaft (430) that is proximal of section (436). Other suitable rotation schemes will be apparent to those of ordinary skill in the art in view of the teachings herein. Of course, rotatable features may simply be omitted if desired. In any versions of a device that provide rotation of a shaft (430) and/or end effector (440), a rotation knob (434) and/or shaft (430) and/or end effector (440) may include one or more markings facilitating visual identification of the rotational position. For instance, a user may correlate a marking on a rotation knob (434) with a corresponding marking on a shaft (430) and/or end effector (440) to better understand the orientation of such components with respect to the patient and instrument (400).

It should be understood that the components of shaft (430) that provide control for articulation section (436) may be substantially the same as those described above with reference to FIGS. 6-12 in the context of instrument (100). In other words, the features of FIGS. 26-29 may be readily incorporated with the features of FIGS. 6-12. In the present example, an articulation band (476) is the functional equivalent of articulation band (160) described above; while an articulation band (470) is the functional equivalent of articulation band (170) described above. In particular, articulation bands (470, 476) may translate in opposite directions to selectively bend articulation section (436) in either direction.

Figure 29:
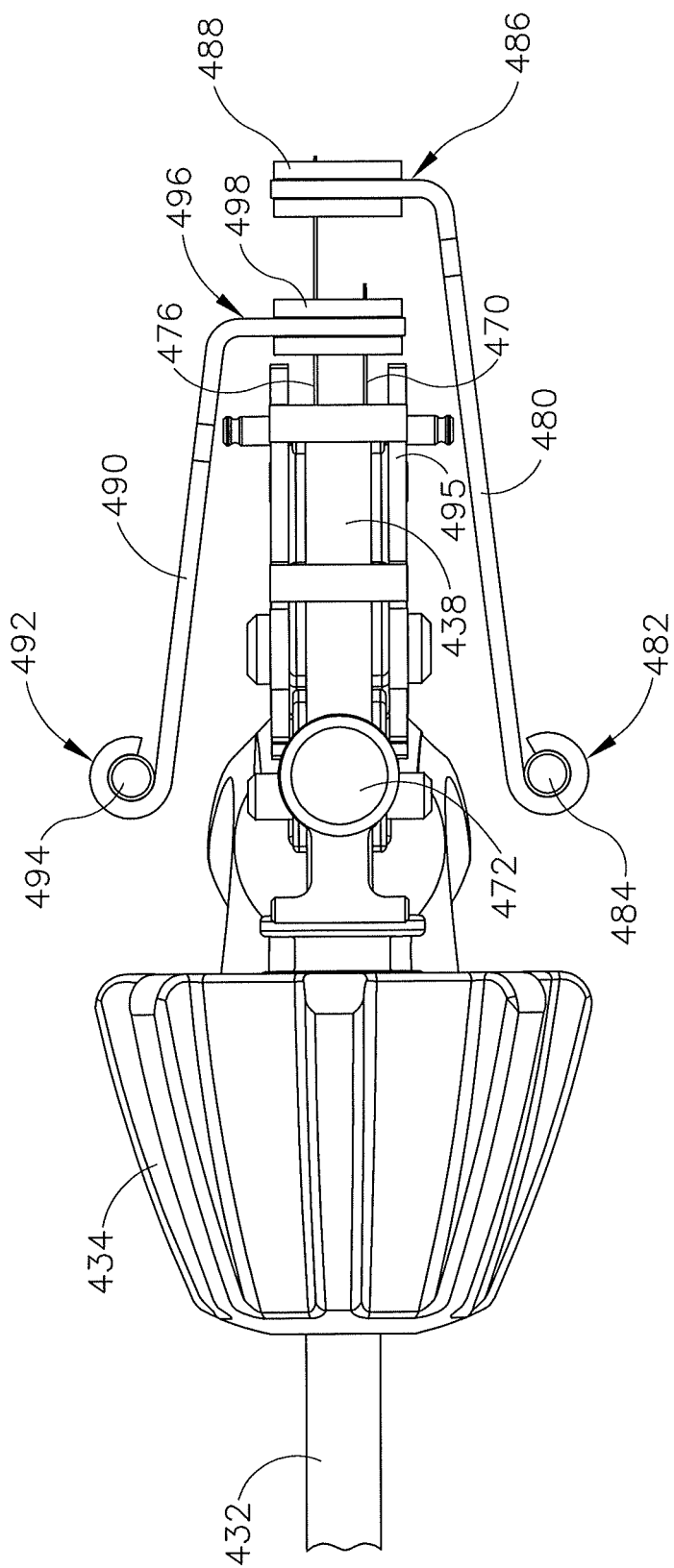
FIG. 29 depicts a top plan view of some of the articulation control components of FIGS. 27-28.

FIGS. 26-29 show various components of handpiece (420) that provide control for articulation of articulation section (436). In particular, these components include a pivoting fin (428) that is coupled with a post (471) having a pair of yokes (474, 478) at its distal end. A pin (472) is secured to housing (421) of handpiece (420) and passes through post (471) such that post (471) pivots about pin (472). It should be noted that post (471) and pivoting fin (428) are omitted from FIG. 29 for clarity. A first actuation arm (480) includes a distal end (482) that is pivotally coupled with yoke (474) by a pin (484). A second actuation arm (490) includes a distal end (492) that is pivotally coupled with yoke (478) by a pin (494). The proximal end (486) of first actuation arm (480) includes a coupling (488), which is fixedly secured to the proximal end of actuation beam (476). The proximal end (496) of second actuation arm (490) includes a coupling (498), which is fixedly secured to the proximal end of actuation beam (470). As best seen in FIG. 29, actuation beam (476) passes through coupling (498). However, actuation beam (476) is not secured to coupling (498), such that actuation beam (476) and coupling (498) may move freely relative to each other.

Actuation arms (480, 490) serve as linkages transferring pivotal movement of fin (428) and post (471) into translational movement of actuation beams (470, 476). In particular, pivotal movement of fin (428) in one direction is communicated through arms (480, 490) to translate articulation beam (470) distally while simultaneously translating articulation beam (476) proximally. Pivotal movement of fin (428) in the opposite direction is communicated through arms (480, 490) to translate articulation beam (470) proximally while simultaneously translating articulation beam (476) distally. It should also be understood that such pivoting will bend articulation section (436) in a direction depending on the direction in which fin (428) and post (471) are pivoted. In some versions, a user may engage fin (428) with the thumb of the hand holding pistol grip (422), such that all features of instrument (400) may be entirely operated with a single hand.

In some versions, the pivotal position of fin (428) may be selectively locked in place. For instance, instrument (400) may be configured to require fin (428) to be moved vertically (either up or down) to unlock and/or to pivot fin (428). By way of example only, housing (421) may comprise a plurality of recesses configured to selectively receive post (471) depending on the pivotal position of post (471) about pin (472). A resilient member may bias post (471) into engagement with recesses, such that the user must deflect post (471) away from the recesses, against this resilient bias, in order to pivotally adjust the position of fin (428). As another merely illustrative variation, instrument (400) may require fin (428) to be pushed distally or pulled proximally to unlock fin (428) for pivotal movement. Again, such features may resiliently bias fin (428) to a locked configuration. Other suitable ways in which the pivotal position of fin (428) may be selectively locked will be apparent to those of ordinary skill in the art in view of the teachings herein. Alternatively, instrument (400) may simply lack such locking altogether.

Other suitable ways in which instrument (400) may be configured and operable will be apparent to those of ordinary skill in the art in view of the teachings herein.

IV. Other Exemplary Features

It should be understood that any of the versions of electrosurgical instrument (10) described herein may include various other features in addition to or in lieu of those described above. Several examples of such other features are described below, while other features will be apparent to those of ordinary skill in the art in view of the teachings herein.

A. Exemplary Electrical Couplings

As noted above, one or more components of end effector (40, 140, 240, 340, 440) may be placed in electrical communication with a power source. Such a power source may be internal to instrument (10, 100, 200, 300, 400) or may be external to instrument. FIGS. 30-36 show several exemplary components that may be used to provide electrical couplings between a power source and one or more components of end effector (40, 140, 240, 340, 440). While the examples of FIGS. 30-36 are shown in the context of instrument (100), it should be understood that the examples may be readily applied to any other version of instrument (10, 200, 300, 400) described herein. Similarly, the examples may be readily applied to various instruments described in the references cited herein, among other types of instruments as will be apparent to those of ordinary skill in the art in view of the teachings herein.

Figure 30:
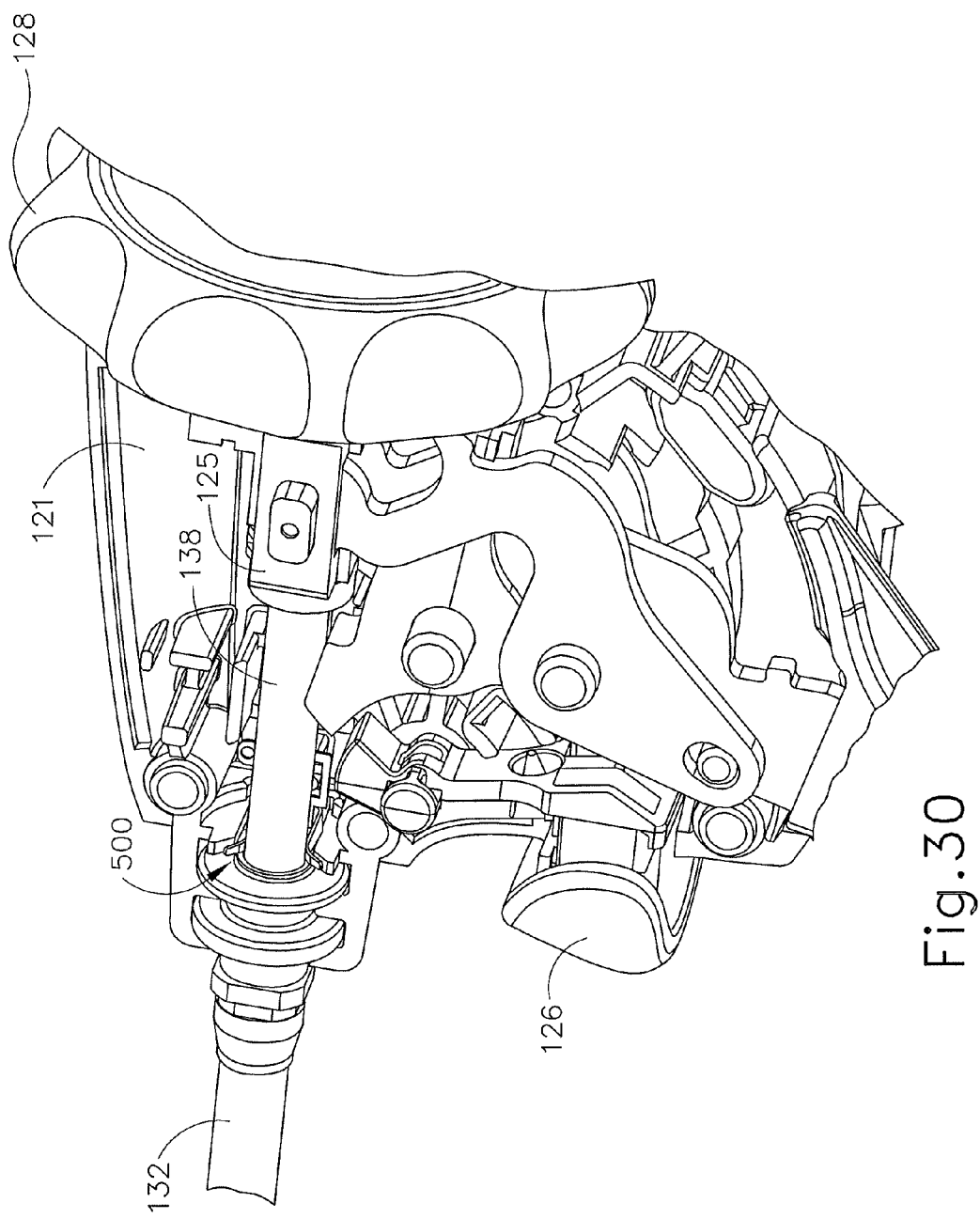
FIG. 30 depicts a perspective view of a distal portion of the handle assembly of the device of FIG. 5, with a housing half of the handle assembly removed.
Figure 31:
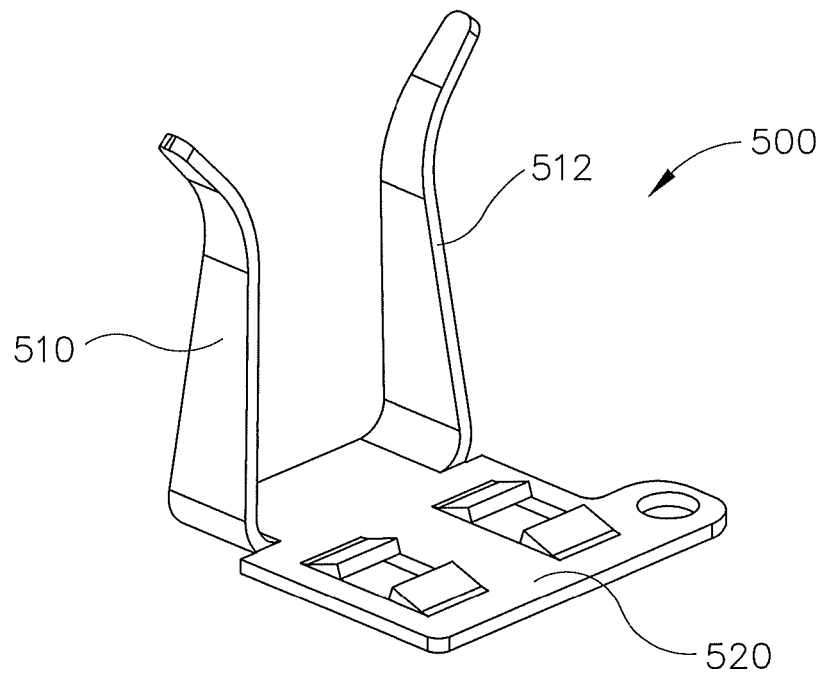
FIG. 31 depicts an exemplary electrical coupling of the distal portion of FIG. 30.

As shown in FIG. 30, a coupling (500) is secured to cutting member driver tube (138). Coupling (500) is formed from an electrically conductive material such as steel or some other metal. Coupling (500) includes a pair of arms (510, 512) that include outwardly flared free ends. Arms (510, 512) are configured to receive driver tube (138) and are resiliently biased to maintain contact with driver tube (138) as driver tube (138) is translated and rotated relative to coupling (500). Driver tube (138) is also formed of an electrically conductive material such as steel or some other metal. Driver tube (138) is also in electrical communication with cutting member (146) in addition to being in mechanical communication with cutting member (146). Driver tube (138) thus provides a conductive conduit between coupling (500) and cutting member (146). Arms (510, 512) extend from a base (520), which is secured to housing (121) of handpiece (120). A wire (not shown) is coupled with base (520). Such a wire may be further coupled with a power source. In the present example, the wire is grounded. In particular, one or more electrodes of end effector (140) serve as active electrodes while cutting member (146) serves as a ground return path. Driver tube (138) and coupling (500) further provide a ground return path from cutting member (146) to the ground wire. Of course, in some other versions these components may instead serve as active electrical components instead of serving as grounding components.

Figure 32:
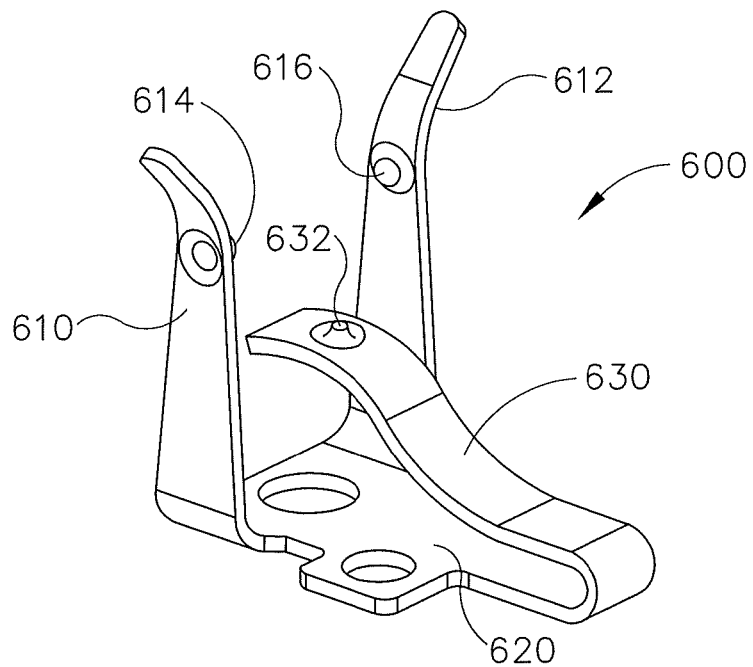
FIG. 32 depicts an exemplary alternative electrical coupling.
Figure 33:
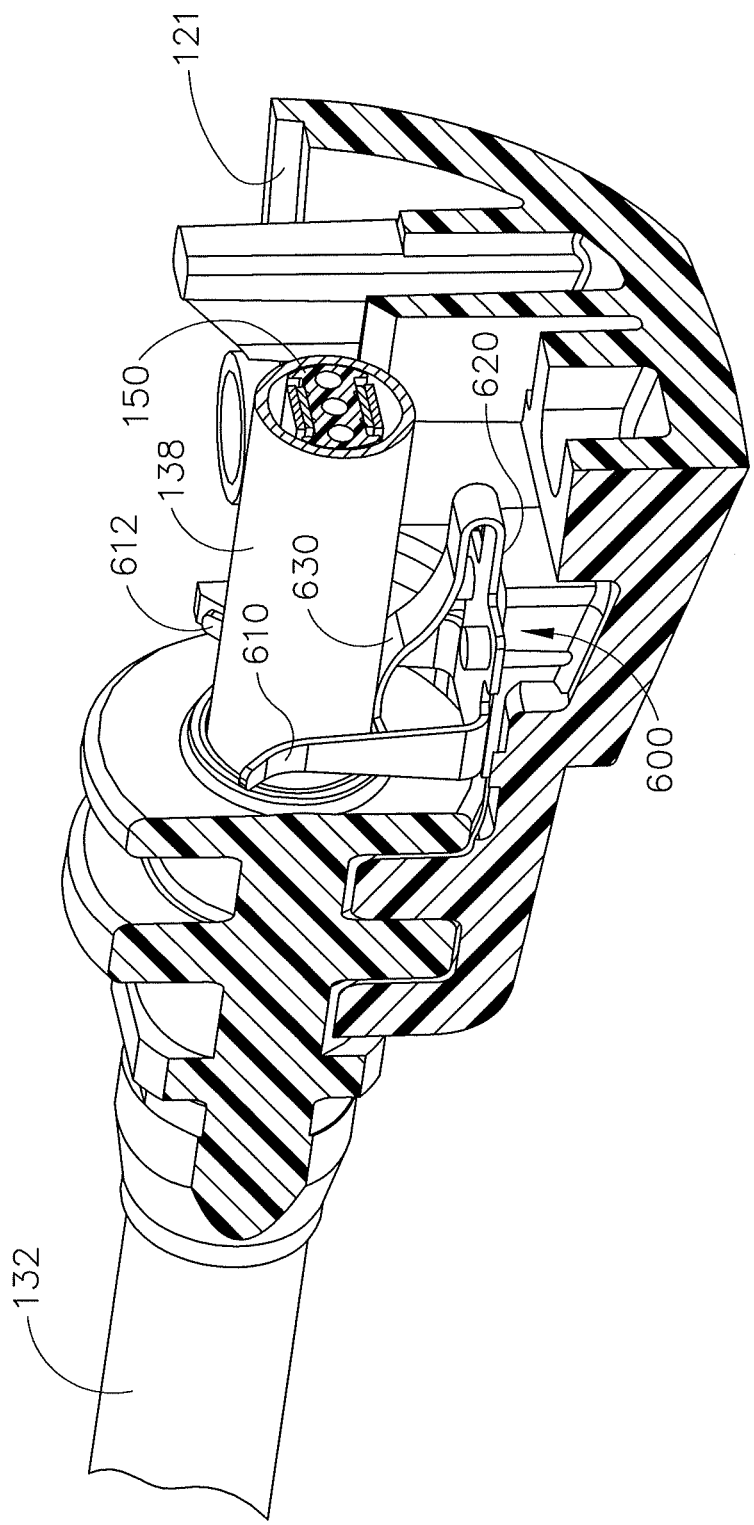
FIG. 33 depicts a partial cross-sectional perspective view of the electrical coupling of FIG. 32 installed in the distal portion of FIG. 30.

FIG. 32 shows an exemplary alternative coupling (600) that may be used in place of coupling (500). Coupling of this example includes three arms (610, 612, 630). Arms (610, 612) are substantially similar to arms (510, 512) described above, and include respective contact points (614, 616) at which they contact driver tube (138). Arms (610, 612) are positioned along a common plane and provide contact with driver tube (138) along a common axis (e.g., along a line defined between points (614, 616)). Arm (630) is positioned along a plane that is perpendicular to the plane of arms (610, 612). Arm (630) is resiliently biased (e.g., like a leaf spring, etc.) to urge contact point (632) into contact with driver tube (138). Thus, as shown in FIG. 33, coupling (600) is configured to engage driver tube (138) at three separate contact points (614, 616, 632) and along two perpendicular planes/axes. This may provide more reliable electrical continuity between coupling (600) and driver tube (138), including while driver tube (138) is translating and/or rotating relative to coupling (600). Arms (610, 612, 630) all extend from a base (620), which may be secured to housing (121) of handpiece (120). As with base (520), a wire (not shown) may be coupled with base (620) to provide a ground return path or to communicate active power to coupling (600) and thereby to cutting member (146).

Figure 34:
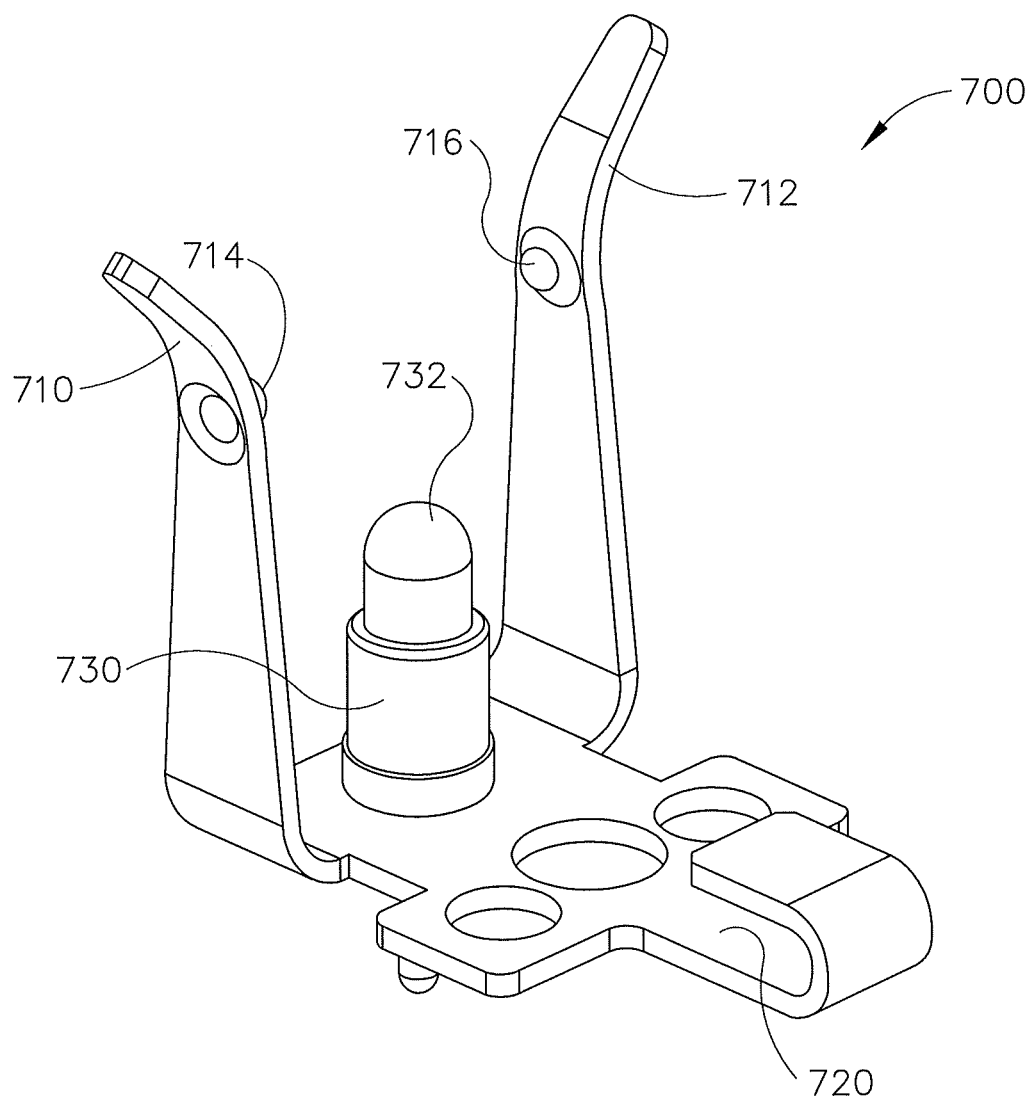
FIG. 34 depicts another exemplary alternative electrical coupling.

FIG. 34 shows yet another exemplary alternative coupling (700) that may be used in place of coupling (700). Coupling of this example includes a pair of arms (710, 712). Arms (710, 712) are substantially similar to arms (510, 512) described above, and include respective contact points (714, 716) at which they contact driver tube (138). Arms (710, 712) are positioned along a common plane and provide contact with driver tube (138) along a common axis (e.g., along a line defined between points (714, 716)). Coupling (700) also includes a conductive pin (732) and a conductive can (730) that are positioned along a plane that is perpendicular to the plane of arms (710, 712). A spring (not shown) within can (730) resiliently biases pin (732) away from can (730) to urge pin (732) into contact with driver tube (138). Thus, coupling (700) is configured to engage driver tube (138) at three separate contact points (714, 716, 732) and along two perpendicular planes/axes. This may provide more reliable electrical continuity between coupling (700) and driver tube (138), including while driver tube (138) is translating and/or rotating relative to coupling (700). Arms (710, 712) and can (730) all extend from a base (720), which may be secured to housing (121) of handpiece (120). As with base (520), a wire (not shown) may be coupled with base (720) to provide a ground return path or to communicate active power to coupling (700) and thereby to cutting member (146). Other suitable structures and methods for electrically coupling driver tube (138) will be apparent to those of ordinary skill in the art in view of the teachings herein.

Figure 35:
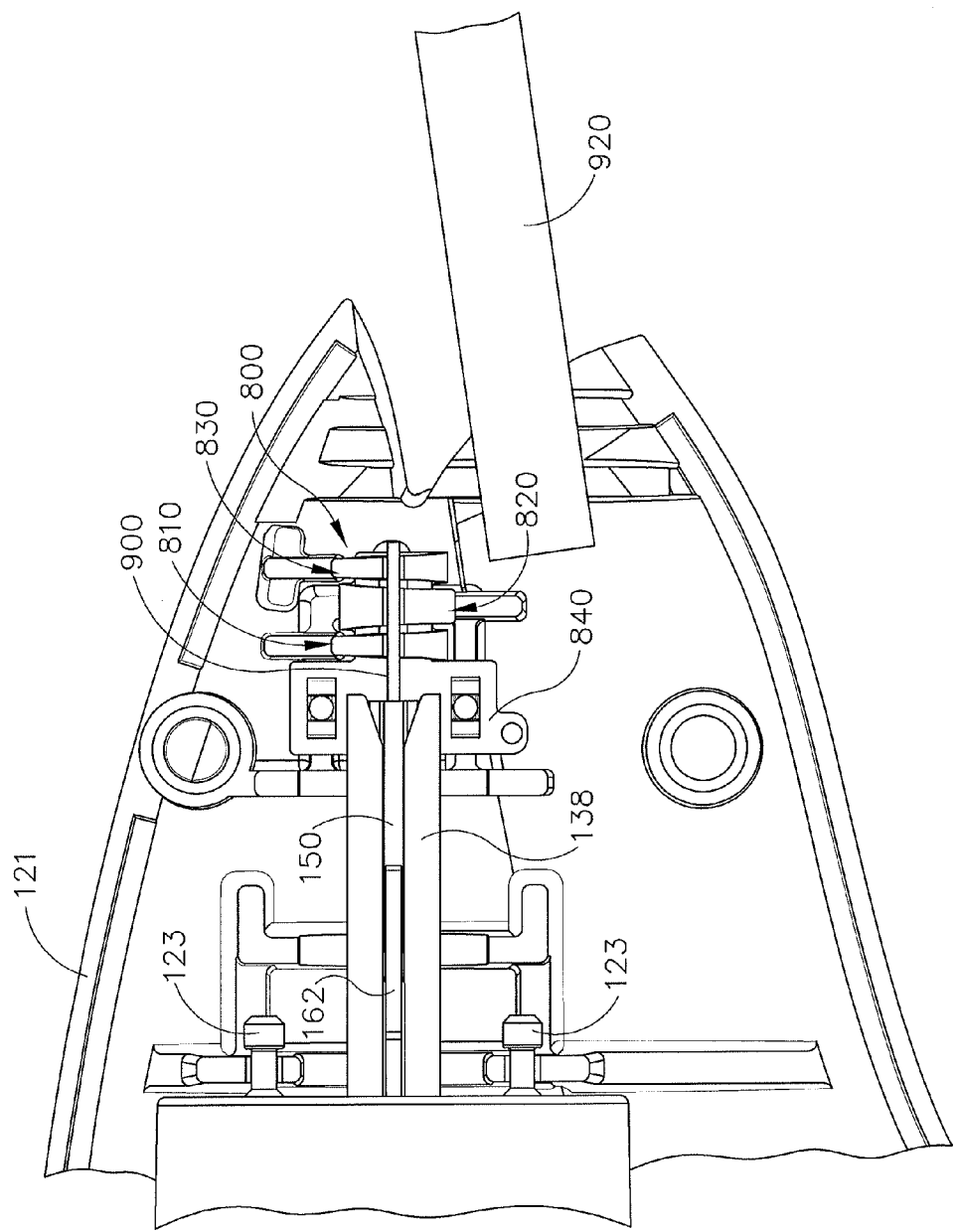
FIG. 35 depicts a side elevational view of a proximal portion of the handle assembly of the device of FIG. 5, with a housing half of the handle assembly removed.
Figure 36:
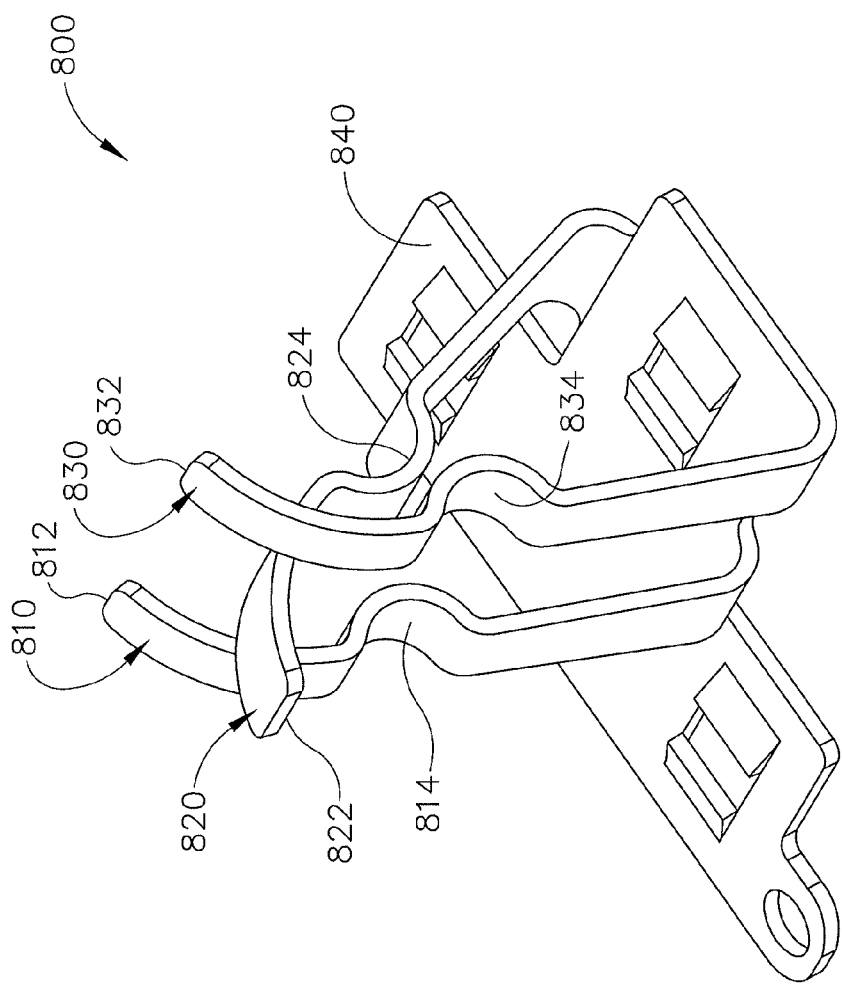
FIG. 36 depicts a perspective view of an exemplary electrical coupling of the proximal portion of FIG. 35.

As noted above, wire (900) extends through separator (150) to provide electrical communication to end effector (140). For instance, wire (900) may be in electrical communication with one or more electrodes of end effector (140). Wire (900) may thus serve as a ground return path for end effector (140) or may communicate active power to end effector (140). In some versions, wire (900) communicates active power to one or more electrodes of end effector (140) while driver tube (138) serves as a ground return path. FIGS. 35-36 show an exemplary conductive coupling (800) that may be used to electrically couple wire (900) with a power source or with electrical ground. Coupling (800) includes three arms (810, 820, 830) extending from a base (840). The free ends (812, 832) of arms (810, 830) are oriented in one direction while the free end (822) of arm (820) is oriented in the opposite direction, such that arms (810, 820, 830) have alternating orientations. As best seen in FIG. 36, each arm (810, 820, 830) includes a corresponding recess (814, 824, 834). Recesses (814, 824, 834) are configured to receive wire (900). Arms (810, 820, 830) are resiliently biased to assume the configuration shown in FIG. 36, such that arms (810, 820, 830) resiliently bear against wire (900) when wire (900) is disposed in recesses (814, 824, 834). Arms (810, 820, 830) thus maintain electrical continuity with wire (900), even if wire (900) is rotated relative to coupling (800). Wire (900) also has sufficient torsional strength to avoid twisting or winding when wire (900) is rotated relative to coupling (800), such that wire (900) will rotate within recesses (814, 824, 834).

As shown in FIG. 35, coupling (800) is positioned just proximal to the proximal end of driver tube (138) and separator (150). Wire (900) thus exits the middle lumen (152) of separator (150) and enters recesses (814, 824, 834) along a substantially straight line. In some versions, wire (900) continues past coupling (800) and into a wire sheath (920) that is coupled with housing (121). In the present example, however, wire (900) terminates at or just proximal to arm (834). Base (840) is secured to housing (121) and is further coupled with another wire (not shown) that communicates power to coupling (800) via base (840). This additional wire may be coupled with button (126), may be coupled with a control module (not shown), may extend through wire sheath (920), or may be otherwise provided. Other suitable structures and methods for electrically coupling wire (900) and/or end effector (140) will be apparent to those of ordinary skill in the art in view of the teachings herein.

B. Exemplary Return Stroke Assist

As noted above, a trigger (24, 124, 224, 324, 424) may be squeezed toward a pistol grip (22, 124, 224, 324, 424) to actuate an end effector (40, 140, 240, 340, 440). In the foregoing examples, a spring (not shown) resiliently biases trigger (24, 124, 224, 324, 424) away from pistol grip (22, 124, 224, 324, 424). Thus, after a user has fully squeezed trigger (24, 124, 224, 324, 424) toward pistol grip (22, 124, 224, 324, 424) to actuate end effector (40, 140, 240, 340, 440), the user may simply release trigger (24, 124, 224, 324, 424), and the spring may then return trigger (24, 124, 224, 324, 424) to a "home" position where it is pivoted away from pistol grip (22, 124, 224, 324, 424). In some versions, friction through articulation section (36, 136, 236, 336, 436) may provide substantial resistance to trigger (24, 124, 224, 324, 424) returning to the home position, particularly when articulation section (36, 136, 236, 336, 436) is in a bent configuration. This resistance may be most pronounced when trigger (24, 124, 224, 324, 424) is near the end of its return stroke. It may therefore be desirable in some instances to provide additional mechanical assistance to trigger (24, 124, 224, 324, 424) as it approaches the end of its return stroke.

Figure 37A:
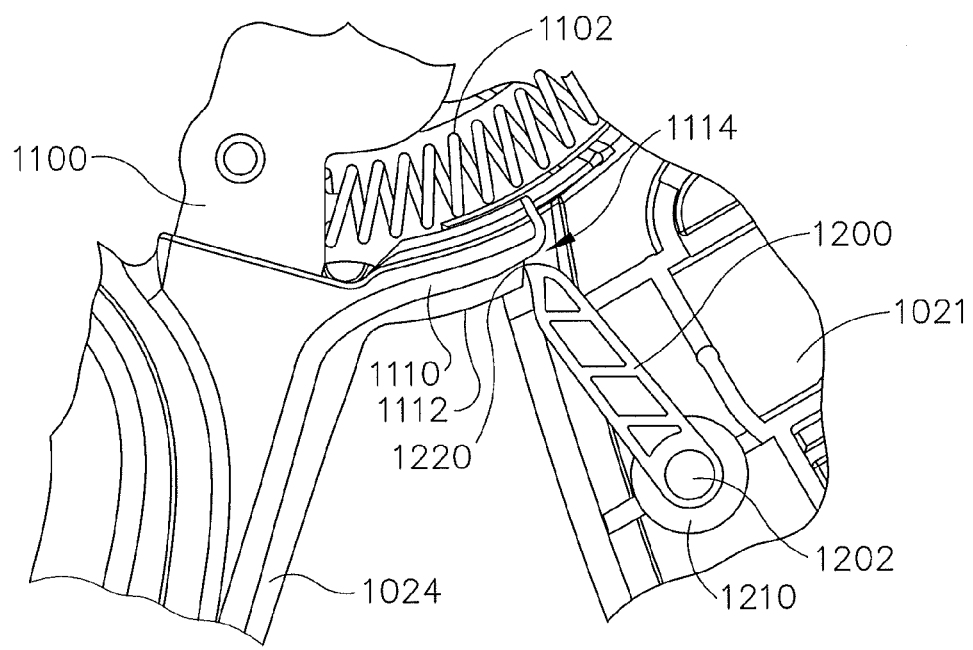
FIG. 37A depicts a side elevational view of a portion of a handle assembly including an exemplary return assist pivoting cam feature in a first position.
Figure 37B:
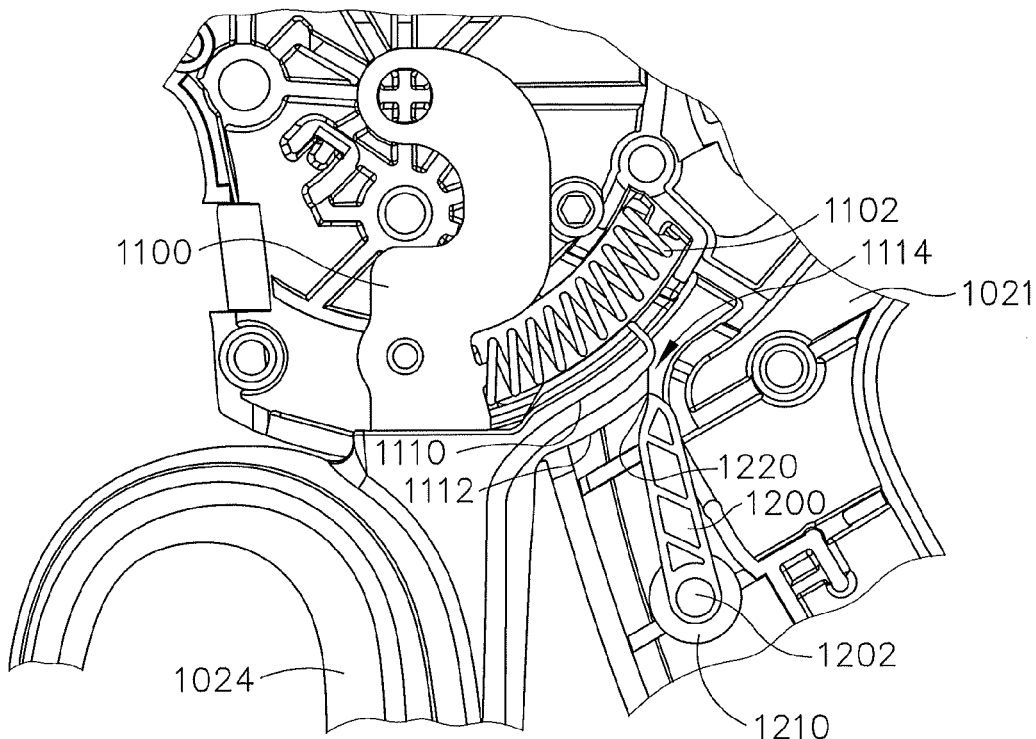
FIG. 37B depicts a side elevational view of the components of FIG. 37A, with the return assist pivoting cam feature in a second position.
Figure 37C:
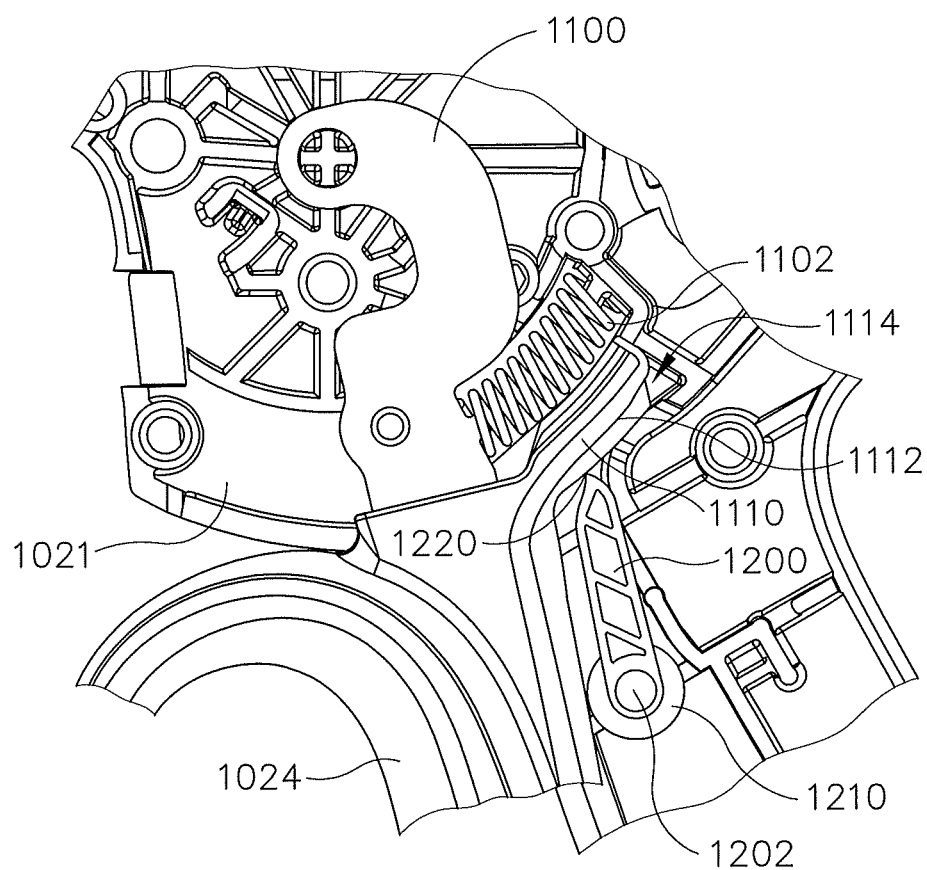
FIG. 37C depicts a side elevational view of the components of FIG. 37A, with the return assist pivoting cam feature in a third position.

FIGS. 37A-37C show exemplary components that may be used to assist the return stroke of trigger (24, 124, 224, 324, 424) from an actuated position (e.g., where trigger (24, 124, 224, 324, 424) is pivoted to pistol grip (22, 124, 224, 324, 424)) to a home position (e.g., where trigger (24, 124, 224, 324, 424) is pivoted away from pistol grip (22, 124, 224, 324, 424)). In this example, a trigger (1024) is pivotally secured to a housing (1021) of a handpiece by a pivot arm (1100). A coil spring (1102) is disposed between pivot arm (1100) and housing (1021), and is configured to resiliently bias trigger (1024) to the home position shown in FIG. 37A. Trigger (1024) also includes a proximally extending cam arm (1110) that engages a cam lever (1200) as will be described in greater detail below. Cam arm (1110) includes an underside (1112) and a notch (1114).

Cam lever (1200) is pivotally secured to housing (1021) by a pin (1202). A torsion spring (1210) is coaxially disposed about pin (1202) and resiliently biases cam lever (1200) to the rotational position shown in FIG. 37A. Cam lever (1200) includes a free end (1220) that engages either the underside (1112) of cam arm (1110) or the notch (1114) of cam arm (1110), depending on the rotational position of trigger (1024). In particular, free end (1220) remains substantially disposed in notch (1114) as trigger (1024) moves from a home position (FIG. 37A) through an angular range of approximately 15° to a partially actuated position (FIG. 37B). Then free end (1220) transitions to underside (1112) of cam arm (1110) as trigger (1024) continues to move to a fully actuated position (FIG. 37C), which is approximately 33° from the home position in the present example.

The spring constant of torsion spring (1210) is selected such that it does not significantly increase the resistance against actuation of trigger (1024) from the home position to the actuated position by a user. However, torsion spring (1210) does provide significant assistance to coil spring (1102) in returning trigger (1024) from the actuated position to the home position, particularly once trigger (1024) reaches the position shown in FIG. 37B. When trigger (1024) transitions from the fully actuated position shown in FIG. 37C to the partially actuated position shown in FIG. 37B during a return stroke, free end (1220) simply rides against the underside (1112) of cam arm (1110) and does not provide significant assistance to coil spring (1102) to return trigger (1024) toward the home position. However, once free end (1220) reaches notch (1114) during the return stroke of trigger (1024), cam lever (1200) is in a better position to mechanically drive cam arm (1100), and torsion spring (1210) thereby provides significant assistance to coil spring (1102) to return trigger (1024) from the position shown in FIG. 37B to the home position shown in FIG. 37A. Of course, any other suitable components, features, and configurations may be used to assist return of trigger (1024) to a home position. Alternatively, such components may simply be omitted if desired.

It should be understood that any of the devices herein may also include one or more of the various features disclosed in U.S. patent application Ser. No. 13/235,648, entitled "Control Features for Articulating Surgical Device," filed Sep. 19, 2011, published as U.S. Pub. No. 2012/0078244 on Mar. 29, 2012, the disclosure of which is incorporated by reference herein; U.S. patent application Ser. No. 13/235,660, entitled "Articulation Joint Features for Articulating Surgical Device," filed Sep. 19, 2011, now U.S. Pat. No. 9,402,682, issued on Aug. 2, 2016, the disclosure of which is incorporated by reference herein; and/or U.S. patent application Ser. No. 13/235,683, entitled "Articulation Joint Features for Articulating Surgical Device," filed Sep. 19, 2011, published Mar. 29, 2012 as U.S. Pub. No. 2012/0078248, now U.S. Pat. No. 9,220,559, issued on Dec. 29, 2015, the disclosure of which is incorporated by reference herein.

It should also be understood that any of the devices described herein may be modified to include a motor or other electrically powered device to drive an otherwise manually moved component. Various examples of such modifications are described in U.S. patent application Ser. No. 13/151,481, entitled "Motor Driven Electrosurgical Device with Mechanical and Electrical Feedback," filed Jun. 2, 1011, now U.S. Pat. No. 9,161,803, issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

VI. Miscellaneous

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An electrosurgical device, comprising:
 (a) a body comprising:
  (i) a housing comprising:
   (A) a proximal end, and
   (B) a distal end, and
  (ii) a controller positioned between the proximal end and the distal end of the housing, wherein the controller comprises:
   (A) an articulation knob configured to rotate relative to the housing,
   (B) a first translating member comprising a first proximally facing surface, wherein the first translating member is housed within the articulation knob, and
   (C) a second translating member comprising a second proximally facing surface, wherein the second translating member is housed within the articulation knob proximal to the first translating member, wherein the first translating member and the second translating member are configured to translate relative to the housing in opposing directions in response to rotation of the articulation knob relative to the housing;
 (b) an end effector comprising:
  (i) a first jaw, and
  (ii) a second jaw,
  wherein the first jaw is movable toward the second jaw to clamp tissue between the first and second jaw,
  wherein at least one of the jaws comprises at least one electrode,
  wherein the at least one electrode is operable to deliver RF energy to tissue clamped between the first and second jaw;
 (c) a cutting member operable to cut tissue clamped between the first jaw and the second jaw;
 (d) a shaft extending between the body and the end effector, wherein the shaft defines a longitudinal axis, wherein the shaft comprises an articulation section, wherein the articulation section is operable to selectively position the end effector at non-parallel positions relative to the longitudinal axis of the shaft, wherein the controller is operable to selectively actuate the articulation section,
 (e) a first articulation band configured to translate relative to the housing in response to translation of the first translating member, wherein the first articulation band comprises:
  (A) a first elongated member extending longitudinally through the shaft and the first translating member, and
  (B) a first drive member unitarily connected to the first elongated member, wherein the first drive member is configured to abut against the first proximally facing surface of the first translating member in order to proximally drive the first articulation band in response to proximal translation of the first translating member; and

(f) a second articulation band configured to translate relative to the housing in response to translation of the second translating member, wherein the second articulation band comprises:
  (A) a second elongated member extending longitudinally through the shaft, the first translating member, and the second translating member, and
  (B) a second drive member unitarily connect to the second elongated member. wherein the second drive member is configured to abut against the second proximally facing surface of the second translating member in order to proximally drive the second articulation band in response to proximal translation of the second translating member,
wherein first and second articulation bands are further coupled with the articulation section or the end effector to selectively bend or pivot the articulation section.

2. The electrosurgical device of claim 1, wherein the articulation knob is rotatable along a plane that is perpendicular to the longitudinal axis of the shaft.

3. The electrosurgical device of claim 1, wherein the articulation knob is rotatable about the longitudinal axis of the shaft along a plane that is oblique to the longitudinal axis of the shaft.

4. The electrosurgical device of claim 3, wherein the controller further comprises a ball drive, wherein the articulation knob is disposed about the ball drive.

5. The electrosurgical device of claim 1, wherein the articulation knob includes a first thread region and a second thread region, wherein the first thread region includes threading having a first orientation, wherein the second thread region includes threading having a second orientation, wherein the second orientation is opposite to the first orientation, wherein the articulation knob is operable to rotate the first and second thread regions in a common rotational direction simultaneously.

6. The electrosurgical device of claim 5, wherein the first translating member further comprises a first lead screw engaged with the first thread region, where the second translating member comprises a second lead screw engaged with the second thread region, wherein the first lead screw and the second lead screw are configured to translate in opposite longitudinal directions in response to the first and second thread regions being rotated in the common rotational direction.

7. The electrosurgical device of claim 1, wherein the first translating member further comprises a first tension member configured to adjust a first longitudinal location of the first proximally facing surface relative to the rest of the first translating member.

8. The electrosurgical device of claim 1, wherein the controller comprises a pivoting member, wherein the pivoting member is operable to bend or pivot the articulation section based on a pivot angle of the pivoting member relative to the body.

9. The electrosurgical device of claim 8, wherein the controller further comprises a pair of opposing racks, wherein the pivoting member includes a post and a pinion engaged with the racks, wherein the pinion is operable to simultaneously translate the racks in opposite directions in response to pivoting of the pivoting member, wherein the racks are operable to bend or pivot the articulation section based on opposing longitudinal motion of the racks.

10. The electrosurgical device of claim 8, wherein the pivoting member is pivotable along a pivot plane, wherein the articulation section is configured to bend or pivot along an articulation plane corresponding to the pivot plane, wherein the shaft and the controller are rotatable relative to the body and about the longitudinal axis of the shaft such that the pivot plane and the articulation plane are rotatable about the longitudinal axis of the shaft.

11. The electrosurgical device of claim 8, wherein the pivoting member comprises a fin engageable by a user's thumb.

12. The electrosurgical device of claim 8, wherein the controller further comprises a pair of linkage arms operable to transfer pivotal motion of the pivoting member into opposing translational motion of two translating members, wherein the translating members are operable to bend or pivot the articulation section in response to opposing translation of the translating members.

13. The electrosurgical device of claim 1, further comprising an elongate member extending through the shaft, wherein the elongate member is configured to conduct electrical power through the shaft or provide an electrical ground return through the shaft, wherein the elongate member is movable relative to the body, wherein the body includes a conductive coupling, wherein the conductive coupling is configured to contact the elongate member and maintain electrical continuity with the elongate member while the elongate member moves relative to the body.

14. The electrosurgical device of claim 13, wherein the conductive coupling is configured to contact the elongate member along at least two axes.

15. The electrosurgical device of claim 1, further comprising:
  (a) a trigger operable to actuate the cutting member, wherein the trigger includes a cam am; and
  (b) a trigger return lever engaged with the cam arm, wherein the trigger return lever is configured to bias the trigger to a home position.

16. A surgical instrument, comprising:
  (a) a body;
  (b) an end effector, wherein the end effector is operable to engage tissue;
  (c) a shaft extending between the body and the end effector, wherein the shaft defines a longitudinal axis, wherein the shaft includes an articulation section, wherein the articulation section is operable to selectively position the end effector at non-parallel positions relative to the longitudinal axis of the shaft; and
  (d) a controller operable to selectively actuate the articulation section, wherein the controller comprises:
    (i) a rotary member, wherein the rotary member is rotatable relative to the body,
    (ii) a first translating member comprising:
      (A) a first lead screw . and
      (B) a first tensioning member comprising a first proximally presented face, wherein the first lead screw and the first proximally presented face define a first distance, wherein the first tensioning , member is configured to adjust the first distance,
    (iii) a second translating member proximal relative to the first translating member, wherein the rotary member is configured to rotate in order to translate the first and the second translating members in opposing directions, wherein the second translating member comprises:
      (A) a second lead screw, and
      (B) a second tensioning member comprising a second proximally presented face, wherein the second lead screw and the second proximally presented face define a second distance, wherein the second tensioning member is configured to adjust the second distance, (iv) a first elongate member comprising a first drive projection,
wherein the first elongate member extends through the shaft and the first translating member such that the first drive projection abuts against the first proximally presented face of the first tensioning member, and (v) a second elongate member comprising a second drive projection, wherein the second elongate member extends through the shaft, the first translating member, and the second translating member such that the second drive projection abuts against the second proximally presented face of the second tensioning member, wherein the rotary member is operable to simultaneously translate the first and second translating members such that the first and second drive projections translate the first and second elongate members in opposite directions in response to rotation of the rotary member, wherein the first and second elongate members are configured to bend or pivot the articulation section in response to opposing longitudinal movement of the elongate members.

17. A surgical instrument, comprising:
(a) a body;
(b) an end effector, wherein the end effector is operable to engage tissue;
(c) a shaft extending between the body and the end effector, wherein the shaft defines a longitudinal axis, wherein the shaft includes an articulation section, wherein the articulation section is operable to selectively position the end effector at non-parallel positions relative to the longitudinal axis of the shaft; and
(d) a controller operable to selectively actuate the articulation section, wherein the controller comprises:
(i) a rotary member, wherein the rotary ember is rotatable relative to the body,
(ii) a first thread region, wherein the first thread region includes threading having a first orientation,
(iii) a second thread region, wherein the second thread region includes threading having a second orientation, wherein the rotary member is operable to rotate the first and second thread regions simultaneously in a common direction,
(iv) a first lead screw engaged with the first thread region,
(v) a second lead screw engaged with the second thread region, wherein the lead screws are configured to translate in opposite axial directions in response to the first and second thread regions being rotated in the common rotational direction, and
(vi) a pin comprising a first end, a second end, and a shaft extending from the first end to the second end, wherein the shaft of the pin extends through the first lead screw and the second lead screw, wherein the first lead screw and the second lead screw are slidably coupled with the shaft of the pin, wherein the first end and the second end are fixed to the body.

* * * * *